(12) United States Patent
Nelson et al.

(10) Patent No.: US 11,315,667 B2
(45) Date of Patent: Apr. 26, 2022

(54) PATIENT HEALTHCARE RECORD TEMPLATES

(71) Applicant: ZOLL MEDICAL CORPORATION, Chelmsford, MA (US)

(72) Inventors: Rene Nelson, Westminster, CO (US); Benjamin Barnett, Denver, CO (US); Keenan Early, Denver, CO (US); Bala Rajesh, Broomfield, CO (US); Justin M. Meredith, Lochbuie, CO (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 240 days.

(21) Appl. No.: 16/537,286

(22) Filed: Aug. 9, 2019

(65) Prior Publication Data

US 2020/0051675 A1    Feb. 13, 2020

Related U.S. Application Data

(60) Provisional application No. 62/718,080, filed on Aug. 13, 2018.

(51) Int. Cl.
*G16H 10/60* (2018.01)
*G16H 40/20* (2018.01)
(Continued)

(52) U.S. Cl.
CPC ............ *G16H 10/60* (2018.01); *G16H 15/00* (2018.01); *G16H 40/20* (2018.01); *G06Q 10/10* (2013.01); *G16H 80/00* (2018.01)

(58) Field of Classification Search
CPC ...... G06F 21/6245; G06F 30/13; G06F 3/011; G06F 16/51; G06F 16/953; G06F 30/20;
(Continued)

(56) References Cited

U.S. PATENT DOCUMENTS 5,267,155 A  11/1993  Buchanan et al.
6,106,459 A   8/2000  Clawson
(Continued)

FOREIGN PATENT DOCUMENTS

WO    2012100219 A1    7/2012

OTHER PUBLICATIONS

ZOLL Data Systems, "RescueNet ePCR 5.4.3 Defect Release Notes," Jan. 26, 2014, (1Page).
(Continued)

*Primary Examiner* — Maroun P Kanaan
(74) *Attorney, Agent, or Firm* — Finch & Maloney, PLLC

(57) ABSTRACT

A system for automatically expediting charting for an emergency medical services event includes databases with a pre-configured ePCR form including fillable fields and a first and a second ePCR template, the first and second templates specifying pre-determined values for first and second fillable field subsets and a computing device, configured to communicatively couple to the databases, that includes a user interface, a memory, and a processor configured to receive a request to generate an ePCR, access the pre-configured ePCR form, receive selections of the first and second ePCR templates, automatically populate at least portions of the fillable fields based on the templates by identifying non-overlapping fields and overlapping fields in the subsets of fillable fields, populating the non-overlapping fields with the pre-determined values, and populating the overlapping fields with the pre-determined values according to selection rules, and generate the ePCR based on the automatic population of the fillable fields.

28 Claims, 24 Drawing Sheets

(51) Int. Cl.
*G16H 15/00* (2018.01)
*G06Q 10/10* (2012.01)
*G16H 80/00* (2018.01)

(58) Field of Classification Search
CPC .... G06F 16/258; G06F 40/174; G06F 40/186; G16H 50/20; G16H 10/60; G16H 10/20; G16H 15/00; G16H 30/20; G16H 40/20; G16H 30/40; G16H 50/70; G16H 80/00; G06Q 10/10
See application file for complete search history.

(56) References Cited

U.S. PATENT DOCUMENTS

| | | | |
|---|---|---|---|
| 6,117,073 | A | 9/2000 | Jones et al. |
| 6,282,531 | B1 | 8/2001 | Haughton et al. |
| 6,607,481 | B1 | 8/2003 | Clawson |
| 6,610,010 | B2 | 8/2003 | Sjoqvist |
| 6,684,276 | B2 | 1/2004 | Walker et al. |
| 6,735,272 | B1 | 5/2004 | Sorenson |
| 7,039,628 | B2 | 5/2006 | Logan, Jr. |
| 7,044,742 | B2 | 5/2006 | Sumiya et al. |
| 7,412,395 | B2 | 8/2008 | Rowlandson |
| 7,490,085 | B2 | 2/2009 | Walker et al. |
| 8,712,793 | B2 | 4/2014 | Jones et al. |
| 2002/0004729 | A1 | 1/2002 | Zak et al. |
| 2003/0014222 | A1 | 1/2003 | Klass et al. |
| 2003/0105649 | A1 | 6/2003 | Sheiner et al. |
| 2003/0212575 | A1 | 11/2003 | Saalsaa et al. |
| 2004/0088317 | A1 | 5/2004 | Fabrick et al. |
| 2005/0149363 | A1 | 7/2005 | Loiterman et al. |
| 2006/0015254 | A1 | 1/2006 | Smith |
| 2007/0203742 | A1 | 8/2007 | Jones et al. |
| 2008/0243549 | A1 | 10/2008 | Woronka et al. |
| 2011/0295078 | A1 | 12/2011 | Reid et al. |
| 2012/0304054 | A1 | 11/2012 | Orf et al. |
| 2013/0096649 | A1 | 4/2013 | Martin et al. |
| 2013/0275151 | A1 | 10/2013 | Moore et al. |
| 2014/0019159 | A1 | 1/2014 | Singh et al. |
| 2014/0249854 | A1 | 9/2014 | Moore et al. |
| 2014/0337047 | A1 | 11/2014 | Mears et al. |
| 2016/0323417 | A1* | 11/2016 | Spear ............... G06Q 10/10 |
| 2017/0323055 | A1 | 11/2017 | Gaffield |

OTHER PUBLICATIONS

ZOLL Data Systems, "RescueNet ePCR Suite Administrator Guide," Softwarre version 5.4.3, 2015, (389 Pages).
ZOLL Data Systems, "RescueNet Dispatch—Billing Upgrade for Administrators," Oct. 21, 2015 (16 pages).
ZOLL Data Systems, "RescueNet Dispatch—Billing 4.6 Services Install Guide," Oct. 23, 2015, (34 Pages).
ZOLL Data Systems, "RescueNet TabletPCR and WebPCR User Guide," Software Version 5,4,3, 2015 (205 pages).
ZOLL Data Systems, "RescueNet Billing User's Guide," Software Version 4.6,2015, (450 pages).
ZOLL Data Systems, "RescueNet Billing—Dispatch Release Notes," Software Version 4.6.1,Dec. 8, 2015 (5 Pages).
ZOLL Data Systems, "RescueNet Dispatch—Billing Administration Guide," Release 4.6.1, Oct. 22, 2015, (740 Pages).
ZOLL Data Systems, "RescueNet Eligibilty Services Installation Guide," Software Release 4.6, 2015 (7 pages).
ZOLL Data Systems, "RescueNet ePCR 5.4.3 Feature release Notes," Jan. 26, 2014, (1 Sheet).
ZOLL Medical Corporation, "RescueNet TabletPCR and WebPCR", Software Version 5.2 Manual 5.2.2, Oct. 2011 (222 Pages).
ZOLL Data Systems, "ZOLL ePCR Cloud-Based ePCR That You Can Customize to Meet Your Needs", Copyright 2018 (2 pages).

* cited by examiner

| | 7/16/2008 1:31:48 PM |
|---|---|

01/16/2008 14:00    J. Johnson, E. Ericson    [veh: 101]

Current Crew

Open    New — b    Add Patient    Move    Merge    Print    Delete

PCRs checked out to your Inbox

| Run # | Status | First Name | Last Name | Address 1 | DC |
|---|---|---|---|---|---|
| 39 | Open | a | | | |
| 1 | Open | Michael | Westen | 12202 AIRPORT ... | |

Pending PCRs

| | | | | ≪ | < | > | ≫ |
|---|---|---|---|---|---|---|---|

| Run # | First Name | Last Name | Middle Name | Address 1 | |
|---|---|---|---|---|---|
| 2 | | | | 12202 AIRPORT ... | |

Request PCR    Save to Server    Messages    Help    Options

Exit

| Dispatch | | |
|---|---|---|
| Pickup Zone Number | | |
| Dispatch GPS location | | |
| Run Number | | |
| Call Source | Phone call | |
| Dispatch Center Name | Sleepy Hollow | |
| Dispatched complaint | Transfer/Interfacility/Palliative Care | |
| Patient Acuity | Priority 4 (Non-Acute) | |
| Trauma call type | Medical and Trauma | |
| Call type | BLS | |
| Response mode | Prescheduled | |
| Add'l response mode | No Lights or Sirens | |
| Response Delay | None/No Delay | |
| Dispatch Delay | None/No Delay | |

TEMPLATE EDITOR

Current company : First Ambulance — 601

Name your template : Patient Refusal — 602, 604

Apply this template to: ⦿ All Companies
○ Only this company (listed above)

Create — 606

PATIENT HEALTHCARE RECORD TEMPLATES

CROSS REFERENCE TO RELATED APPLICATIONS

This application claims priority under 35 U.S.C. § 119(e) to U.S. Provisional Application Ser. No. 62/718,080, titled "PATIENT HEALTHCARE RECORD TEMPLATES," filed Aug. 13, 2018, which is hereby incorporated herein by reference in its entirety.

BACKGROUND

The present disclosure is directed to systems and methods for documenting emergency medical care.

Electronic medical record systems enable medical and/or emergency care providers to document patient encounters. For example, an emergency medical services (EMS) crew may document a patient encounter via an electronic patient care record (PCR). The electronic PCR may include data collected from a caregiver via a computer implemented user interface provided at an endpoint device. Accurate and comprehensive documentation in the electronic PCR may improve, for example, patient care during the encounter, the continuity of care between EMS and hospitals, and overall patient health outcomes. For example, protocol adherence required by the electronic PCR may improve the care during the encounter. Continuity of care may benefit from a record that thoroughly describes symptoms, physiological metrics, and treatments provided. Other post-encounter services that may benefit from a high-quality electronic PCR include, for example, rehabilitative care, insurance reimbursement and claims, quality assurance/quality improvement processes, etc.

SUMMARY

It may be desirable and/or required to have complete and accurate records of patient information for an emergency medical event. However, entering patient charting information may be time-consuming and error-prone. Some government regulations and/or data reporting formats require certain information to be provided for an emergency medical event. Further, complete patient charting information may enable more efficient and effective care after emergency treatment, for example, when the patient arrives at the hospital. These requirements for complete charting information may mandate that the caregiver provide entries for a large number of data fields. Some of these data field entries may be the same from patient to patient based on, for example, a type of emergency call and/or patient condition. Time spent by medical personnel entering patient information may reduce the amount of time available for patient treatment and interaction. In certain situations, such as emergency medical events, where users are pressed for time, patient charting information entry by a clinical user (e.g., emergency medical care personnel) may be prone to inadvertent mistakes. Further, in order to save time, emergency personnel may postpone entry of information until after a call.

Thus, and in accordance with at least some examples described herein, patent charting systems and methods are provided for creating and managing electronic patient care reports (ePCRs).

In at least one example, a system for automatically expediting charting for an emergency medical services (EMS) event is provided. The system includes one or more databases and a computing device configured to communicatively couple to the one or more databases. The one or more databases store at least one pre-configured ePCR form including a plurality of fillable fields configured to store data regarding the EMS event. The one or more databases also store at least a first and a second ePCR template. The first ePCR template specifies a first plurality of pre-determined values for a first subset of the plurality of fillable fields. The second ePCR template specifies a second plurality of pre-determined values for a second subset of the plurality of fillable fields. The computing device includes at least one user interface, a memory, and at least one processor coupled to the at least one user interface and the memory. The at least one processor is configured to receive, via the at least one user interface, a request to generate an ePCR; access, in response to reception of the request, the at least one pre-configured ePCR form; receive a first input indicative of a selection of the first ePCR template; receive a second input indicative of a selection of the second ePCR template; automatically populate at least one portion of the plurality of fillable fields based on the first and the second ePCR templates; and generate the ePCR to include a plurality of populated fields based at least in part on the automatic population of the at least one portion of the plurality of fillable fields in the pre-configured ePCR form. In the system, to automatically populate the at least one portion of the plurality of fillable fields includes to identify, by the at least one processor, non-overlapping fields and overlapping fields in the first and the second subset of the plurality of fillable fields, automatically populate the non-overlapping fields with values from one of the first and the second plurality of pre-determined values, and automatically populate the overlapping fields according to pre-determined selection rules with one or more values from the first and the second plurality of pre-determined values.

Implementations of such a system for automatically expediting charting for an emergency medical services (EMS) event may include one or more of the following features. In the system, to automatically populate the non-overlapping fields can include to fill first fields of the non-overlapping fields with values from the first plurality of pre-determined values and fill, subsequent to filling the first fields, second fields of the non-overlapping fields with values from the second plurality of pre-determined values. In the system, to automatically populate the overlapping fields can include to fill, subsequent to filling the second fields, the overlapping fields with values from the first plurality of pre-determined values and apply the pre-determined selection rules to the overlapping fields using values from the second plurality of pre-determined values. The overlapping fields can include at least one single-use field and the pre-determined selection rules can be configured to cause the at least one processor to skip the at least one single-use field during application of the pre-determined selection rules. The overlapping fields can include at least one multi-select field and the pre-determined selection rules can be configured to cause the at least one processor to add a value from the second plurality of pre-determined values to the at least one multi-select field during application of the pre-determined selection rules. The overlapping fields can include at least one text field and the pre-determined selection rules can be configured to cause the at least one processor to add a value from the second plurality of pre-determined values to the at least one text field during application of the pre-determined selection rules.

In the system, to automatically populate can include to iterate through each of the non-overlapping and overlapping fields, to fill each non-overlapping field with a value from the first or the second plurality of pre-determined values, and to apply the pre-determined selection rules to each overlapping field using the one or more values from the first and the second plurality of pre-determined values. The overlapping fields can include at least one single-use field and the pre-determined selection rules can be configured to cause the at least one processor to fill the at least one single-use field with a value from the first plurality of pre-determined values during application of the pre-determined selection rules. The overlapping fields can include at least one multi-select field and the pre-determined selection rules can be configured to cause the at least one processor to fill the at least one multi-select field with one or more values from the first and/or the second plurality of pre-determined values during application of the pre-determined selection rules. The overlapping fields can include at least one text field and the pre-determined selection rules can be configured to cause the at least one processor to fill the at least one text field with one or more values from the first and/or the second plurality of pre-determined values during application of the pre-determined selection rules.

In the system, the at least one processor can be further configured to provide, in response to identification of the overlapping fields, a notification at the at least one user interface indicative of an overlap. The at least one processor can be further configured to identify a single-use field within the overlapping fields and prompt, in response to identification of the single-use field within the overlapping fields, a user to select a preferred value for the single-use field via the at least one user interface. The at least one processor can be further configured to automatically store the generated ePCR in the memory.

In the system, the plurality of fillable fields can have a total quantity, each fillable field of the plurality of fillable fields can have a data type, and the at least one processor can be further configured to prevent adjustment of the total quantity and the data type of each fillable field via selection of the first or the second ePCR template. The memory can store a configurable parameter that indicates requirements for the total quantity and the data type for each fillable field as mandated by one or more of a data reporting format and a governing body of a region in which the EMS event occurs. The at least one processor can be further configured to determine the total quantity and the data type of each fillable field by accessing the configurable parameter.

In the system, the one or more databases can include a basic emergency call template, a cardiac arrest template, a trauma template, a cancelled call template, a narrative template, a no cardiac arrest template, a no trauma template, a STEMI template, a demographics template, and/or combinations thereof. The narrative template can include headings for subjective, objective, assessment, and plan sections. The narrative template can include headings for Complaint, History, Assessment, Rx, Treatment sections. The narrative template can include one or more literals and/or one or more variables. The plurality of fillable fields can include a narrative field. The narrative template can include the one or more literals and the one or more variables. The one or more literals can specify static text for storage in the narrative field. The one or more variables can specify fillable fields with values for storage in the narrative field.

In the system, the first and the second plurality of pre-determined values can include preprogrammed administrator selected values. The preprogrammed administrator selected values can be specific to one or more EMS agencies. The preprogrammed administrator selected values can be independent of a patient identity. The preprogrammed administrator selected values can be specific to one or more EMS events. The preprogrammed administrator selected values can be specific to one or more responses to the one or more EMS events.

In the system, the at least one processor can be further configured provide, via the at least one user interface, one or more prompts to select the first and the second input. The at least one processor can be further configured to provide, via the at least one user interface in response to reception of the first input and/or the second input and prior to automatic population, a warning indicating that automatic population of the ePCR cannot be undone. The at least one processor can be further configured to provide, via the at least one user interface, a selectable undo control; receive third input indicative of a selection of the selectable undo control; and automatically de-populate the populated fields of the ePCR.

In the system, the first and the second plurality of pre-determined values can include recommended values and the at least one processor can be further configured to provide, via the at least one user interface, a prompt to accept or overwrite the recommended values. The at least one processor can be further configured to hide, within the at least one user interface, one or more controls associated with the populated fields of the ePCR. The at least one processor can be further configured to highlight, via the at least one user interface, one or more controls associated with the populated fields of the ePCR with a transparency, a color, and/or a shading that is different from controls associated with other fields of the ePCR. The at least one processor can be further configured to highlight, via the at least one user interface prior to automatic population of the at least one portion of the plurality of fillable fields, controls associated with the first and the second subset of the plurality of fillable fields with a transparency, a color, and/or a shading that is different from other fields of the plurality of fillable fields.

In the system, the at least one processor can be further configured to provide, via the at least one user interface, a plurality of ePCR template selection controls associated with corresponding ePCR templates stored in the one or more databases and the at least one processor is further configured to receive the first and/or the second input via at least one of the plurality of ePCR template selection controls. The at least one processor can be further configured to provide, via the at least one user interface, a selectable template request control; receive a third input indicative of a selection of the selectable template request control; and provide, in response to reception of the third input via the at least one user interface, the plurality of ePCR template selection controls. The at least one processor can be further configured to provide, via the at least one user interface, a search control to capture a template search string; receive a third input indicative of the template search string; generate, in response to reception of the third input via the at least one user interface, a filtered subset of ePCR templates stored in the one or more databases according to the template search string; and limit the plurality of ePCR template selection controls to ePCR template selection controls associated with ePCR templates within the filtered subset. The at least one processor can be further configured to provide, via the at least one user interface, the plurality of ePCR template selection controls as a menu list. The at least one processor can be further configured to provide, via the at least one user interface, the plurality of ePCR template selection controls as a plurality of labeled icons. The first ePCR template selection control of the plurality of ePCR template selection controls can correspond to the first ePCR template and a second ePCR template selection control of the plurality of ePCR template selection controls can correspond to the second ePCR template. The single ePCR template selection control of the plurality of ePCR template selection controls can corresponds to the first and the second ePCR template. The first ePCR template can be a chest pain template and the second ePCR template can be a chest pain intervention template.

In the system, the memory can store a cross-reference configured to store associations between ePCR templates stored in the one or more databases. The cross-reference can store an association between the first and the second ePCR template. The at least one processor can be further configured to identify correspondence between the single ePCR template selection control and the first and the second ePCR template via the cross-reference. The cross-reference can include a relational database table. The at least one processor can be further configured to store an association between two or more ePCR templates stored in the one or more databases where two or more ePCR template selection controls of the plurality of ePCR template selection controls corresponding to the two or more ePCR templates are selected in combination more than a threshold number of times by a user. The at least one processor can be further configured to provide, via the at least one user interface, a prompt to confirm the association between the two or more ePCR templates.

The system can further include an audio input device and/or a haptic input device. The first and/or the second input can include haptic input and/or audio input. The system can further include an audio input device configured to detect words within a conversation. The at least one processor can be further configured to identify, based on the first input and the second input, key words within the conversation.

The system can further include a medical device configured to communicatively couple to the computing device and store patient data. The computing device can be further configured to receive the first and/or the second input as a transmission of the patient data from the medical device. The patient data from the medical device can identify one or more physiological conditions of a patient and the first and/or the second ePCR template can correspond to the one or more physiological conditions of the patient. The medical device can be further configured to identify a STEMI condition of a patient based on an electrocardiogram of the patient. The patient data can identify the STEMI condition. The first and/or the second ePCR template can include a STEMI template. The patient data from the medical device can identify one or more patient treatments and the first and/or the second ePCR template can correspond to the one or more patient treatments.

In the system, one or more values of the first and/or the second plurality of pre-determined values can indicate one or more fields of the first and/or the second subset of the plurality of fillable fields are inapplicable to the EMS event. The at least one processor can be further configured to hide, within the at least one user interface, each control associated with a field of the one or more fields. The at least one processor can be further configured to provide, via the at least one user interface, one or more controls associated with the one or more fields, each control of the one or more controls having a transparency, a color, and/or a shading that different from other fields of the ePCR. The at least one processor can be further configured to automatically select, based on the first and the second plurality of pre-determined values, a third ePCR template stored in the one or more databases that specifies a third plurality of pre-determined values for a third subset of the plurality of fillable fields, the third plurality of pre-determined values comprising at least one value that indicates at least one field of the third subset of the plurality of fillable fields is inapplicable to the EMS event; and automatically populate the at least one field with the at least one value.

In the system, the ePCR can further include one or more trigger fields and the at least one processor can be further configured to provide, via the at least one user interface, one or more controls associated with the one or more trigger fields; capture, via the one or more controls, one or more values; identify one or more ePCR templates stored in the one or more databases in association with the one or more values of the one or more trigger fields; and provide, via the at least one user interface, one or more ePCR template selection controls corresponding to the one or more ePCR templates. The one or more trigger fields can include a first field configured to store a value indicative of an event disposition and a second field configured to store a value indicative of the EMS event. The first field can store a value indicative of a canceled call and the second field can store a value indicative of a 911 response. The memory can store a cross-reference configured to store associations between the one or more ePCR templates stored in the one or more databases and at least one value of the one or more trigger fields. In the system, to identify the one or more ePCR templates can include to identify, in the cross-reference, an association between the first and/or the second ePCR template and the one or more values of the one or more trigger fields; and identify, in response to identification of the association, the first and/or the second ePCR template as being the one or more ePCR templates. The cross-reference can include a relational database table. The memory can store a heuristic model comprising a plurality of rules configured to associate ePCR templates stored in the one or more databases with at least one value of the one or more trigger fields. The plurality of rules can include a rule associating the first and/or the second ePCR template with the one or more values for the one or more trigger fields. In the system, to identify the one or more ePCR templates can include to identify, within the heuristic model using the one or more trigger fields, the rule associating the first and/or the second ePCR template with the one or more values for the one or more trigger fields; evaluate the rule to identify the first and/or the second ePCR template as being the one or more ePCR templates. The at least one processor can be further configured to provide, via the at least one user interface, a prompt to confirm selection of the one or more ePCR template selection controls.

In the system, the at least one processor can be further configured to store a template log in the memory, the template log comprising time-stamped records of template selections and field-specific population records. The at least one processor can be further configured to provide, via the at least one user interface, at least one log control to present at least one portion of the template log. The ePCR can include at least one field storing a value entered by a user, the one or more databases stores a third ePCR template specifying a pre-determined value for the at least one field, and the at least one processor can be further configured to receive third input indicative of a selection of the third ePCR template and automatically replace, in response to reception of the third input, the value entered by the user with the pre-determined value.

In the system, the at least one processor can be further configured to receive third input indicative of one or more values of one or more unpopulated fields of the ePCR; and populate, in response to reception of the third input, the one or more unpopulated fields with the one or more values. The third input can include a selection of one or more user interface controls via a touchscreen, audible input, textual input generated by execution of an optical character recognition process on image data acquired by scanning a document, and/or patient data received from an electronic health record database.

In another example, a system for generating templates for automatically expediting charting for emergency medical services (EMS) events is provided. The system includes a first computing device. The first computing device includes a first memory and at least one processor coupled to the first memory. The at least one processor is configured to receive a request to create an ePCR template specifying one or more pre-determined values for each of one or more fillable fields in an ePCR form, provide a screen comprising a plurality of ePCR field controls that are each associated with a corresponding field of the one or more fillable fields, receive one or more values for each of the one or more fillable fields, and generate the ePCR template to specify the one or more values as the one or more pre-determined values for each of the one or more fillable fields in the ePCR form.

Implementations of such a system for generating templates for automatically expediting charting for emergency medical services (EMS) events may include one or more of the following features. In the system, each field of the one or more fillable fields can be applicable to a type of EMS event. The one or more fillable fields can include a first field for the type of EMS event and a second field for patient disposition. The first field can be filled with a value indicating the type of EMS event was a 911 response and the second field can be filled with a value indicating the EMS event was canceled. The system can further include a second computing device. The second computing device can include a second memory and one or more processors coupled to the second memory. The at least one processor can be further configured to receive a request to distribute the ePCR template to the second computing device and distribute, in response to reception of the request to distribute the ePCR template, the ePCR template to the second computing device. The one or more processors can be configured to receive a request to create an ePCR; receive a selection of the ePCR template; and populate, in response to reception of the selection of the ePCR template, a plurality of fillable fields in the ePCR corresponding to the one or more fillable fields specified in the ePCR template with the one or more values specified in the ePCR template. The one or more processors can be further configured to receive key words to find the ePCR template; and find, in response to reception of the key words, the ePCR template. The key words can associate the ePCR template with one or more of a basic emergency call template, a cardiac arrest template, a trauma template, a cancelled call template, a narrative template, a no cardiac arrest template, a no trauma template, a STEMI template, a demographics template, and/or combinations thereof. The one or more processors can be further configured to provide, in response to reception of the selection of the ePCR template and prior to populating the plurality of fillable fields in the ePCR, a warning specifying that population cannot be undone. The one or more processors can be further configured to receive input specifying values for unpopulated fields in the ePCR. The one or more processors can be further configured to receive a selection of an additional ePCR template; and populate, in response to reception of the selection of an additional ePCR template, a plurality of fillable fields in the ePCR corresponding to additional fillable fields specified in the additional ePCR template with additional values specified in the additional ePCR template. The at least one processor can be further configured to receive a designation of at least one fillable field of the ePCR template as a trigger field. The one or more values can be based on a treatment protocol for a patient condition associated with the ePCR template. The at least one processor can be further configured to designate the ePCR template as applicable to only one agency corresponding to an administrator. The at least one processor can be further configured to designate the ePCR template as applicable to one or more agencies corresponding to an administrator. The one or more values can include a value indicative of an inapplicable field based on a type of EMS event associated with the ePCR template.

In another example, a system for generating templates for automatically expediting charting for emergency medical services (EMS) events is provided. The system comprises a memory and at least one processor coupled to the memory. The memory stores at least one rule set applicable to at least one electronic patient care report (ePCR) form comprising a plurality of fillable fields. The at least one rule set requires at least one fillable field of the plurality of fillable fields be populated with at least one value. The at least one processor is configured to receive a request to generate a rule-based ePCR template based on the at least one rule set, and generate, based on the at least one rule set, at least one ePCR template specifying the at least one value for the at least one fillable field of the plurality of fillable fields in the ePCR form.

Implementations of such a system for generating templates for automatically expediting charting for emergency medical services (EMS) events may include one or more of the following features. In the system, the at least one value can include a plurality of values and the at least one fillable field can include two or more fillable fields. The at least one rule set can include a plurality of rules applicable to the at least one ePCR, each rule of the plurality of rules requiring one or more fillable fields specific to the rule be populated with one or more values specific to the rule. In the system, to generate the at least one ePCR template can include to generate a single ePCR template specifying the one or more values specific to each rule for the one or more fillable fields specific to each rule. The plurality of rules can include a first rule and a second rule, the first rule requiring one or more fillable fields specific to the first rule be populated with one or more values specific to the first rule and the second rule requiring one or more fillable fields specific to the second rule be populated with one or more values specific to the second rule. The one or more fillable fields specific to the first rule can overlap the one or more fillable fields specific to the second rule. The at least one processor is further configured to identify the overlap and provide, in response to identification of the overlap, a notification indicating the overlap. The one or more fillable fields specific to the overlap can be single entry fields and the at least one processor can be further configured to determine the one or more fillable fields specific to the overlap are single entry fields, and prompt, in response to determination of the one or more fillable fields specific to the overlap as single-use fields, a user to select a preferred value for the single-use field.

In the system, the at least one rule set can include a plurality of rules applicable to the at least one ePCR, each rule of the plurality of rules requiring one or more fillable fields specific to the rule be populated with one or more values specific to the rule. In the system, to generate the at least one ePCR template can include to generate at least one ePCR template specific to each rule, each at least one ePCR template specifying the one or more values specific to the rule for the one or more fillable fields specific to the rule. The at least one processor can be further configured to receive a request to distribute the at least one ePCR template and distribute, in response to reception of the request to distribute the at least one ePCR template, the at least one ePCR template to a distinct computing device. The request to generate a rule-based ePCR template can include an identifier of the rule set.

In another example, a system for charting an emergency medical services (EMS) event is provided. The system includes an electronic patient care report (ePCR) template database and a computing configured to communicatively couple to the ePCR template database. The ePCR template database includes a plurality of ePCR templates. Each ePCR template of the plurality of ePCR templates includes pre-determined values for a subset of a set of fields of an ePCR. The set of fields of the ePCR are configured to store data regarding the EMS event. The ePCR template database stores a first ePCR template and a second ePCR template. The computing device includes at least one user interface, a memory, and at least one processor coupled to the at least one user interface and the memory. The at least one processor is configured to receive, via the at least one user interface, a request to generate an ePCR, in response to reception of the request, open the ePCR, receive a first input indicative of the first ePCR template, receive a second input indicative of the second ePCR template, populate a subset of fields of the ePCR with the pre-determined values from the first ePCR template and the second ePCR template by executing a template layering process, and generate the ePCR.

Implementations of such a system for charting an emergency medical services (EMS) event may include one or more of the following features. In the system, the at least one processor can be further configured to automatically save the ePCR to the memory during population of the subset of fields, thereby storing the ePCR in the memory. The ePCR can include a total quantity of fields and can require a value type for each field of the total quantity of fields and the required value types can be unadjustable by the plurality of ePCR templates. The plurality of ePCR templates can include a basic emergency call template, a cardiac arrest template, a trauma template, a cancelled call template, a narrative template, a no cardiac arrest template, a no trauma template, a STEMI template, a demographics template, and/or combinations thereof. The pre-determined values can include preprogrammed administrator selected values. The preprogrammed administrator selected values can be specific to one or more EMS agencies. The preprogrammed administrator selected values can be independent of a patient identity.

In the system, the first ePCR template can specify a first plurality of pre-determined values and a first plurality of fields of the ePCR to populate with the first plurality of pre-determined values and the second ePCR template can specify a second plurality of pre-determined values and a second plurality of fields of the ePCR to populate with the second plurality of pre-determined values. The at least one processor can be further configured to successively populate the fields of the ePCR with the first plurality of pre-determined values from the first ePCR template and with the second plurality of pre-determined values from the second ePCR template according to the template layering process. The second plurality of fields can include one or more single-use fields that overlap the first plurality of fields and the template layering process can be configured to skip the one or more single-use fields during population of the fields of the ePCR with the second plurality of pre-determined values from the second ePCR template. The second plurality of fields can include one or more multi-select fields that overlap the first plurality of fields and the template layering process can be configured to add the second plurality of pre-determined values from the second ePCR template to the one or more multi-select fields during population of the fields of the ePCR with the second plurality of pre-determined values. The second plurality of fields can include one or more text fields that overlap the first plurality of fields and the template layering process can be configured to add the second plurality of pre-determined values from the second ePCR template to the one or more text fields during population of the fields of the ePCR with the second plurality of pre-determined values. The first plurality of fields can overlap the second plurality of fields and the template layering process can be configured to identify the overlap and provide, in response to identification of the overlap, a notification at the at least one user interface indicative of the overlap. The one or more fields specific to the overlap can be single entry fields and the template layering process can be configured to identify the one or more fields specific to the overlap are single entry fields and prompt, in response to determination of the one or more fillable fields specific to the overlap as single-use fields, a user to select a preferred value for the single-use field.

In the system, the at least one user interface can be configured to provide a plurality of ePCR template selection controls associated with corresponding ePCR templates of the plurality of ePCR templates and the at least one processor can be further configured to receive one or more of the first input and the second input via at least one of the plurality of ePCR template selection controls. The at least one user interface can be configured to provide a selectable template request control and provide the plurality of ePCR template selection controls in response to a user selection of the template request control. The at least one user interface can be configured to provide the plurality of ePCR template selection controls as a menu list. The at least one user interface can be configured to provide the plurality of ePCR template selection controls as a plurality of labeled icons. The first ePCR template selection control can correspond to the first ePCR template and a second ePCR template selection control can correspond to the second ePCR template. The at least one processor can be further configured to receive third input comprising values for fields of the ePCR unpopulated by the template layering process and populate the field of the ePCR based on the third input.

In one example, a system for charting a medical event includes a plurality of computing devices communicably coupled to a database. The system may be configured to receive charting data via input by a user at a first computing device of a plurality of computing devices, customize a template according to which the patient charting system prompts the user for entry of the charting data based on at least one of charting data and additional data, provide the template to a database, and electronically distribute the template to one or more second computing devices of the plurality of computing devices. Implementations of such as system may include one or more of the following features. The one or more second computing devices may be configured to capture input for template fields for the template during the medical event. The template may be a first template of a plurality of templates and the patient charting system may be configured to customize the plurality of templates, provide the plurality of templates to the database, and electronically distribute at least a second template of the plurality of templates to the one or more second computing devices. The one or more second computing devices may be configured to layer the first template and the at least the second template of the plurality of templates. The computing device may be a tablet computer. The patient charting system may be configured to customize the template via a series of user interface windows comprising at least one of user prompts and selection menus.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

FIGS. 1A and 1B are views of user interface screens provided by an ePCR application to generate the ePCR in accordance with at least one example disclosed herein.

FIG. 3A is a view of an ePCR edit screen in accordance with at least one example disclosed herein.

FIG. 3B is a view of an ePCR edit screen with a dialysis template applied in accordance with at least one example disclosed herein.

FIG. 13 is a view of a narrative population window provided by an ePCR application in accordance with at least one example disclosed herein.

FIGS. 14-18 are views of template set-up screens for configuring, distributing, and using ePCR templates in accordance with examples disclosed herein.

DETAILED DESCRIPTION

Figure 2:
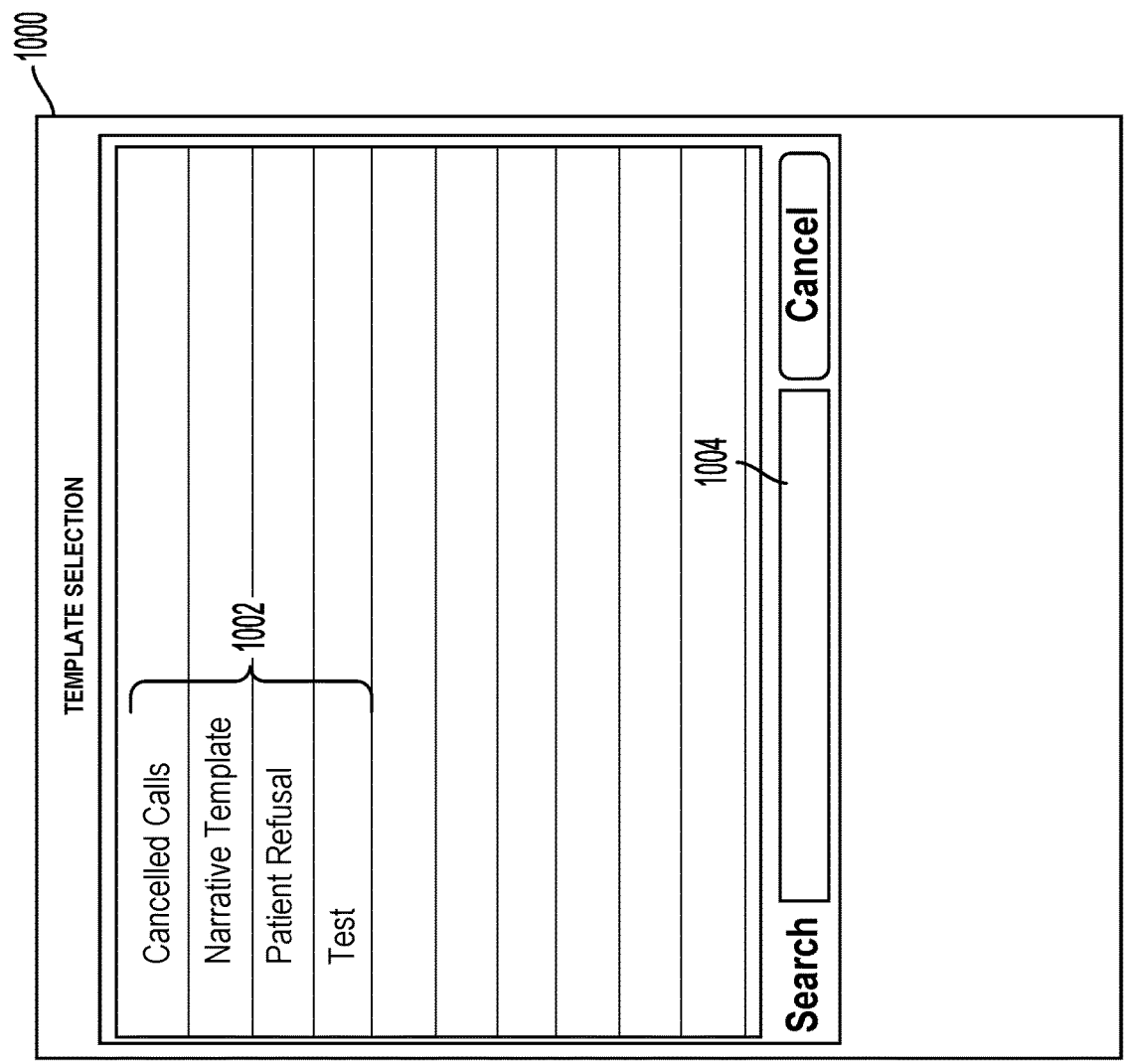
FIG. 2 is a view of a template selection window provided by an ePCR application in accordance with at least one example disclosed herein.

Complete and accurate patient information, including patient biographical information, medical condition, medications, allergies, and the like may impact accurate diagnosis and treatment. Complete and accurate patient information may also be provided to third parties such as care providers in a hospital to enable efficient and accurate treatment and patient family members to locate the whereabouts and/or to observe the condition of the patient. Assistance in entering such complete and accurate patient information may also save precious time for medical personnel, such that they may have more time to treat the patient, rather than spending time to enter patient charting information.

For example, consider an illustrative scenario of a crew of emergency medical services (EMS) caregivers in an ambulance being called upon to treat a patient suffering from an emergency medical condition (e.g., cardiac arrest, trauma, respiratory distress, drug overdose, etc.) and to transport the patient to a hospital. During the course of this emergency encounter, the EMS caregivers may be required to generate an electronic PCR (ePCR). This ePCR may comprise information regarding the patient, such as observed patient symptoms during the encounter, observed patient physiological parameters (such as heart rate, ECG traces, temperature, blood-oxygen data, and the like), and treatments or medications administered during the encounter. The patient charting information may include information, such as any known allergies to medication, relevant medical history, and/or additional patient medical conditions. This patient charting information may also include patient demographic information and/or information regarding the emergency medical event, such as type of service requested, response mode, and triage classification.

Due in part to data reporting format and/or content requirements for ePCRs, such as, for example, NEMSIS (National Emergency Medical Services Information) or HL7 (Health Level Seven International), EMS and/or other medical professionals often spend a significant amount of time documenting their patient encounters. In various implementations, the ePCR may include 50-1000 fields for which a data entry is required (e.g., required by laws of a state or another jurisdiction and/or required for adherence to a data collection standard such as NEMSIS). Since the user cannot reduce or customize the number of data entry fields, the accuracy and completeness of the ePCR may improve as a result of automated filling of at least a portion of these fields. The voluminous number of required fields may cause users to skip or rush through these fields, particularly in the context of an emergency response. However, skipped, inaccurate, and/or incomplete data entry may negatively affect patient care and patient outcomes.

NEMSIS is an example of an official EMS data collection standard for EMS agencies which allows transfer of data between systems and provides a national EMS repository for reporting and research. NEMSIS provides consistent definitions of data elements used in EMS and other pre-hospital care settings. The NEMSIS data collection via NEMSIS-compliant ePCRs may enable analysis of this data for evaluation of and evidence based improvements in patient care across an array of EMS agencies. In particular, the NEMSIS-compliant ePCRs conform to a structured XML standard for the ePCR data. NEMSIS and the XML standard are examples only and other formats and/or content requirements are within the scope of this disclosure. Governments and/or other authorities or agencies may also require various data content for an ePCR. Many of the required fields may be irrelevant to a particular emergency encounter and/or may include the same information for the particular emergency encounter regardless of the patient. Excessive time spent documenting data may contribute to a frustrating user experience for the caregiver and/or a degradation in the care provided to patients.

In some examples, the systems and methods disclosed herein allow administrators at an EMS agency to create customized ePCR templates for their crew members to use. When an ePCR template is selected by a crew member (e.g., an end user), the fields the administrator has designated may be filled instantaneously into the ePCR the crew has started. In some examples, the ePCR templates may be layered on top of each other so that when more information is known about the situation, the data fields that may not be relevant to the encounter and/or that may not be unique to the encounter may be filled quickly, allowing the end user to spend time documenting the specifics that are unique to that encounter with the patient.

In some examples, customized ePCR templates are created by the administrator on a computing device such as a computer tablet using an ePCR application (e.g., the ePCR application 160 discussed below), with administrator credentials. Personnel within each agency may customize their ePCR templates to their specific needs. Once an ePCR template is created, it may be electronically distributed to other tablets and/or computing devices (e.g., the computing device 104 discussed below). Once the ePCR templates are available on a computer tablet, an end user (e.g., the healthcare provider 114 of FIG. 4A) has the option to select from as many ePCR templates as her administrator has created. Various different ePCR templates may be available. An end user may select multiple ePCR templates and layer them on top of one another to fill out an ePCR more quickly. When the ePCR templates are selected, the ePCR application may execute an ePCR template layering process. The layering process may implement a copy/merge functionality of the ePCR application 160 to merge the ePCR template data into the ePCR on which the end user is actively working. The copy/merge functionality is described in further detail below with regard to FIG. 7. In an implementation, no pre-existing ePCR data is overwritten. The copy/merge operation executed by the ePCR template layering process may ignore anything that was previously documented by a medic or other healthcare provider to ensure that no data is lost. The previously documented entries may originate from a previously applied template and/or from direct user entry. Application of templates to the ePCR may be a quick fill feature or capability of the ePCR software.

The ePCR template capability may allow the end user to document a complete ePCR in a shorter amount of time by allowing him to apply an ePCR template that quickly fills in values that are the same on every call (dispatched EMS event) of that type. The ePCR templates may be layered on top of one another to add in more flexibility to this useful feature. This tool may provide advantages for EMS calls that are cancelled or calls for which the patient refuses service. In both of these cases, the information that the EMS professional may be required to collect may be daunting at least in part because of the large number of required ePCR fields. In some cases, the answers to these questions may be the same for most or every call of this type and so, to the documenter, the task may feel tedious and like a waste of valuable time. The tool described herein may allow the administrators to set up templates that will work based on the agency's specific reporting requirements and which may differ from reporting requirements for another agency, governing body, and/or data format.

Figure 1B:
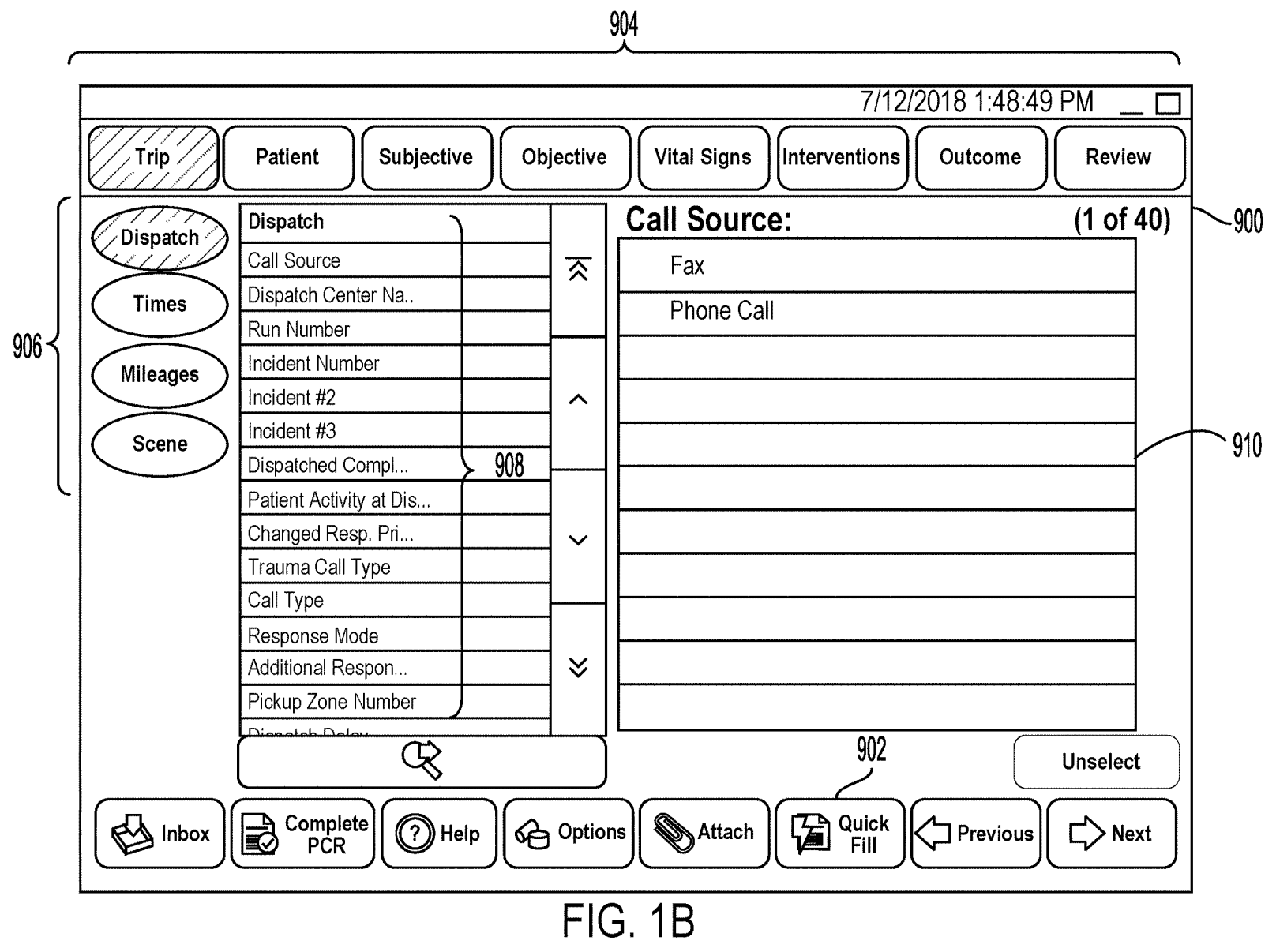

Referring to FIGS. 1A and 1B, examples of user interface screens provided by an ePCR application to generate the ePCR are shown. For example, the ePCR application (e.g., the ePCR application 160 shown in FIG. 4A) may provide an ePCR user interface (e.g., the ePCR user interface 180 shown in FIG. 4A). The ePCR user interface may include an ePCR initiation screen 198. A user (e.g., the healthcare provider 114 of FIG. 4A) may select an ePCR generation control 199 to open one or more new ePCRs. Until the ePCR is completed (e.g., as discussed below with regard to FIG. 3A) or deleted, the "open ePCR" may be an ePCR in progress.

As shown in FIG. 1B, in an exemplary implementation, selection of the ePCR generation control 199 may open the ePCR edit screen 900. The ePCR edit screen 900 may enable the user to generate the ePCR. The ePCR edit screen 900 may provide primary controls 904 and secondary controls 906. In the example shown in FIG. 1B, the primary control "trip" is selected. The secondary controls 906 that correspond to "trip" are dispatch, times, mileages, and scene. In this example, the secondary control "dispatch" is selected. Based on the selected primary and secondary controls, the ePCR application may provide a list 908 of selectable fillable fields and a selectable menu 910 of data entries for the selected fillable field. Via the selection of an item within the selectable menu 910, the ePCR application may enable the user to fill fields of the ePCR in progress in order to complete the ePCR.

In order to automate the filling of at least a portion of the fillable fields in the ePCR, the ePCR edit screen 900 may include a user-selectable template request control 902. For example, the user-selectable template request control 902 may be a quick fill control. The template request control 902 may be configured to capture a user request to access stored ePCR templates. The user of the ePCR user interface 180 may tap the template request control 902 to request access to the stored ePCR templates.

As illustrated in FIG. 2, in response to receiving a selection of the template request control 902, the ePCR application may provide a template selection window 1000. The template selection window 1000 may include a list of one or more selectable ePCR template controls 1002. Each of the one or more ePCR template controls 1002 may correspond to a stored and previously generated ePCR template. The user may select the ePCR template based on a type of EMS event (e.g., trauma, cardiac arrest, canceled call, etc.) and/or a particular section of the ePCR (e.g., biographical information, narrative, medications administered, etc.).

In an implementation, the template selection window 1000 may include a key word search control 1004. The key word search control 1004 may provide the user with the option of typing key words into the key word search control 1004 to find the template he/she seeks. In response to receiving input at the key word search control 1004, the ePCR application may store the input in the key word search control 1004 and may filter the list of selectable ePCR template controls 1002 to include only those ePCR template controls with a name that includes and/or matches the key word(s) currently present in the key word search control 1004.

In some examples, each selectable ePCR template control of the list of selectable ePCR template controls 1002 may be presented as an icon. Additionally or alternatively, in some examples, the list of selectable ePCR template controls 1002 may include single, selectable ePCR template controls that are associated with and correspond to a plurality of ePCR templates to allow the plurality of ePCR templates to be selected in unison. In an implementation, the ePCR application may capture a selection from the list of selectable controls 1002 via audio and/or haptic input to the computing device 104. This audio input may include words within a conversation recognized by the ePCR application as key words associated with the ePCR template associated with a particular ePCR template control.

As an example of an application of ePCR templates, every EMS response for a particular type of patient encounter for a particular agency may correspond to the same values for a number of ePCR fields. For instance, in the example of Table 1 below, every dialysis call for the Verifast EMS service may have the values shown in the filled fields of a trip dispatch section of the ePCR. Similarly, in the example of Table 2 below, every dialysis call for the Verifast EMS service may have the values shown in the filled fields of an outcome section of the ePCR. These values are examples only and not limiting of the disclosure. The applied template may not provide values for fields in the ePCR being generated that vary from call to call. The ePCR application may require the end user to provide entries for fields not filled by the template. Upon selection of the "Dialysis" template by the end user the ePCR template may insert the values for the fields as shown in the example below into the ePCR being generated by the caregiver. For example, the template may provide a value of "not applicable" to fields that are not applicable to the call. Even though these fields may be irrelevant to the type of call, the ePCR may require entries of "not applicable" or an equivalent designation. Without the benefit of the template, the caregiver may spend an inordinate amount of time entering "not applicable" or the equivalent designation into each of these irrelevant fields. This time may detract from the ability of the caregiver to provide optimum care and attention to the patient and/or may discourage the caregiver from thoroughly completing the ePCR and possibly missing fields important to the follow-up care for the patient. This time may also cause the caregiver to postpone completion of the ePCR until sometime after the encounter which may reduce the accuracy of the report and/or limit the availability of the report to follow-on care providers.

TABLE 1

| ePCR Field-dispatch section | Field value for Dialysis Template |
| --- | --- |
| Call Source | Phone call |
| Dispatch Center | Verifast EMS Services |
| Run Number | |
| Incident Number | |
| Dispatched Complaint | Palliative Care |
| Patient Acuity at Dispatch | Priority 4 (Non-Acute) |
| Changed Priority | Pre-Scheduled |
| Trauma call type | Medical and trauma |
| Call type | BLS |
| Response Mode | Pre-Scheduled |
| Additional Response Mode | No lights or Sirens |
| Pickup Zone | |
| Response Delay | None |
| Responding with | |
| Dispatch delay | None |

TABLE 2

| ePCR Field-outcome section | Field value for Dialysis Template |
| --- | --- |
| Fluid contact | |
| Patient Disposition | Treated & transported |
| Instructions provided | |
| Trauma center criteria | Not applicable |
| Level of care | BLS |
| Barriers to care | Not applicable |
| Cancel reason | |
| Type of service | Interfacility transport |
| Standby purpose | |
| Response urgency | Non-immediate |

Figure 3A:
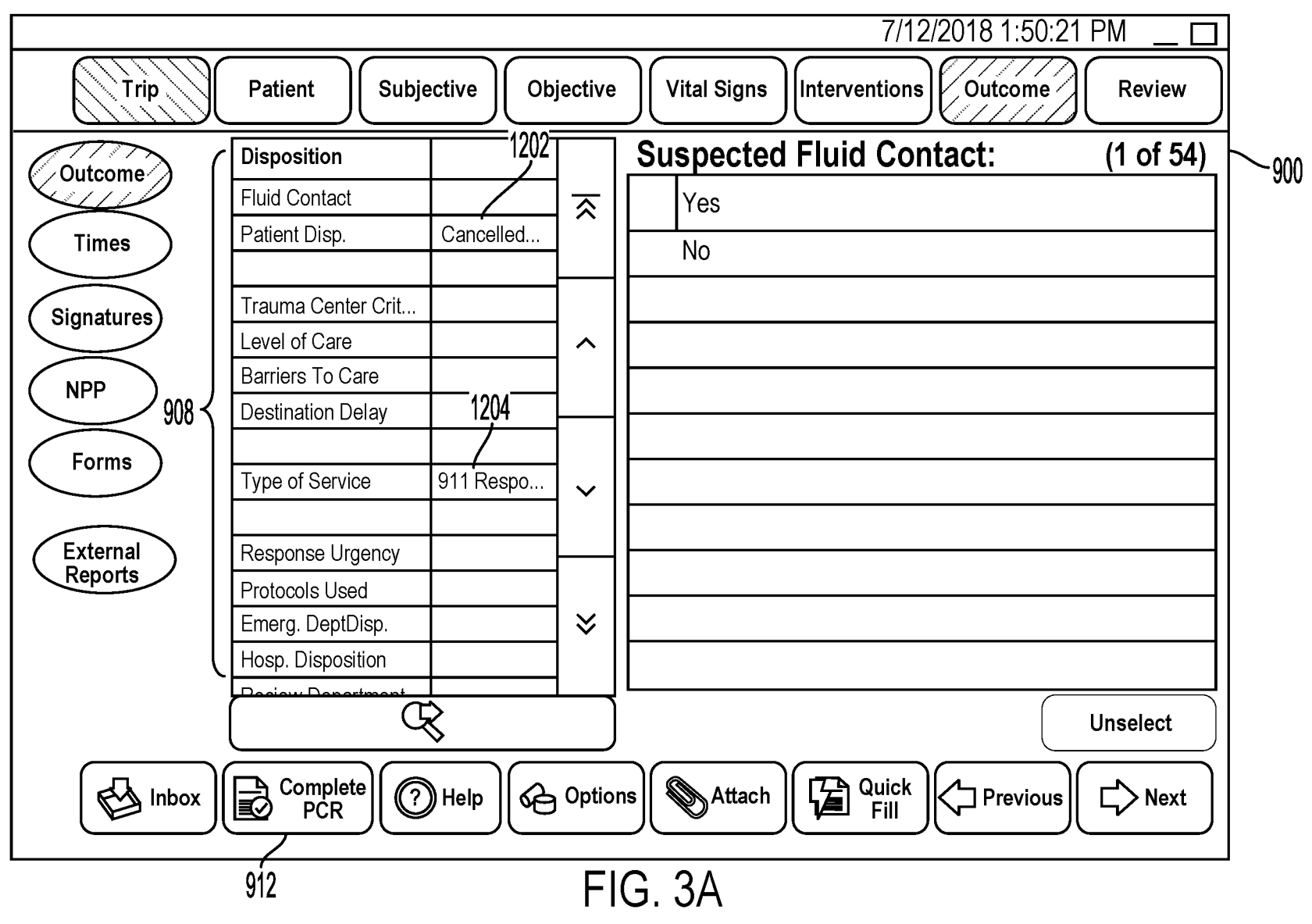

FIG. 3A illustrates an example of the ePCR edit screen 900 in which the fields of the ePCR corresponding to those of the ePCR template have been filled with values corresponding to the ePCR template. In this example, the fields 1202 and 1204 have been filled out by the ePCR template automatically. In some examples, the ePCR application highlights these fields by, for example, presenting them inside controls with a color, shading, and/or transparency that is different from controls presenting other, unpopulated fields. The user may verify that the autofill values from the ePCR template are correct. The ePCR application may provide an undo option on a field-by-field basis for correction of the autofill values.

At this point, the user may enter data into remaining fillable fields for which a template and/or a template value is unavailable. These fields may be specific to the particular EMS encounter and not amenable to pre-determination by an administrator. In some examples, the ePCR application may be configured to accept a variety of types of input to specify values of unpopulated fields. Examples of the types of input that the ePCR application may accept include touchscreen input, audible input, textual input extracted from image data via an optical character recognition process, and data received from an electronic health records system via a communications interface.

The user may select a completion control 912 to complete the ePCR. Completion may include a prompt for a signature and may automatically store the completed ePCR (e.g., storage may be at a local computing device such as the computing device 104 shown in FIG. 4A) and/or at one or more remote servers such as the server(s) 128 shown in FIG. 4A).

FIG. 3B illustrates an ePCR edit screen with a dialysis template applied. As indicated by the shading on the "dispatch" control 990, the portion of the ePCR related to dispatch for the dialysis call is displayed on the ePCR edit screen. As a result of selection of the dialysis template, the fields 992 are filled with the values 993 from the dialysis template. The values 993 are, for example, values predetermined by the administrator who created the dialysis template and correspond to values that may be the same for every dialysis call. The fields 995 are examples of fields that may vary from call to call for which the dialysis template may not provide values. Thus, as shown in this example, the areas for value entry 996 may be unfilled unless provided manually by the user. This example includes one page in the ePCR, and in an implementation the applied template may include values for fields in one or more pages of the ePCR as accessed via the controls 904. In this example, the "trip" control of the controls 904 is selected.

Figure 3C:
FIG. 3C is a view of an ePCR edit screen with a "no cardiac arrest" template applied in accordance with at least one example disclosed herein

FIG. 3C illustrates an ePCR edit screen with a "no cardiac arrest" template applied. In this example, the "trip" and "outcome" controls of the controls 904 are selected and the "cardiac arrest" control 997 is selected. The "cardiac arrest" control 997 may be a standard control of the ePCR regardless of whether or not the patient has experienced cardiac arrest. Furthermore, the user of the ePCR may be required to select this control and may be required to fill in values for the fields 998 that pertain to cardiac arrest even in the absence of a cardiac arrest. The appropriate values for all of the fields 998 in the absence of the cardiac arrest may be "not applicable." Without a template, the user may select each of the fields 998 and enter "not applicable" into each field one at a time. In contrast, application of the "no cardiac arrest" template may autofill all of these unapplicable fields with the "not applicable" value 999. This example includes one page in the ePCR, and in an implementation the applied template may include values for fields in one or more pages of the ePCR as accessed via the controls 904. In the example of the "no cardiac arrest" template, the user of the ePCR application may apply this template to fill in required cardiac arrest fields as "not applicable" and may further apply one or more additional templates that pertain to the type of call to fill in values for fields not filled by the "no cardiac arrest" template and/or may manually fill in values for these fields. For example, on a dialysis call, the user may apply the "no cardiac arrest" template to fill in fields pertaining to cardiac arrest as "not applicable" and may also apply the dialysis template to fill in fields relevant to dialysis.

Figure 4A:
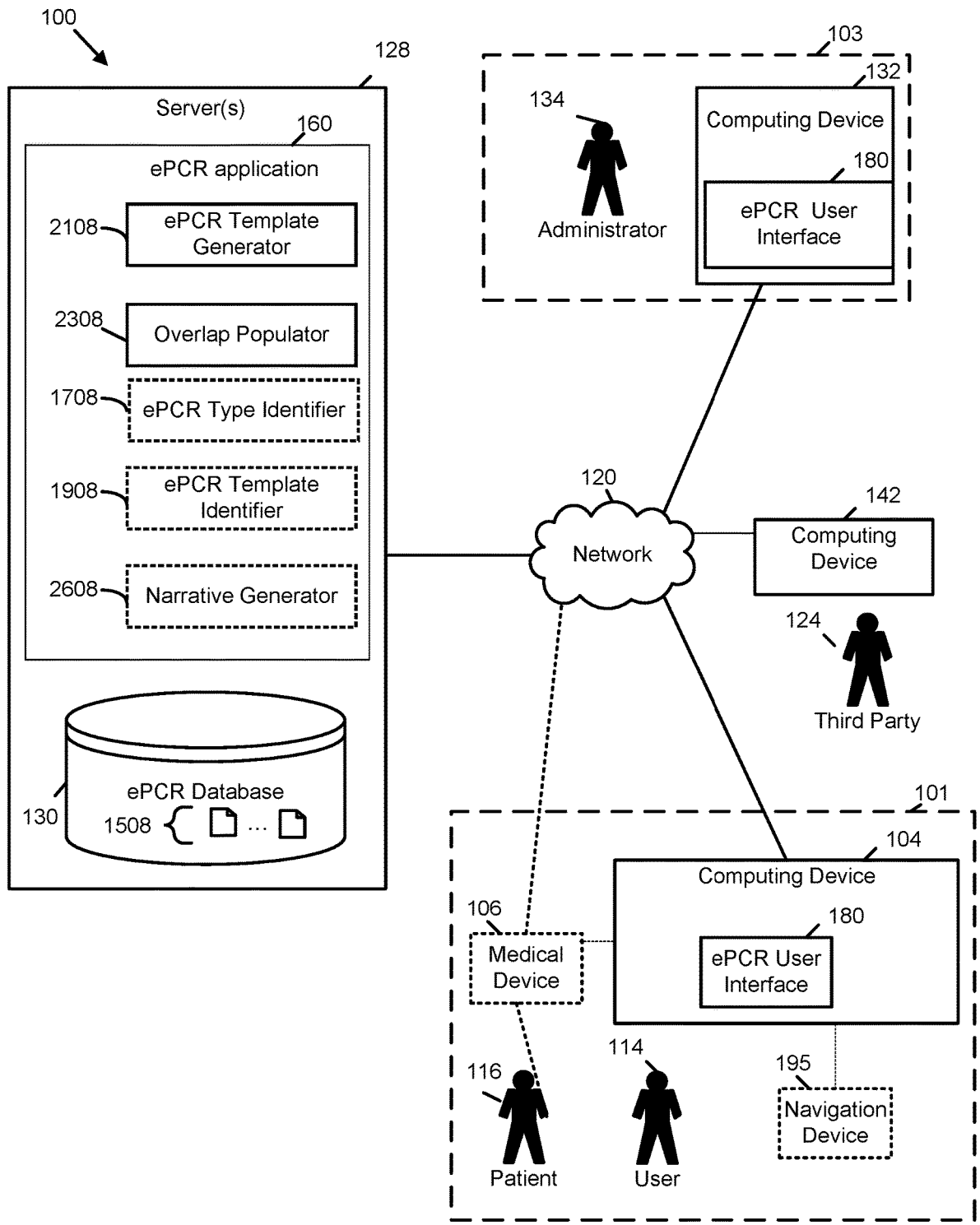
FIGS. 4A and 4B are block diagrams that illustrate a system for generating an electronic patient care report (ePCR), according to some examples.

Referring to FIG. 4A, an example of a system for providing a computer implemented ePCR application is shown. For example, the system 100 may provide the ePCR application 160.

The system 100, according to examples of the present disclosure, may perform advanced data management, integration, and presentation of EMS data from multiple different devices. This EMS data, as it relates to a particular EMS event, may be used by the system 100 to create the ePCR to document the EMS event. As shown in FIG. 4A, the system 100 may include a mobile environment 101, one or more servers 128, and an administration environment 103. Devices within the environments 101 and 103 may be communicably coupled via a network 120. In some examples in accord with FIG. 4A, the network 120 may include one or more communication networks through which the various computing devices illustrated in FIG. 4A may send, receive, and/or exchange data. In various implementations, the network 120 may include a cellular communication network and/or a computer network. In some examples, the network 120 includes and supports wireless network and/or wired connections. For instance, in these examples, the network 120 may support one or more networking standards such as GSM, CMDA, USB, BLU-ETOOTH®, CAN, ZigBee®, Wireless Ethernet, Ethernet, and TCP/IP, among others. The network 120 may include both private networks, such as local area networks, and public networks, such as the Internet. It should be noted that, in some examples, the network 120 may include one or more intermediate devices involved in the routing of packets from one endpoint to another. However, in other examples, the network 120 may involve only two endpoints that each have a network connection directly with the other.

The mobile environment 101 may include a computing device 104 (for example, a patient charting device) configured to enable the user to provide care to a patient 116. The computing device 104 may be a device used by the healthcare provider 114 to generate the ePCR and/or other records and/or notes about the condition of the patient 116 and/or treatments applied to the patient 116, according to examples of the present disclosure. The computing device 104 includes a processor coupled with memory configured to store data manipulated by the processor. The components of the computing device 104 are discussed in further detail below with regard to FIG. 20.

The computing device 104 may include the ePCR application 160 stored in the memory and executable by the processor. Alternatively or additionally, the memory of the computing device 104 may store a browser, or some other execution environment, configured to receive and render the ePCR interface from a webserver or other cloud-based server(s) (e.g., the server(s) 128). In these examples, the computing device 104 may be a tablet, smartphone, wearable device, and/or other mobile computing device and/or a combination of mobile devices that can access the ePCR application capabilities described herein via a server or cloud interface, for example, an interface with the server(s) 128.

The computing device 104 may include a combination of devices, according to some examples. The computing device 104 may receive and/or send data from and/or to other devices like a medical device 106. Alternatively or additionally, in some examples, the computing device 104 may communicate with another device or system which aggregates or otherwise receives data from other devices, such as the medical device 106. In some examples, the computing device 104 may include a touchscreen and/or a flat panel PC. The computing device 104 may include a display template serving as a graphical user interface, which permits the user to select different subsets and/or display modes of the information gathered from and/or sent to other devices, according to examples of the present disclosure.

For example, the computing device 104 may be utilized to access the patient charting system as described herein. In one example, the computing device 104 may be used to note a dosage of medicine or other treatment given to the patient at a particular time. The computing device 104 and/or the medical device 106 may have a clock, which may be synchronized with an external time source such as a network resource or a satellite to prevent the healthcare provider from having to manually enter a time of treatment or observation (or having to attempt to estimate the time of treatment for charting purposes long after the treatment was administered), according to examples of the present disclosure. The computing device 104 may also be used to record biographic and/or demographic and/or historical information about a patient, for example the patient's name, identification number, height, weight, and/or medical history, according to examples of the present disclosure. According to some examples of the present disclosure, the computing device 104 may include a wristband and/or smart phone such as an Apple® iPhone® or iPad® with an interactive data entry interface such as a touch screen or voice recognition data entry interface that may be communicably coupled to the tablet and tapped to indicate what was done with the patient 116 and when it was done. According to some examples of the present disclosure, the computing device 104 may be integrated with the medical device 106, such that a single device may be configured to monitor the patient, treat the patient, as well as to generate records and/or notes about the patient's condition and/or treatments applied to the patient 116. In these examples, the ePCR application may be embedded within the combination medical/computing device.

According to some examples of the present disclosure, the mobile environment 101 may include a vehicular mobile environment (VME) based in an ambulance or other EMS vehicle and/or an "At Scene Patient Mobile Environment" (ASPME). The mobile environment 101 may also include a local network including data entry devices as well as diagnostic and/or therapeutic medical devices. This local network may be established in an ad-hoc manner at the time of treatment of a patient or patients in the field and may include two or more devices within the VME and/or the ASPME.

In some examples involving VMEs, the mobile environment 101 may include a navigation device 195. The navigation device 195 may enable the user to track the position of the mobile environment 101. The navigation device 195 may also be used to locate the mobile environment 101, an emergency location, and/or a transport destination (e.g., a hospital or other medical care facility). The navigation device 195 may include a Global Positioning System (GPS), for example. In an implementation, the navigation device 195 may be a dispatch device that may provide navigation information along with dispatch information such as, but not limited to, a time of an emergency dispatch, a type of emergency, information about an emergency response from an EMS agency, patient information, etc. The navigation device 195, the computing device 104, and the medical device 106 may each be useful to the user before, during, and after patient transport.

In various implementations, the computing device 104 may receive, organize, store, share, distribute, and display data from the other devices (e.g., the medical device 106 and/or the navigation device 195) to further enhance the usefulness of these devices and to make it easier for the healthcare provider 114 to perform certain tasks that would normally require the healthcare provider 114 to divert visual and manual attention to the other devices separately, according to examples of the present disclosure. In other words, the computing device 104 may centralize, organize, and share (e.g., with the other devices in the mobile environment 101) information that might otherwise be de-centralized and disorganized, according to examples of the present disclosure.

As illustrated in FIG. 4A, in some examples, the mobile environment 101 may include a patient monitoring/medical device 106. In some examples, the healthcare provider 114, who may be an EMS technician, may attach the medical device 106 and/or sensors associated with the medical device 106 to the patient 116 to monitor and/or treat the patient 116. As illustrated in FIG. 4A, in some examples the computing device 104 may be communicably coupled to the medical device 106.

The medical device 106 may be, for example, a defibrillator with electrodes and/or sensors configured for attachment to the patient 116 to monitor heart rate and/or to generate electrocardiographs (ECGs), according to examples of the present disclosure. The medical device 106 may also include sensors to detect and/or a processor to derive or calculate other patient conditions. For example, in some examples, the medical device 106 may monitor, detect, treat, and/or derive or calculate blood pressure, temperature, respiration rate, blood oxygen level, end-tidal carbon dioxide level, pulmonary function, blood glucose level, and/or weight, according to examples of the present disclosure. In various implementations, the medical device 106 may be a patient treatment device, or another kind of device that includes patient monitoring and/or patient treatment capabilities, according to examples of the present disclosure. For example, the medical device 106 may be a defibrillator and may be configured to deliver therapeutic electric shocks to the patient. In some examples, the medical device may deliver other types of treatments, such as ventilation, operating a respirator, and/or administering drugs or other medication.

According to some examples of the present disclosure, the medical device 106 may include a wearable medical device, such as, for example, a Lifevest® wearable defibrillator. In these examples, the computing device 104 may communicably couple (e.g. automatically or manually or selectively) with the wearable medical device to receive and display patient monitoring information. The computing device 104 may also be configured to receive patient-identifying information from the wearable medical device, to permit the computing device 104 to query an external database, for example across network 120, to retrieve additional information about the patient. The computing device 104 may also be configured to connect with an implantable cardioverter-defibrillator ("ICD") in a similar fashion, according to examples of the present disclosure.

The server(s) 128 (e.g., one or more application servers) may include the ePCR application 160 and an ePCR data store 130. The server(s) 128 may communicate with one or more of the computing device 132 and the computing device 104 via the network 120. The server(s) 128 may be cloud based servers or enterprise servers. In an implementation, the administrative environment 103 may include all or a portion of the server(s) 128.

The computing device 104 may provide the ePCR user interface 180 for the ePCR application 160. Additionally, the computing device 132 may provide the ePCR user interface 180. The ePCR user interface 180 and the ePCR application 160 may implement the patient charting system capabilities described herein. These capabilities may include an ePCR template generation process and an ePCR template application process. These processes may enable automated population of the fields of an ePCR. Some examples of these processes are described in further detail below.

In some examples, the ePCR application 160, the computing device 104 and/or the computing device 132 may provide the user interface 180 via one or more physical interface devices such as input devices, output devices, and combination input/output devices and a software stack configured to drive operation of the devices. The user interface 180 may render visual, audio, haptic, and/or tactile content, including content relating to ePCR generation. Thus the user interface 180 may receive input or provide output, thereby enabling a user to interact with the computing device 104 and/or the computing device 132. In some examples, the user interface 180 includes the input devices 444 and/or the output devices 430 of FIG. 20.

Although FIG. 4A depicts a single computing device 104 in the mobile environment 101, in certain examples more than one computing device 104 may be used in the mobile environment 101 to communicably connect to the same or a different set of the other devices in the mobile environment 101. Further, although FIG. 4A depicts one mobile environment 101, more than one mobile environment 101 and/or more than one computing device 104 may be communicably coupled with the administration environment 103 and/or the one or more servers 128, according to examples of the present disclosure. According to examples of the present disclosure, the one or more servers 128 may receive EMS device information from computing device 104 and store it in ePCR data store 130 along with an authenticated timestamp and an identifier associating the information with a particular EMS device and/or a particular EMS vehicle. In this way, data from multiple vehicles and/or multiple devices may be accessed by various users (e.g., the users 114, 134, and/or 124).

As shown in FIG. 4A, the ePCR application 160 may include an ePCR template generator 2108 and an overlap populator 2308. Optionally, the ePCR application 160 may include an ePCR type identifier 1708, an ePCR template identifier 1908, and/or a narrative generator 2608.

In some examples, the ePCR template generator 2108 may be configured to generate ePCR templates from a set of rules that prescribe valid values for identified ePCR fields in ePCRs that document particular types of dispatched EMS events.

The rule set may be, for example, but not limited to, a complete call rule set such as, but not limited to, a Schematron rule set. "Schematron" refers to a particular rule-based language and international standard for XML document validation. The rule set, which may be a context sensitive rule set, may specify values for one or more first fields of the ePCR based on values in one or more second fields of the ePCR. An EMS agency may mandate that in order to complete and submit a generated ePCR, the ePCR must be validated according to the rule set. For example, when the user indicates to the ePCR application 160 that the ePCR is complete, the ePCR application 160 may validate the ePCR according to the rule set. In this manner, the ePCR application 160 may confirm that the field values conform to the rule set. The rule set may ensure that the generated ePCR is logical and/or complete.

Rather than just validating an already created ePCR, use of a template that applies the rule set during the creation of the ePCR may improve ePCR quality and provide more time for the end user to attend to patient care. As an example, the validation rule set may specify that a field value of "pregnant" for an ePCR field of "assessment" is invalid if a "gender" field indicates "male." As another example, if a "transport" field includes the value "no transport," the validation rule set may specify that a set of fields that describe the transport include the value "not applicable." The set of fields requiring "not applicable" may be large enough to occupy a significant amount of time if the user has to fill in one field at a time. This time may detract from time spent on patient care and/or on accurate completion of other ePCR fields that may significantly impact patient care, such as the narrative, medications provided, vital signs, etc. Therefore, it may be beneficial to provide a template that corresponds to a field value in a first ePCR field and automatically fills in one or more second fields as "not applicable" according to the context sensitive validation rules. For example, the administrator may create a "no transport template" that corresponds to the "no transport" field value of the "transport" field in the ePCR. When the end-user selects this template, the ePCR application 160 applies the template to the ePCR being generated for the patient encounter. The "no transport template" may enter the "not applicable" value into all of the appropriate ePCR fields according to the rule set.

In these examples, the ePCR template generator 2108 may be configured to receive requests (e.g., from the administrator 134 via the ePCR user interface 180) to auto-generate ePCR templates that include an identifier of an electronic version of the set of rules. This electronic version may be a set of complete call rules generated by a user (e.g., the user 134), text data subscribing to a pre-defined format, and/or other input. In these examples, at least some rules of the set of rules may include an identifier of an ePCR field (e.g., a name) and a value (e.g., a field entry) that must be stored in the ePCR field according to the complete call rules. Satisfaction of the complete call rules may be required in order for the ePCR to be closed and completed as documenting a particular type of dispatched EMS event. In some examples, in response to receiving a request to generate rule-based ePCRs, the ePCR template generator 2108 is configured to parse the request, identify rules that require particular values for particular fields, and generate a new ePCR template with a set of pre-determined values for a subset of ePCR fields that correspond to the values and fields required by the rules. In an implementation, the administrator may select the subset of ePCR fillable fields. Alternatively, the ePCR application 160 may automatically select the subset of ePCR fillable fields based on, for example, the type of template.

Referring again to FIG. 4A, in some examples, the overlap populator 2308 may be configured to process requests to populate a target ePCR field for which two or more ePCR templates each provide a value for the target ePCR field. The value from each of the ePCR templates may be the same as or may be different than one or more of the other ePCR templates. In these examples, the overlap populator 2308 may receive requests to populate target ePCR fields that include an identifier of the target ePCR field and two or more identifiers of the two or more ePCR templates that each specify a pre-determined value for the target ePCR field. In these examples, the overlap populator 2308 may be configured to parse the request, evaluate one or more rules from a set of pre-determined selection rules to identify one or more pre-determined values from one of the two or more templates to store in the target ePCR field, and store the one or more identified values in the target ePCR field. In some examples, the set of pre-determined selection rules define a process in which one or more pre-determined values are stored within the target ePCR field. In these examples, the set of pre-determined selection rules first require that the target ePCR field be filled with a pre-determined value specified for the target ePCR field in the first ePCR template of the two or more ePCR templates.

The next action required by the pre-determined selection rules may depend on the target ePCR field's type. More specially, where the target ePCR field is a single-use field (i.e., a field that may store only one value at a time), the set of pre-determined selection rules may require that pre-determined values specified for the target ePCR field in ePCR templates subsequent to the first ePCR template be skipped. For example, the ePCR application 160 may enter a value into the single use field from the first applied template and not enter values from subsequent templates. However, where the target ePCR field is a multi-select field or a text field (i.e., a field that may store multiple values at a time), the set of pre-determined selection rules may require that pre-determined values specified for the target ePCR field in ePCR templates subsequent to the first ePCR template be added to the target ePCR field. For example, the ePCR application 160 may enter values from each of the applied templates into the multi-select field.

It should be noted that other rules may be included or excluded from the set of pre-determined selection rules and that the examples described herein are not limited to a particular set of pre-determined selection rules. For instance, in some examples, the overlap populator 2308 may be configured to provide a prompt, via the user interface, requesting that the user select a preferred value for overlapping single-use fields, rather than simply skip values in subsequent ePCR templates. In some examples, some ePCR templates may be designated as priority or overwrite templates. In these examples, the values of the priority templates are stored in single-use fields regardless of the order of ePCR template selection. Alternatively or additionally, certain fields within an ePCR template, rather than the entire ePCR template, may be designated as priority fields, in which case their values are stored in the corresponding ePCR form field, regardless of the order of ePCR template selection.

Referring further to FIG. 4A, in some examples, the ePCR application 160 may include the ePCR type identifier 1708, the ePCR template identifier 1908, and/or the narrative generator 2608.

The ePCR type identifier 1708 may be configured to monitor an ePCR during editing to detect whether the fields of the ePCR indicate that the ePCR is of a type that is associated with one or more ePCR templates. In these examples, the ePCR type identifier 1708 may monitor a set of trigger fields of the ePCR being generated for one or more sets of trigger values. Combinations of these trigger fields and values may indicate whether the ePCR is of a particular type. For instance, a memory (e.g., the memory 321, 421, and/or 521 of FIG. 20) may store one or more cross-references that associate each set of the one or more sets of trigger values with one or more ePCR templates. Alternatively or additionally, the memory may store a heuristic model with rules that associate trigger values with ePCR templates. In some examples, the ePCR type identifier 1708 may be configured to search the one or more cross-references for an association between values filled into trigger fields and one or more ePCR templates as an ePCR is populated. Where the ePCR type identifier 1708 detects one or more associations, the ePCR type identifier 1708 may notify subscribed processes (e.g., the ePCR application 160) of the one or more associations. Other structures and methods for associating values of trigger fields with ePCR templates will be apparent to those skilled in the art with the benefit of this disclosure.

The ePCR template identifier 1908 may be configured to process requests to identify ePCR templates that are complementary to other ePCR templates. In these examples, the ePCR template identifier 1908 may receive requests to identify complementary ePCR templates based on an identifier of a selected ePCR template. In these examples, the ePCR template identifier parses the request, accesses the identifier of the selected ePCR template, and searches a cross-reference for an association between the identifier of the selected ePCR template and one or more identifiers of one or more complementary ePCR templates. This cross-reference may be stored in a memory (e.g., the memory 421). Where the ePCR template identifier 1908 detects one or more associations, the ePCR template identifier 1908 may notify the requesting process (e.g., the ePCR application 160) of the one or more associations.

The narrative generator 2608 may be configured to process requests to populate target ePCR fields with narrative text generated from values stored in both ePCR template fields and ePCR fields. More specifically, in these examples, the narrative generator 2608 receives requests to populate target ePCR fields that include an identifier of the target ePCR field and a string of characters that includes literals, which specify static text to be included in a narrative field, and variables to be replaced in a narrative field with values stored in identified ePCR fields. In these examples, the narrative generator is configured to parse the requests, identify the literals and variables, identify the ePCR fields storing values to replace the variables, retrieve the values from the identified ePCR fields, and store, in the target ePCR field, narrative text including the literals and the variables as replaced by the values of the identified ePCR fields. Narrative fields are described further below with reference to FIG. 10.

Figure 20:
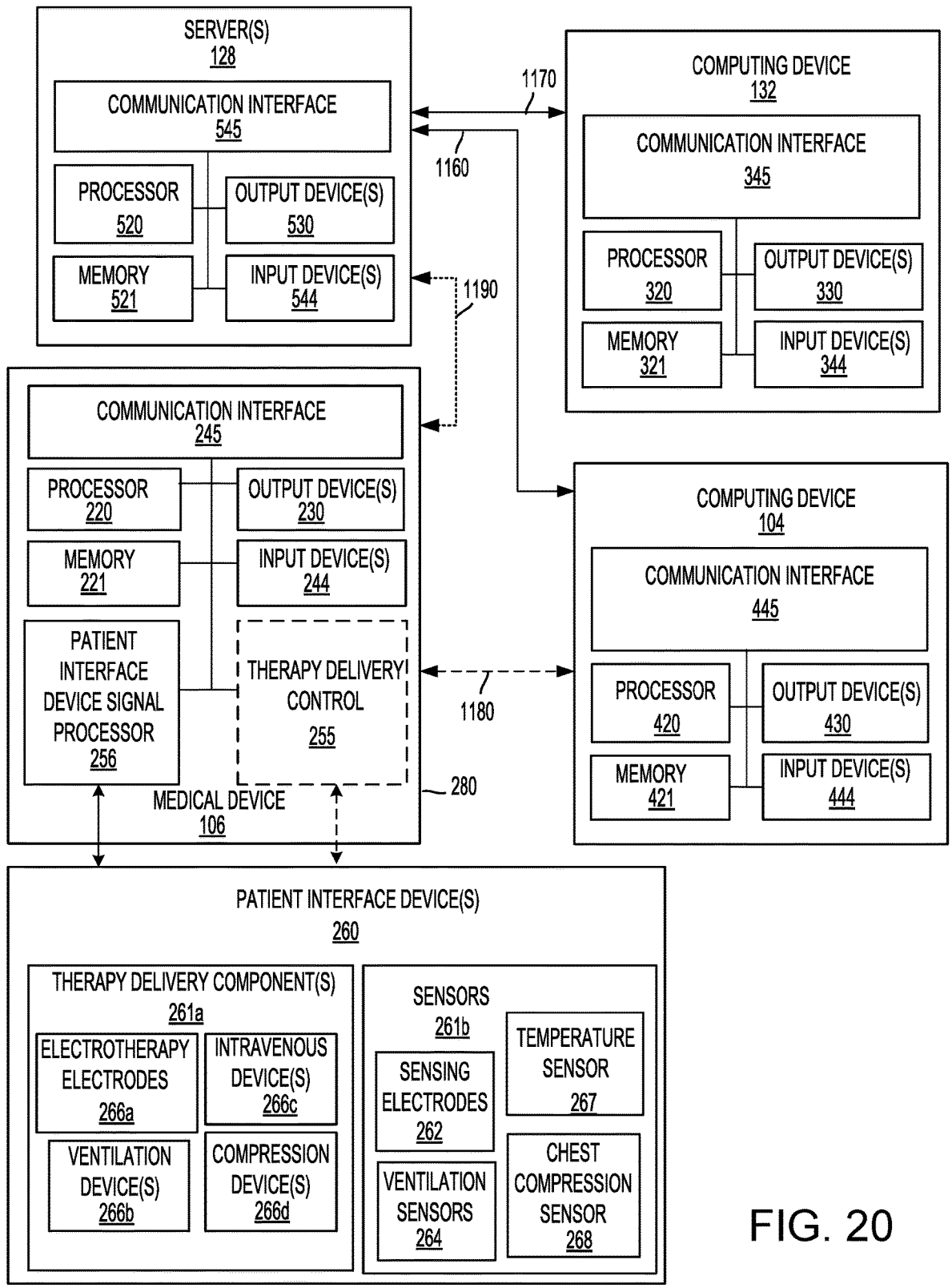
FIG. 20 is a schematic block diagram of examples computing and medical device components with which examples of the present disclosure may be implemented.

Referring again to FIG. 4A, the ePCR data store 130 may be implemented by, for example, a database (e.g., a relational database) and stored on a non-transitory storage medium. In an implementation, the data store 130 includes a plurality of ePCR templates 1508. In an implementation, the computing device 104 may locally store one or more of the plurality of the ePCR templates 1508, for example, in the memory 421 as shown in FIG. 20. In some examples, the ePCR data store 130 (or a copy thereof) may be included in the administrative environment (e.g., on the computing device 132) and/or in the mobile environment 101 (e.g., one the computing device 104).

In at least one example, the ePCR data store 130 is organized into a set of relational database tables that includes an ePCR table and an ePCR fields table. In this example, the ePCR table includes rows of data that are each descriptive of an ePCR that documents a dispatched EMS event in the ePCR database. Thus, each row in the ePCR table may include fields configured to store a unique identifier of the ePCR, a timestamp indicating when the ePCR was created, and metadata descriptive of the EMS event documented by the ePCR (e.g., patient identification information that uniquely identifies the patient, healthcare providers involved in the EMS event, reason(s) the ePCR was closed ended and outcome, unique identifiers of medical devices and supplies used in the resolving the EMS event, overall issues encountered during execution of the intervention, and/or a type of dispatched EMS event associated with the ePCR).

Continuing with this example, the ePCR fields table includes rows of data that are each descriptive of a field stored within an ePCR. Thus, each row in the ePCR fields table includes fields configured to store a unique identifier of the ePCR to which the field belongs, a field that uniquely identifies the field among the fields associated with the ePCR, a date/time stamp indicating when the field was populated with a value, a unique identifier of the source of the value (e.g., a particular medical device, a particular computing device, or a particular ePCR template), a field that identifies a field type (e.g., single use, multi-select, or text) for the field, and a field that identifies (via a type identifier or textual information) one or more values associated with the field. Notably, each ePCR may have a large quantity of fields that each require entry of a specific data type. For instance, some example ePCRs may have as 100 fields, 200, fields, 400 fields, 600 fields, or more. As discussed above, this quantity of fields may be mandated and, therefore, it is important that each ePCR be complete. Therefore, in some examples the ePCR data store 130 and/or other components, such as the ePCR application, are configured to prevent modification/deletion of ePCR fields by a user of the ePCR application.

In some examples, the ePCR data store 130 also houses ePCR templates comprising ePCR fields. In some examples, these data structures are the same as or highly analogous to the ePCR data structures described above. For instance, the ePCR data store 130 may include a table for ePCR templates and a table for ePCR template fields that have the same fields and metadata as the ePCRs themselves. Notably, each ePCR template stored in the ePCR data store (regardless of its physical structure) specifies a plurality of pre-determined values for a subset of the plurality of ePCR fields within an ePCR. These pre-determined values may be prescribed by an administrator (e.g., the administrator 134) and may be specific to one or more EMS agencies. In addition, it should be noted that in some instances the pre-determined values in fields of a particular template may indicate that these fields are not applicable to a particular EMS event for which the user may select the particular template to apply to an open ePCR. In an implementation, the administrator may select the subset of ePCR fillable fields. Alternatively, the ePCR application 160 may automatically select the subset of ePCR fillable fields based on, for example, the type of template.

In an implementation, the ePCR application 160 may not display some ePCR fields in the ePCR template edit screens. These fields may be incompatible with entries determined prior to dispatch for an emergency event. Examples of these fields may include crew member id, facility code, vehicle id, patient identification, among others.

Examples of ePCR templates stored in the ePCR data store 130 may include, but are not limited to, a basic emergency call template, a cardiac arrest template, a trauma template, a cancelled call template, a dialysis template, a narrative template, a "no cardiac arrest" template, a "no trauma" template, a STEMI template, a demographics template, a chest pain template, and/or combinations thereof. The ePCR templates stored in the ePCR data store 130 may further include medical responses or response protocols (e.g., a chest pain intervention template) for a condition covered by one of the ePCR templates listed above. The narrative template may include headings for various formats. For examples, the headings may include subjective, objective, assessment, and plan sections (e.g., a SOAP format). An example of entries in a dialysis template is discussed above with regard to Tables 1 and 2. An example of entries in a "no cardiac arrest" template is shown below in Table 3.

TABLE 3

| ePCR Field-cardiac arrest section | Field value for "No Cardiac Arrest" Template |
| --- | --- |
| Cardiac Arrest | Not Applicable |
| Time of Cardiac Arrest | Not Applicable |
| Arrest Etiology | Not Applicable |
| Resuscitation Attempted | Not Applicable |
| CPR provided prior to EMS | Not Applicable |
| Arrest witnessed by | Not Applicable |
| $1^{st}$ Rhythm | Not Applicable |
| Spontaneous circulation | Not Applicable |
| Resuscitation Description | Not Applicable |
| Rhythm at destination | Not Applicable |
| End of EMS Cardiac Arrest | Not Applicable |

As the ePCR templates discussed herein are aligned with types of dispatched EMS events, they are independent of patient identity. The ePCR templates are customized to a category of dispatched EMS event and are applicable to a patient record for any patient with a condition or in a situation that falls within the category of medical and/or dispatch event covered by the template. However, since the total number of fields in the ePCR and the acceptable set of responses for each field in the ePCR are immutable by the caregiver generating the ePCR, the applied templates do not customize these features of the ePCR. For example, suppose that the ePCR contains fields that apply to cardiac arrest and to trauma and the caregiver is generating the ePCR for a trauma patient. The ePCR application 160 may enable the caregiver to apply a template that enters "not applicable" or the equivalent in the cardiac arrest related fields. However, in this example, the ePCR application 160 does not enable the user to eliminate the cardiac arrest related fields from the generated ePCR. As another example, the ePCR format may mandate fields for a collection of particular vital signs or physiological signals. In this example, the ePCR application 160 does not enable the user to eliminate particular ones of these fields based on personal treatment preferences or based on a patient's particular medical history.

In some examples, the ePCR data store 130 stores a variety of cross-references to enable the features described herein. For instance, the ePCR data store 130 may store a cross-reference that associates ePCR templates with one another. The ePCR data store 130 may store another cross-reference that stores associations between ePCR templates and trigger fields. The ePCR data store 130 may also store historical data, such as an historical log of ePCR template applications. This log may include fields that identify the user who requested the ePCR template application, a date/time stamp of the request and the application, and the ePCR fields affected. This information may be used to establish user preferences for particular ePCR templates. In some examples, the ePCR application is configured to provide a screen with controls to display the data included in the historical log. In some implementations, the ePCR data store 130 is configured to store ePCR data from various source devices, such as the computing device 104.

The ePCR data store 130 may be organized according to a variety of physical and/or logical structures. In at least one example, the ePCR data store 130 is implemented within a relational database having a highly normalized schema and accessible via a structured query language (SQL) engine, such as ORACLE or SQL-SERVER. In addition, although the description provided above illustrates the ePCR data store 130 as a relational database, the examples described herein are not limited to that particular physical form. Other databases may include flat files maintained by an operating system and including serialized, proprietary data structures, hierarchical database, xml files, document-oriented databases and the like. Thus, the ePCR data store 130 as described herein is not limited to a particular implementation.

The servers 128, shown for example in FIG. 4A, may include one or more physical and/or virtual servers configured to implement the ePCR data store 130. In some examples, the servers 128 may exchange data with remote devices in the mobile environment 101 and/or the administration environment 103 via an application program interface (API) that is configured to receive, process, and respond to commands issued by processes implemented by the remote devices, such as the ePCR application 160 described herein. The API may be implemented using a variety of interoperability standards and architectural styles. For instance, in one example, the API is a web services interface implemented using a representational state transfer (REST)

architectural style. In this example, the ePCR API communicates with a client process using Hypertext Transfer Protocol (HTTP) along with JavaScript Object Notation and/or extensible markup language. In some examples, portions of the HTTP communications may be encrypted to increase security. Alternatively or additionally, in some examples, the API is implemented as a .NET web API that responses to HTTP posts to particular uniform resource locators with data descriptive of ePCR data. Alternatively or additionally, in some examples, the API is implemented using simple file transfer protocol commands and/or a proprietary application protocol accessible via a transmission control protocol socket. Thus, API as described herein is not limited to a particular implementation.

In some examples, the API includes a plurality of endpoints to enable reliable system performance. For instance, in at least one example, the API includes a one or more first endpoints to receive and process requests for data previously stored in the ePCR data store 130 and one or more second endpoints to receive and process requests to store new ePCR data within the ePCR data store 130. This configuration may ensure that requests for data already stored in the ePCR data store 130 may be quickly serviced, and may be necessary because requests to upload ePCRs, parse the ePCRs, and store the resulting ePCR data in the ePCR data store 130 may require more processing time and resources. The types of information parsed from the ePCR data and stored in the ePCR data store 130 may include, for example, CPR compression data, patient physiologic parameters, documented events, and the like.

In various implementations, the computing device 104 may share information received from the server(s) 128 and/or the administrative environment 103 with the other devices in the mobile environment. For example, the computing device 104 may receive information from the one or more application servers 128 and may display such information itself, and/or share such information with the devices 106, and/or the navigation or dispatch device 195. For example, if medical device 106 takes an ECG reading of the patient 116, or if the medical device 106 administers a treatment (such as medication, chest compression, ventilation, defibrillation shock, etc.), information descriptive of the ECG and/or the treatment may be shared, via computing device 104 or directly, with other devices and/or for storage in a patient record maintained therein. In another example, the computing device 104 may be configured to receive patient information, such as medical records, known medical conditions, and biographical information, and to share this information with the devices 106. This biographical information may be inserted into a patient record (e.g., an ePCR) being maintained and/or generated at the computing device 104.

Data from the computing device 104 (and, when present, data from the other devices that may be communicably coupled with the computing device 104) may be received by the one or more servers 128 and stored in the ePCR data store 130. The computing devices 132 and/or 142 may also access the stored information.

When the computing device 104 receives updated information from the other devices to which it is communicably coupled, and/or via input from the healthcare provider 114, the computing device 104 may send the updated information to the one or more servers 128. Hence, information from one or more devices (e.g. the medical device 106, the navigation or dispatch device 195) may be stored locally at the computing device 104 (e.g., in the memory 421) and/or at the server(s) 128 (e.g., in the memory 521 and/or in the ePCR database 130).

In an implementation, the system 100 may include a computing device 142 associated with a third party 124. For example, the third party 124 may be an emergency room nurse monitoring and/or preparing for ambulance arrivals, an emergency room physician, and/or a medical director, doctor, or other caregiver on scene, at home, or at a medical facility. The third party 124 may access information similar to information displayed by the computing device 104 and/or 132 by requesting the information via the computing device 142. For example, the computing device 142 may access a web interface and/or thin client web browser application which requests the information over the network 120 from the one or more servers 128. The one or more servers 128 may query the ePCR data store 130 for the information, and return data captured by the ePCR application 160 via the ePCR user interface 180. For example, the one or more servers 128 may provide all or a portion of one or more generated ePCRs to the computing device 142. In an implementation, the ePCR application 160 may provide information descriptive of one or more screens of the ePCR user interface 180 to the computing device 142 that look the same as or similar to screens currently provided by the ePCR application 160 to the healthcare provider 114 by the computing device 104, according to examples of the present disclosure. In such an implementation, the computing device 142 may provide the ePCR information in real-time to the computing device 142 for use by the third party 124.

The ePCR data store 130 may securely store the information received from one or more computing devices 104 for longer periods of time to permit later use of the information. For example, the computing device 104 may receive patient-identifying information such as name, address, and/or social security number via user input directly into the computing device 104, and then may convey some or all of the patient-identifying information to the server(s) 128 to query the ePCR data store 130 for past records involving the patient 116. In an implementation, the computing device 104 may convey some or all of the patient-identifying information to other server(s) via the network 120 to access patient records and/or information from various databases such as those provided by a medical facility, insurance company, medical billing service, financial record service, and/or a health information exchange. In other examples, the computing device 104 may be configured to receive information in other ways, including without limitation wired or wireless communication and/or messaging.

The one or more servers 128 and/or other server(s) accessed via the network 120 may then forward any such records or portions of such records back to the computing device 104 (e.g. for display in a patient charting screen or past medical history screen) to assist the healthcare provider 114 with the current emergency. Similarly, such past EMS encounter record information may also be accessed by the user, according to examples of the present disclosure. The user 134 (e.g., a system administrator) may access and/or monitor the data in ePCR data store 130 and/or modify the instructions of the servers 128 via administration workstation 132, which may be communicably coupled to the servers 128, according to examples of the present disclosure.

In an implementation, the computing device 104 and/or the server(s) 128 may transmit, receive, and/or exchange data with the administration environment 103. As shown in FIG. 4A, the administration environment 103 may include a computing device 132 associated with an administrator 134 or another user. In an implementation, the computing device 132 may provide the ePCR user interface 180.

In some examples, ePCR templates are created by the administrator 134 on the computing device 132 using the ePCR application 160. The administrator 134 may customize the field entries for the ePCR template based on specific needs, requirements, and/or preferences of one or more agencies associated with the administrator. In an implementation, the ePCR application 160 may require an entry of administrator credentials to enable the ePCR template creation. Once the ePCR template is created, the ePCR application 160 may electronically distribute the ePCR template to other computing devices (e.g., the computing device 104). Once the ePCR templates are available at the other computing devices, the ePCR application 160 may provide the end user (e.g., the healthcare provider 114) with the option to select from some or all of the ePCR templates created by the administrator 134.

The ePCR template (e.g., a quick fill feature) capability may allow the user (such as the healthcare provider 114 of FIG. 4A) to document a complete ePCR in a shorter amount of time by allowing them to apply an ePCR template that quickly fills in values that are the same on every call (dispatched EMS event) of that type. The ePCR templates may be layered on top of one another to add in more flexibility to this useful feature. This tool may provide advantages for EMS calls that are cancelled or calls for which the patient refuses service. In both of these cases, the information that the EMS professional may be required to collect may be daunting at least in part because of the large number of fields required by a state or other jurisdiction and/or fields required for compatibility with a database standard (e.g., NEMSIS, HL7, etc.). In some cases, the answers to these questions may be the same for most or every call of this type and so, to the documenter, the task may feel tedious and like a waste of valuable time. The tool described herein may allow the administrators to set up templates that will work based on the agency's specific reporting requirements and which may differ from reporting requirements for another agency and/or for another jurisdiction or region.

Figure 4B:
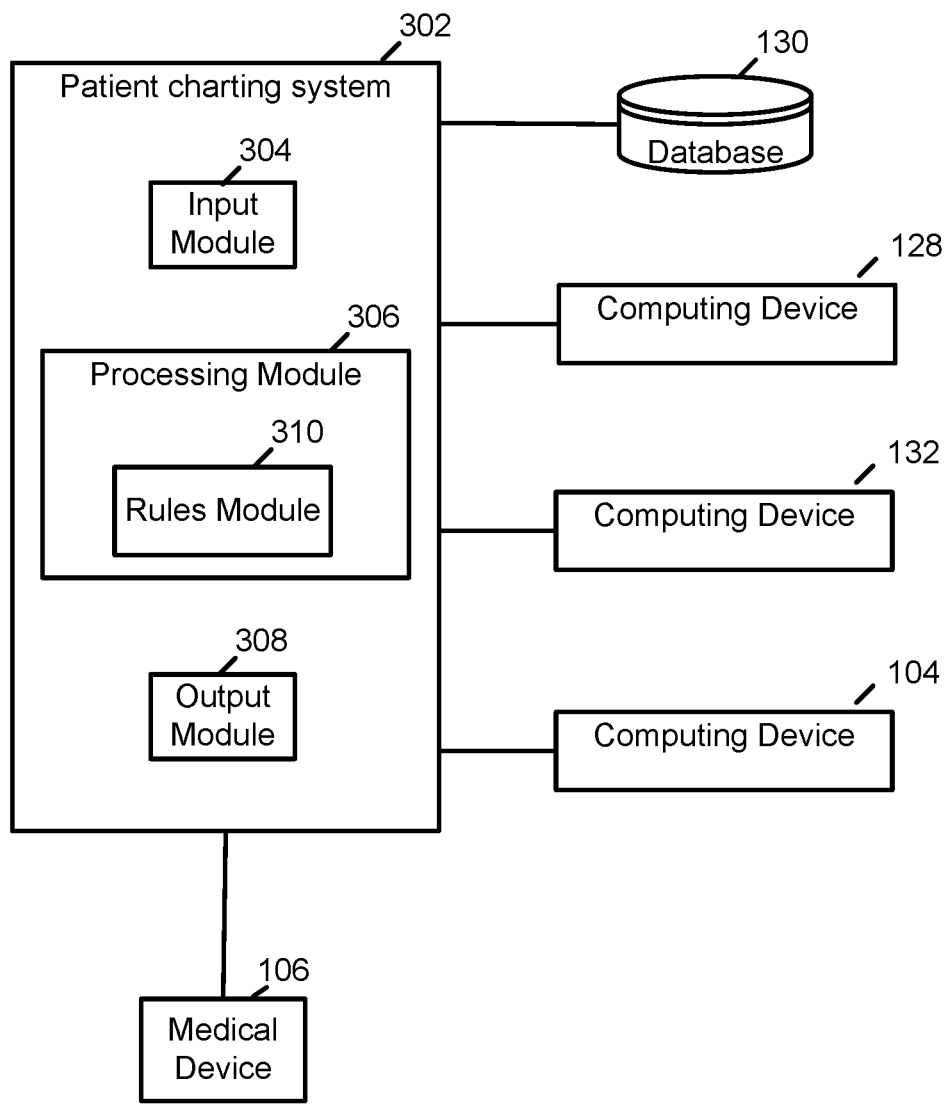

Referring to FIG. 4B a functional block diagram illustrating a patient charting system 302 in accordance with one example of the present disclosure is shown. The patient charting system 302 may implement some or all of the functions of the ePCR application 160 and the ePCR user interface 180. As shown in FIG. 4B, the patient charting system 302 may be one or a combination of hardware, software, an application, and one or more devices (e.g. computing device 104, computing device 132, computing device 128 (e.g., server(s)), and medical device 106 according to some examples of the present disclosure. Features, functionality, and capabilities described herein with respect to the devices 104, 132, 128, and 106 also may apply to patient charting system 302 and other systems described herein. Patient charting system 302 may reside on a client, such as an end-user device (e.g., computing device 104, computing device 132 and/or medical device 106), and/or a server (e.g., server(s) 128), such as a web server. One or more portions of patient charting system 302 may reside on different devices. One or more portions of the patient charting system 302 may reside at a network centric location. According to some examples, analysis and approval of resource references including patient charting system 302 may be implemented as part of a cloud computing environment. For example, patient charting system 302 may be distributed to various clients and servers through a cloud computer environment. As another example, patient charting system 302 may be updated at the network centric location and then distributed to various clients and servers. Patient charting system 302 may comprise one or more processors.

In some examples, patient charting system 302 may include input module 304, processing module 306, and output module 308. Processing module 306 may include a rules module 310. Input module 304, processing module 306, and output module 308 may reside on different computers and/or devices. For example, the input module 304 may reside on a client device of an emergency medical service healthcare provider. Processing module 306 may reside at a server. Portions of a module may reside on different computers as well. For example, some portion of output module 308 may reside on a server, and some portion of output module 308 may reside on a client device. As used herein, the term "module," in addition to its ordinary meaning, refers to hardware, software, firmware, and/or a combination of two or more of hardware, software, and firmware. In some cases, a module that is part of a system is a device that performs the described functionality. In other cases, a module that is part of a system is a set of instructions, and/or a memory with those instructions, that, when executed by a processor, performs the described functionality.

Input module 304 may receive charting data, which is also referred to herein as ePCR data. The input module 304 may receive the charting data via one or more of the devices 104, 132, 128, 106 and/or via the database 130. Charting data may include, but is not limited to, patient information (e.g., name, age, gender, weight, and/or other identification and/or demographic information), medical event specific information (e.g., type of service requested, disposition), and/or clinical information (e.g., patient assessment, patient blood pressure). Charting data may be received via various mechanisms, including, but not limited to, touch-screen, voice recognition, and scanner. For example, a patient may say his/her name and input module 304 may capture the patient name and save it in the patient charting system. Input module 304 may be coupled to a scanner through which patient's driver license may be scanned and relevant information about the patient, such as name, address, age, may be saved in the patient charting system. A caregiver or other healthcare provider may dictate data or findings when examining the patient. Such dictation may be captured by input module 304 and saved in the patient charting system 302, according to some examples. As used herein, the phrases "medical situation" and "medical event," in addition to their ordinary meanings, may refer to and may include situations and/or events in which medical attention is called for, in which a patient experiences a medical problem, or in which a patient has treatment or care, and includes, for example, emergent situations. For example, and without limitation, a medical event may begin when a patient experiences medical symptoms and/or a call is made to emergency services (e.g. emergency medical services) requesting attention. The medical event may end when the patient has been evaluated, treated, transported, and/or released and/or when the patient dies. In an implementation, the medical event may be a dispatched event and may end when and if the dispatched call is canceled. A medical event or situation may include various events within the medical event, including for example emergency transport. As used herein, "clinical data" is used in its broadest sense to refer to data relevant in treatment and/or diagnosis of a patient, and may include both physiological data and vital signs, for example. Non-clinical data, or data of a non-clinical type, is data that is not clinical data; for example, data of a non-clinical type includes biographical data such as name, address, patient identification number, dispatched crew information, and/or the like.

Processing module 306 may obtain additional data that is associated with at least some of the received charting data. Processing module 306 may determine one or more sources for data retrieval. For example, based on the received patient address, processing module 306 may retrieve patient medication information from a pharmacy that is close to the patient address. Processing module 306 may retrieve additional data using health data exchange standards, such as state-wide health data exchange standards, regional health data exchange standard, HL7 message standards, and NCPDP script standards. Processing module 306 may retrieve additional data using communication protocols over network (e.g., via network 120) from a remote database. The communication protocols may include, but are not limited to, RESTful and/or other Web Services. Processing module 306 may retrieve additional data within the same organization or network of which it is a part, or from at least one other organization or network or third party source. Processing module 306 may retrieve additional data from various providers, including, but not limited to, hospitals, clinics, doctors' offices, and pharmacies.

In some examples, processing module 306 may include the rules module 310. The rules module 310 may be coupled to a data source that stores rule sets that may govern the ePCR form of the patient charting system 302. For example, the rule set may include a complete call rule set. The data source may be a file, a database, and/or the like. The processing module 306 may also be a software module that applies the rule set to a previously generated ePCR or open ePCR of patient charting system 302. For example, if received charting data (e.g., input by a user of patient charting system 302) indicates that patient's gender is male, then processing module 306 may adjust a generated ePCR and/or control an open ePCR such that a data field relating to current pregnancy is grayed out or otherwise deactivated, and/or defaulted as "No."

Output module 308 may provide charting data and/or additional data to one or more of the devices 104, 132, 128, 106 and/or the database 130. In some examples, charting data and/or additional data may be sent over a network.

Patient charting system 302 may be a web application. A portion of the output module 308 may be a web page that may be displayed on, for example, the computing devices 104 and/or 132 and/or on the medical device 106. Patient charting system 302 may be implemented based on a client-server architecture. A portion of the patient charting system 302, for example the output module 308 or a portion of the output module 308 may be implemented as, for example, an Android™ application, an Apple® application, or another operating system based application operable on a smart phone, tablet, or other mobile device. Output module 308 may communicate with medical device 106 via specific protocols.

Figure 5:
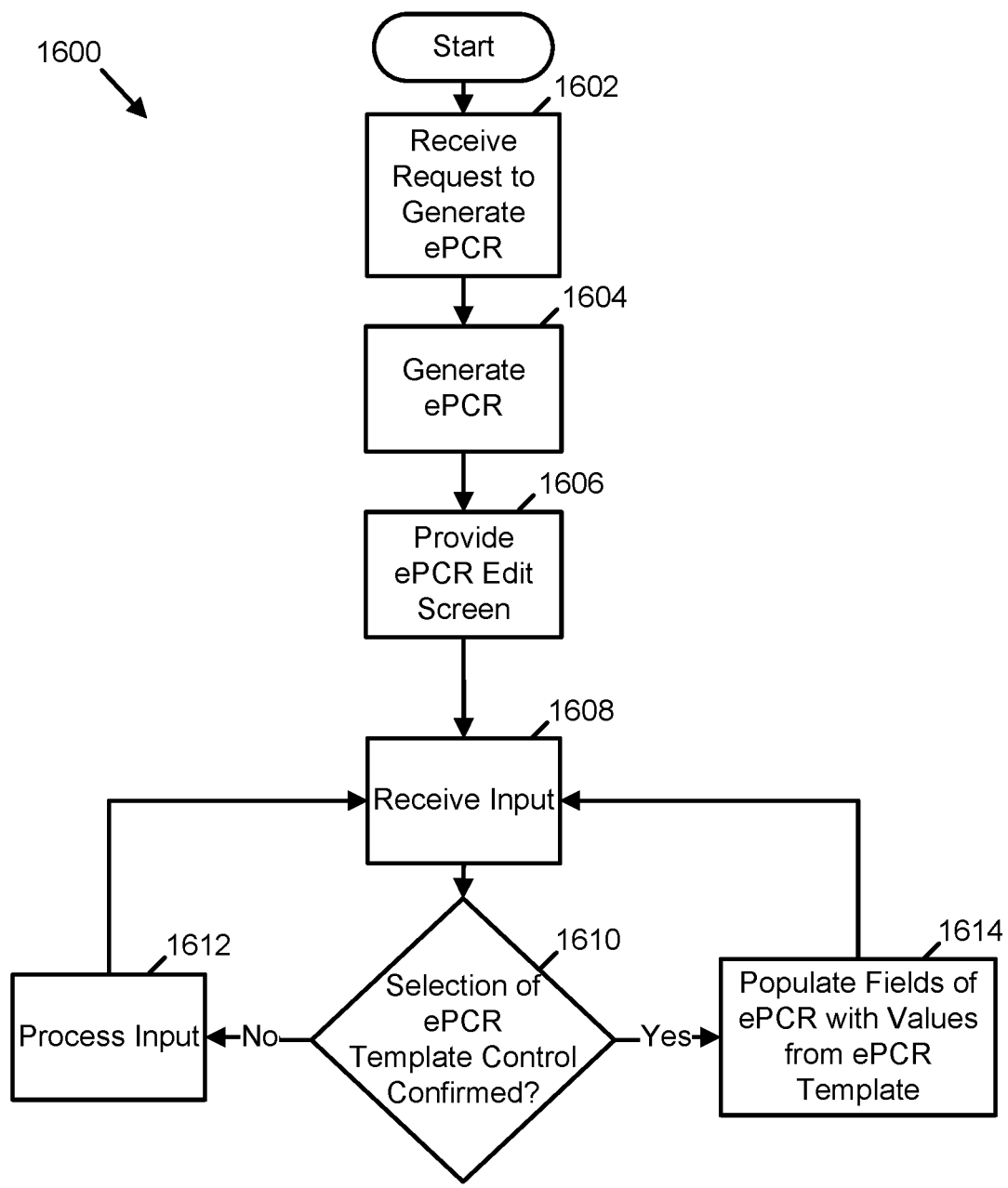
FIG. 5 is a flow diagram illustrating a process of suggesting ePCR templates for application in accordance with at least one example disclosed herein.

Referring to FIG. 5, a block diagram of an example of an ePCR generation process is shown. The ePCR generation process 1600, which includes the application of templates to the open ePCR, may decrease both errors in and time required to complete the ePCR. Due to the large number of required fields in an ePCR, in some cases, EMS crews may miss fields or enter incorrect data in a rush to finish the ePCR within time constraints of emergency responses and/or may postpone completion of the ePCR until after the emergency response. Incomplete, inaccurate, and/or delayed ePCRs may negatively impact continuity of care and care following the EMS response and therefore have a detrimental effect on patient outcomes. As an example, failure to document patient complaints or symptoms and/or administered drugs may result in the hospital providing care and/or medications contra-indicated by the EMS events.

As an example, the ePCR application 160 may be configured to execute the ePCR generation process 1600. As shown in FIG. 5, the ePCR generation process 1600 starts with an ePCR application (e.g., the ePCR application 160 of FIG. 4A) receiving a request to generate an ePCR. For example, the ePCR application may receive input specifying the request from a user (e.g., the healthcare provider 114 of FIG. 4A) via a user interface (e.g., the ePCR user interface 180 of FIG. 4A). In some examples, the ePCR application receives the input via selection of the ePCR generation control 199 within the initiation screen 198 as illustrated in FIG. 1A.

In response to receiving 1602 the request to generate the ePCR, the ePCR application may generate 1604 (e.g., open) a new ePCR. For example, the ePCR application may insert a new ePCR record and new ePCR field records associated with the new ePCR record in memory (e.g., the memory 321, 421, and/or 521 as shown in FIG. 20). In some examples, when generating 1604 the new ePCR, the ePCR application inserts a default value within each or some of the new ePCR field records.

Next, the ePCR application may provide 1606, via the user interface, an ePCR edit screen, such as the ePCR edit screen 900 described above with reference to FIG. 1B. The ePCR application receives 1608 input via the ePCR user interface 180.

The ePCR application 160 may determine 1610 whether selection of an ePCR template control 1002 is confirmed via the input. For instance, the ePCR application 160 may determine whether the template request control 902 (e.g., the quick fill button of FIG. 1B) was selected by the user and/or whether an ePCR template control 1002 was selected by the user.

Figure 6:
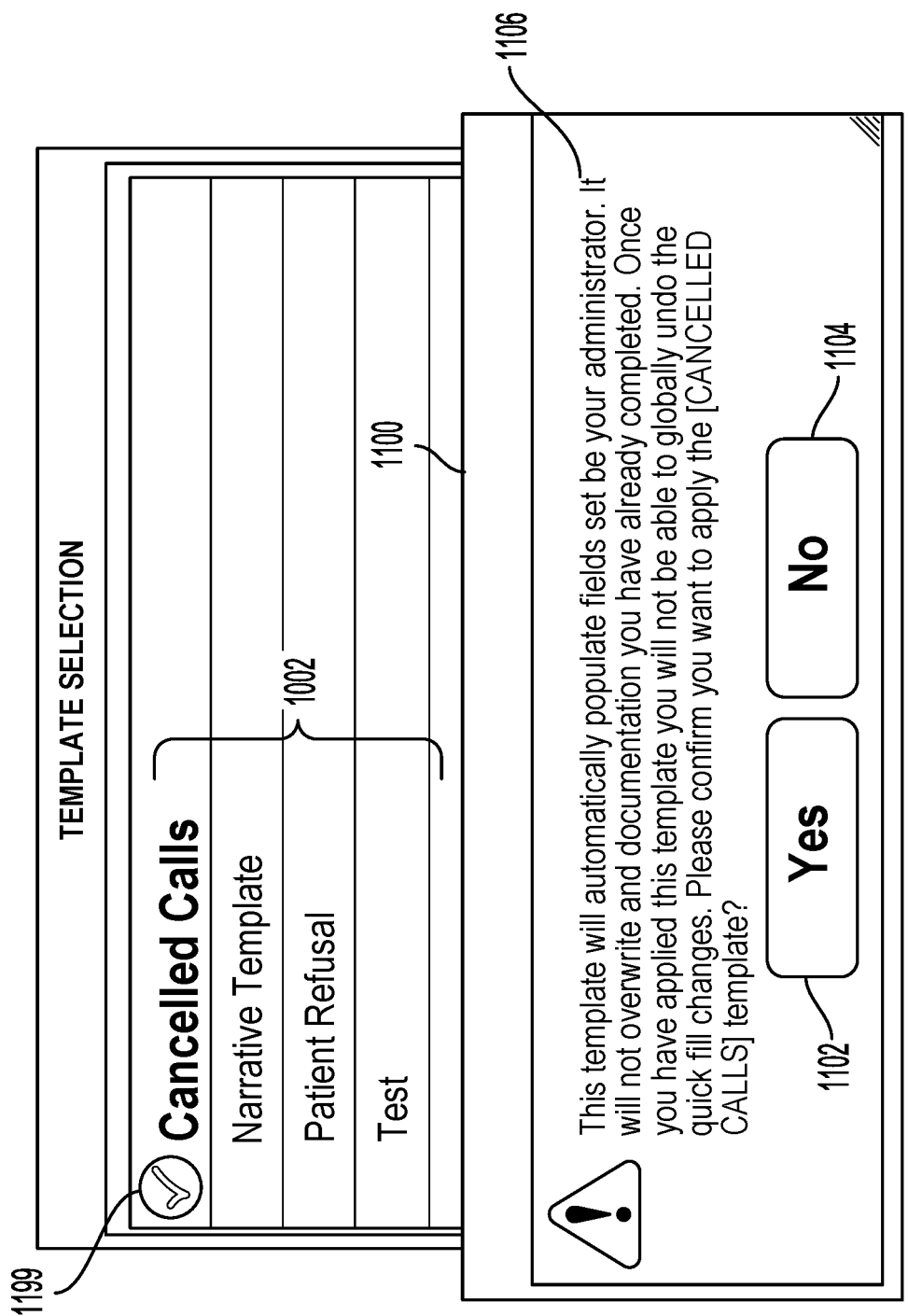
FIG. 6 is a view of a template selection window provided by an ePCR application in accordance with at least one example disclosed herein.

Referring to FIG. 6, in an implementation, in response to the selection of one of the ePCR template controls 1002, the ePCR application 160 may provide a warning screen 1100. In this example, the ePCR template control "cancelled calls" is selected as shown by a selection indicator 1199. The ePCR application 160 may confirm the selection of the ePCR template via the warning screen (e.g., via selection of a "yes" control 1102 of the warning screen 1100). The warning screen 1100, may indicate that a selected ePCR template (e.g., cancelled calls) associated with the selected ePCR template control from the controls 1002 is about to be applied and that such application cannot be reversed. As shown in FIG. 6, the warning screen 1100 may include warning text 1106, the "yes" control 1102, and a "no" control 1104. In response to receiving a selection of the "yes" control 1102, the ePCR application may apply the selected ePCR templates indicated by the selection indicator 1199. In response to receiving a selection of the "no" control 1104, the ePCR application may abort application of the selected ePCR template. In an implementation, the ePCR application may omit the warning screen 1100 and instead provide (for example, after application of the selected ePCR template) a screen including an undo control, that when selected, causes the ePCR application to de-populate the fields of the open ePCR populated by the ePCR template. Alternatively or additionally, in some examples, the ePCR application 160 may provide an additional notification screen, prior to population, that presents a preview of the ePCR as it will appear after population with values from the selected ePCR template. The ePCR application may render this screen with controls that highlight fields with values that will change due to the population. For instance, the ePCR application may present to-be-changed fields inside a control with a color, shading, and/or transparency that is different from controls presenting other fields. Depending on how many field values the ePCR template provides, application of the template may reduce the time required to complete the ePCR by a number of minutes.

Referring again to FIG. 5, where selection of the ePCR template control is confirmed, the ePCR application populates 1614 a subset of the ePCR fields in the ePCR in progress (e.g., the ePCR currently being edited by the user) with a set of pre-determined values specified for the ePCR fields in the selected ePCR template associated with the selected ePCR template control. In some examples, each ePCR template specifies values for ePCR fields by storing the values within ePCR template fields that correspond to the ePCR fields. For instance, according to these examples, an ePCR template may specify a value of "transported to hospital" for an ePCR field named "patient disposition" by storing the value of "transported to hospital" within an ePCR template field named "patient disposition."

In some examples, during population 1614, the ePCR application may change the user interface for the ePCR completion dynamically by applying a template that selectively shows and/or hides fields, thus allowing the user to focus only on fields that are required for the type of encounter they are on. For example, the user may document answers to a few questions and based on various criteria, such as a protocol, a call type, an outcome, etc., the user interface may dynamically adjust to hide unwanted or unneeded fields. The user interface may additionally adjust to hide one or more controls (e.g., primary controls 904 and the secondary controls 906 shown in FIG. 1B) that provide access to various field completion screens. The ePCR application 160 may determine the adjustments to the user interface on a call-by-call basis depending on the criteria. For example, on a call that sends an ambulance to a scene, but is cancelled prior to arrival, the end user may provide information indicating "cancelled-en route" in the call type. In response, the ePCR application 160 may automatically hide the patient information and demographics section of the PCR.

In an implementation, the ePCR application 160 may automatically populate various fields, either hidden or unhidden, based on the criteria and hide controls associated with populated fields in the user interface. This action may help to streamline the data entry process, as the user may not have to consider values for fields automatically populated 1614 by the ePCR application. After population 1614 is complete, the ePCR application may return to receiving 1608 input. As examples of acts for the hidden fields, the ePCR application 160 may automatically provide this information based on the dispatch and/or may fill in "not applicable" in the hidden fields. By auto-populating in this manner, the ePCR application 160 may allow the end user to complete the ePCR without encountering these fields. In an implementation, the ePCR application 160 may flag the user to complete and/or verify these fields at the end of a shift.

Where selection of the ePCR template control is not confirmed, the ePCR application processes 1612 the input and may return to receiving 1608 input. For example, where the user input specifies a value for an ePCR field without use of a template, the ePCR application stores the user input value in the ePCR field. If the user input requests closure of the ePCR edit screen, the ePCR application closes the ePCR edit screen and returns to the previously active screen.

Figure 7:
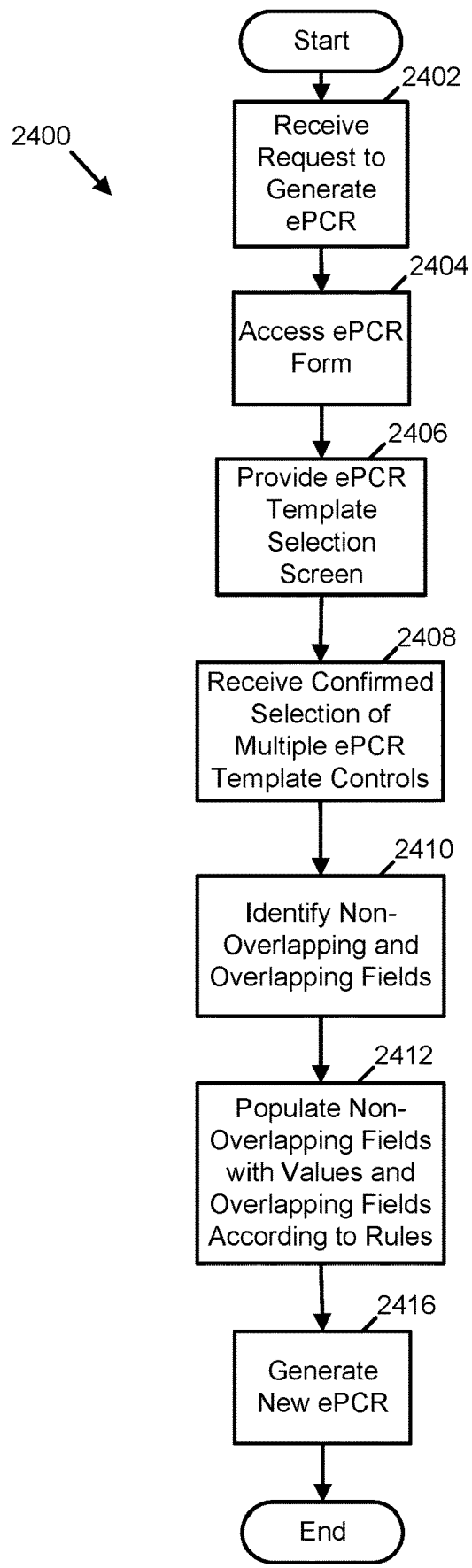
FIG. 7 is a flow diagram illustrating a template layering process in accordance with at least one example disclosed herein.

Referring to FIG. 7, a block diagram of an example of an ePCR template layering process is shown. In an implementation, the ePCR application 160 may execute the ePCR template layering process 2400. For example, an end user may select multiple ePCR templates and merge or layer these templates to more quickly fill out the ePCR in progress.

During a response to an emergency encounter, the caregiver or medic may recognize that several (i.e., more than one) template responses available for his/her agency are applicable to the emergency encounter. Additionally or alternatively, the medic may recognize that a number of fields do not apply to the emergency encounter but will require a "not applicable" or other equivalent value. The agency may provide multiple templates that cover the various inapplicable fields. Thus, depending on the emergency encounter and the available templates, the medic may select a combination of multiple templates to fill in fields relevant to the emergency encounter and/or may select a combination of multiple templates to fill in superfluous but required fields that are irrelevant to the emergency encounter.

A copy/merge capability of the ePCR application 160 may enable the ePCR application to merge the ePCR template data into the ePCR the end user is actively working on. In an implementation, the copy/merge functionality may provide an ability to combine information from a first ePCR form, for example, an ePCR template, with information from a second ePCR form, for example the open ePCR, and provide the combined information in the second ePCR form. During the copy/merge operation, the ePCR application 160 may copy a value for a particular field from the first ePCR form and enter that value into the same particular field of the second ePCR form. For example, the particular field may be "DispatchedComplaint." The field value for this field in the first ePCR may be "Palliative Care." The copy/merge operation would copy the value of "Palliative Care" from the "DispatchedComplaint" field of the first ePCR form and enter this value into the "DispatchedComplaint" field of the second ePCR form. In some instances, however, the second ePCR form may have one or more fields already populated with values prior to the copy/merge operation. Therefore, the copy/merge operation allows the ePCR application 160 to combine values from the first ePCR form with those already populated in the second ePCR form according to combination, or merge, rules designed to protect the already populated fields of the second ePCR form from unintentional and/or erroneous overwrite operations. In an implementation, the copy/merge rules may be referred to as layering rules as these rules guide the combining operation for multiple values for a particular field, for example, as derived from multiple templates applied to the open ePCR. Rules may include, for example but not limited to, disallowing overwrite operations for single use fields, adding one or more values to a multi-use field, and/or always overwrite. The rules for the copy/merge may be universal for the entire ePCR or may be field-by-field rules. In the field-by-field rules, each field may correspond to a rule for the copy/merge function. Examples of the rules and the copy/merge functionality are discussed with regard to the various implementations discussed herein.

In an implementation, the template layering process does not overwrite pre-existing ePCR data for any field. The copy/merge operation executed by the ePCR template layering process may include anything that was previously documented in the ePCR in progress by a medic or other healthcare provider to ensure that no data is lost. Alternatively, in an implementation, the ePCR application 160 may enable the end user and/or the administrator to select override operations for various fields. The override may apply to a template value replacing a manually entered value and/or a second template value replacing a value from a previously applied first template.

For example, the user may select a template that includes values for fields into which the user has already entered data. The ePCR application 160 may query the user on a field-by-field basis to ask if the end user wants to replace the entered value with the template value. Alternatively, the ePCR application 160 may enable the end user to select a global override such that the template application replaces every field in the open ePCR that already includes a value with a template value.

As another example, the ePCR application 160 may enable an administrator to designate one or more fields as automatic override fields and/or designate one or more templates as automatic override templates. For example, the agency may require that if the "response mode" field value is "emergency," then the "additional response mode" field includes "lights and sirens." To accommodate such a requirement, the administrator may create an "emergency" template that includes "lights and sirens" in the "additional response mode" field and may designate this field as an override field. The value of an automatic override field may replace, or overwrite, another value entered in that field.

In an implementation, various fields may trigger a reversal override. In a reversal override, a particular field value may take precedence over another field value and initiate a reversal of field values. For example, a field value of "emergent" may take precedence over "non-emergent." A first template may fill in a set of second fields based on a "non-emergent" value in a first field. A second template may have the value of "emergent" in the first field and, upon application of the second template, the ePCR application 160 may replace (e.g., overwrite) and/or erase values from one or more of the set of second fields that include values associated with "non-emergent" and incompatible with "emergent." As another example, "not canceled" may take precedence over "canceled." In an implementation, upon selection of a template, the ePCR application 160 may query the user to find out if they want to overwrite or erase values if templates have opposing and incompatible field entries.

Referring again to FIG. 7, the ePCR template layering process 2400 starts with the ePCR application receiving 2402 a request to generate an ePCR. In response to receiving 2402 the request to generate the ePCR, the ePCR application may access 2404 a pre-configured ePCR form that specifies a list of fillable ePCR fields included within the requested ePCR. The pre-configured ePCR form may have a large quantity of fields (e.g., 50-1000 fields). Each field may require a specific data type as an entry to the field. For example, the pre-configured ePCR form may be stored in a memory (e.g., the memory 321, 421, and/or 521 as shown in FIG. 20). In accessing 2404 the stored pre-configured ePCR form, in some examples, the ePCR application 160 creates a copy of the ePCR form, and its fields, in a same or different memory to provide the open ePCR. The ePCR user interface 180 may enable the user to provide entries to the fields of the copied ePCR form, i.e., the open ePCR, to generate a completed ePCR for the specific emergency event.

Next, the ePCR application 160 provides 2406, via the ePCR user interface 180, an ePCR template selection window, such as the template selection window 1000 illustrated, for example, in FIG. 2. The template may facilitate entry of data into the fields of the copied ePCR form. The ePCR application receives 2408 a confirmed selection of multiple ePCR template controls via the user interface. For example, the ePCR application may receive 2408 input selecting two or more ePCR template controls from a list of ePCR template controls (e.g., the list of ePCR template controls 1002 of FIG. 2) and input selecting of a yes control (e.g., the "yes" control 1102 of FIG. 6).

In some examples, the ePCR application tracks ePCR templates that are selected together and stores associations between the templates where they are selected together more than a threshold number of times (e.g., 2 time, 5 times, 10 times, or more times) by the same user or overall. The ePCR application may use these associations to suggest complementary ePCR templates, e.g., particular ePCR template combinations for layering, as described with reference to FIG. 4A and FIG. 9.

Continuing the ePCR template layering process 2400, the ePCR application identifies 2410 non-overlapping and overlapping fields within selected ePCR templates associated with the selected ePCR template controls. For example, the ePCR application may identify fields having a common name (or other identifier unique within each selected ePCR template). In this example, fields with a common name are recorded as overlapping and fields with unique names are recorded as non-overlapping. In some examples, the ePCR application 160 provides a notification (e.g., via the user interface 180) of the presence of overlapping fields to prompt the user to resolve a template conflict where one or more overlapping single use fields are detected. In the case of field value conflicts, the ePCR application 160 may require user input to select the field value. As discussed herein, in some implementations, one or more fields and/or one or more templates may provide automatic overwrite capabilities.

The ePCR application 160 next populates 2412 fields within the second ePCR form, e.g., the open ePCR, that correspond to the non-overlapping fields with the pre-determined values specified in the selected templates for the overlapping fields. For example, the ePCR application 160 may fill non-overlapping fields with the pre-determined values specified in the selected templates by their order of selection (e.g., fill values from the first selected ePCR template first, fill values from the second selected ePCR template second, etc.).

In an implementation, the ePCR application 160 also populates 2412 fields within the second ePCR form, e.g., the open ePCR, that correspond to the overlapping fields in accordance with a set of pre-determined selection rules. For example, the ePCR application may execute an overlap populator (e.g., the overlap populator 2308 described above with reference to FIG. 4A) for each overlapping field. In this example, the overlap populator 2308 first fills the overlapping fields within the second ePCR form with pre-determined values from the first selected ePCR template and then either skips values from other ePCR templates (e.g., where the overlapping field is a single-use field) or add values from other ePCR templates (e.g., where the overlapping field is a multi-select or text field).

Although the ePCR template layering process 2400 described above populates ePCR fields using a particular order of selected ePCR templates, the examples disclosed herein are not limited to the particular order described. For instance, in some examples, the ePCR template layering process iteratively visits each ePCR field to be populated (e.g., as they are ordered within the open ePCR) and applies the rules described above as the ePCR template layering process moves through the open ePCR. Other variations will be understood by those skilled in the art in view of this disclosure.

Next, the ePCR application generates 2416 a new ePCR from the populated ePCR form and the ePCR template layering process 2400 ends. The new ePCR may be a completed version of the open ePCR. For example, the ePCR application may insert a new ePCR record and new ePCR field records associated with the new ePCR record in the memory. In some examples, the ePCR application stores the populated ePCR in the memory automatically (e.g., without requiring a receipt of a command from a user). Once finalized, the new ePCR may be uploaded to an administrative environment (e.g., the administrative environment 103 of FIG. 4) and/or another destination server, computing device, and/or medical device, as described above.

Processes in accordance with the ePCR template layering process 2400 may enable ePCR systems to intelligently merge multiple ePCR templates into a single ePCR to help users decrease both errors in, and time required to complete, ePCRs.

Figure 8:
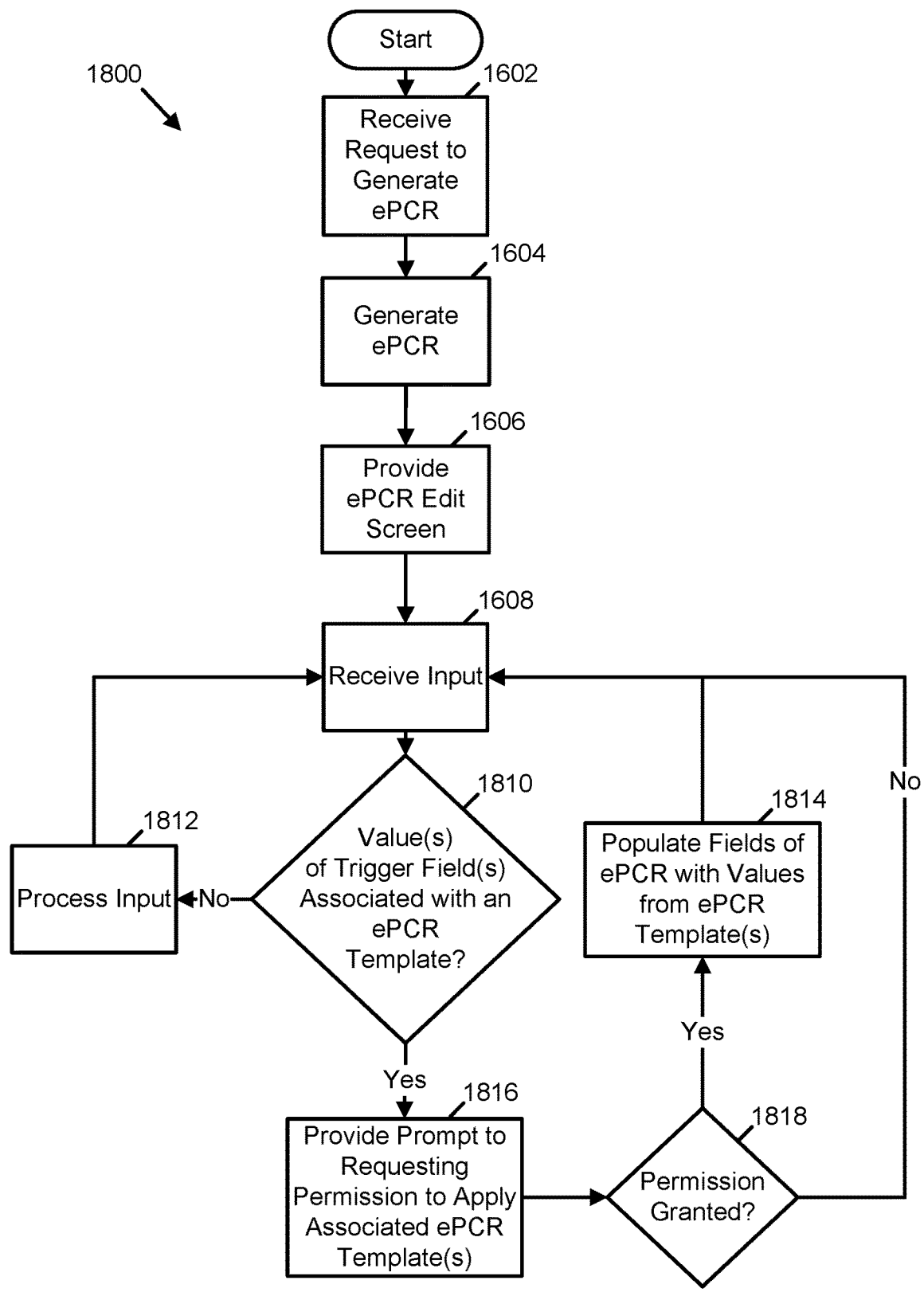
FIG. 8 is a flow diagram illustrating an ePCR template suggestion process in accordance with at least one example disclosed herein.

FIG. 8 illustrates one example of an ePCR template suggestion process 1800. Many of the acts illustrated in FIG. 8 are described above with reference to FIG. 5. For purposes of brevity, those descriptions will not be repeated here, but each of the acts of FIG. 5 included in FIG. 8 is performed in FIG. 8 as described in FIG. 5. For example, these descriptions apply to the acts 1602, 1604, 1606, and 1608 of the process 1800.

Following the action 1608, the ePCR application 160 determines 1810 whether values stored in one or more trigger fields are associated with one or more ePCR templates. For example, the ePCR application 160 may execute an ePCR type identifier (e.g., the ePCR type identifier 1708 described above with reference to FIG. 4A). In this example, the ePCR type identifier compares the values stored in one or more trigger fields to sets of trigger values associated with ePCR templates within one or more cross-references stored in memory (e.g., the memory 321, 421, and/or 521 of FIG. 20). Where such an association is present, the ePCR type identifier notifies the ePCR application 160 that the values of the trigger fields are associated with the one or more ePCR templates.

Where the ePCR application 160 determines 1810 that the values are not associated with an ePCR template, the ePCR application processes 1812 the input and returns to receiving 1608 input. For example, where the input specifies a value for an ePCR field, the ePCR application stores the value in the ePCR field.

Where the ePCR application determines 1810 that the values are associated with one or more ePCR templates, the ePCR application provides 1816 (e.g., via the user interface 180 of FIG. 4A) a prompt requesting permission to apply the one or more ePCR templates to the ePCR being edited.

The ePCR application determines 1818 whether permission to apply the one or more ePCR templates is granted or denied. For example, the ePCR application may receive input specifying a response to the prompt. Where the ePCR application determines 1818 that permission is granted, the ePCR application may populate 1814 the fields of the ePCR being edited with values specified by the one or more ePCR templates. For example, the ePCR application may populate 1814 the fields by iteratively executing the act 1614 as described with regard to FIG. 5 in order to apply each of the one or more ePCR templates. Where the ePCR application determines 1818 that permission is denied, the ePCR application returns to receiving 1608 input.

Processes in accordance with the ePCR template suggestion process 1800 may enable ePCR systems to intelligently suggest ePCR templates to users to help the users decrease both errors in, and time required to complete, ePCRs.

Figure 9:
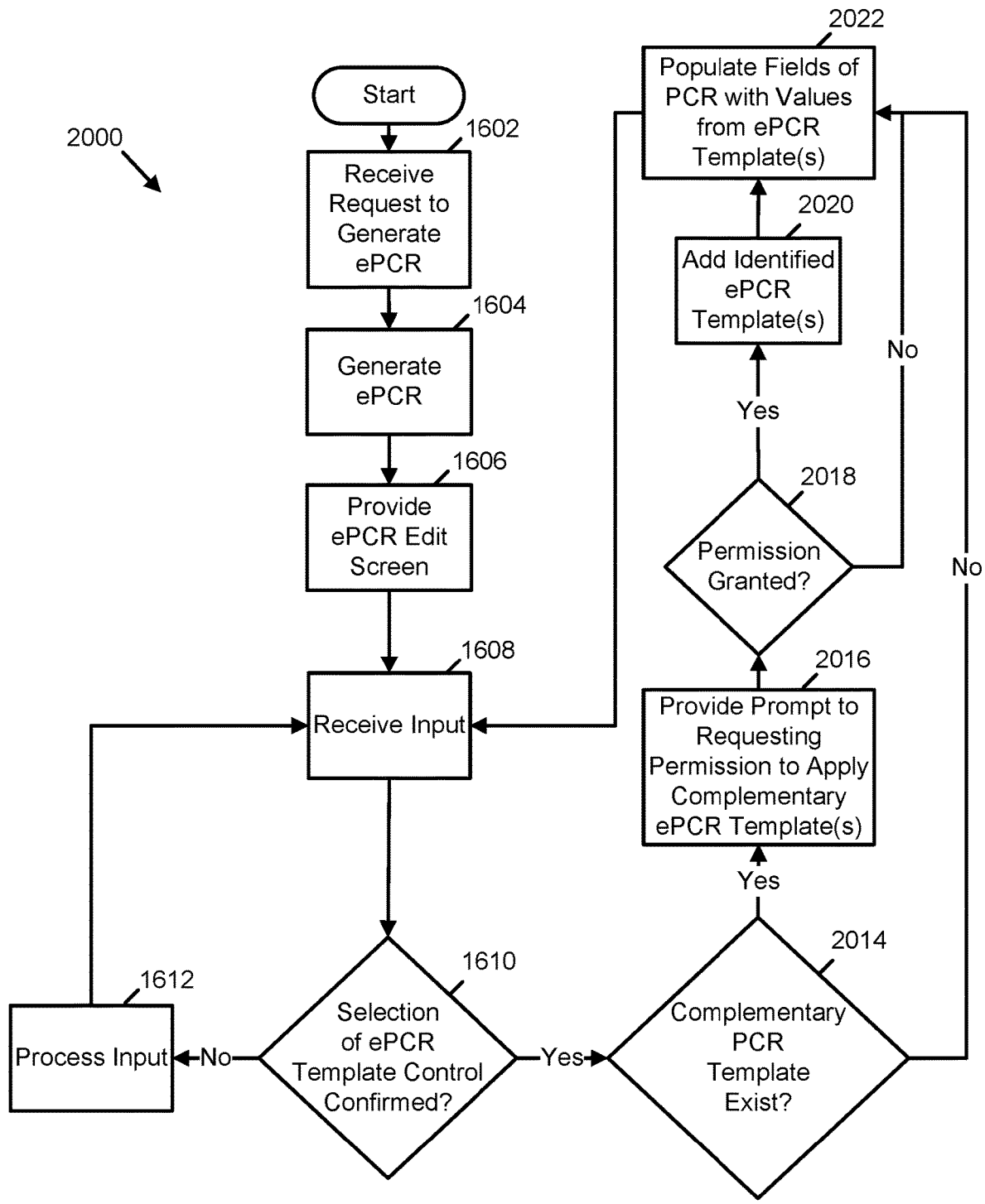
FIG. 9 is a flow diagram illustrating an ePCR template suggestion process in accordance with at least one example disclosed herein.

FIG. 9 illustrates another example of an ePCR template suggestion process. Many of the acts illustrated in FIG. 9 are described above with reference to FIG. 5. For purposes of brevity, those descriptions will not be repeated here, but each of the acts of FIG. 9 included in FIG. 5 is performed in FIG. 9 as described in FIG. 5. For example, these descriptions apply to the acts 1602, 1604, 1606, 1608, 1610, and 1612 of the process 2000.

Following the stage 1610, if selection of the ePCR template control is confirmed, the ePCR application 160 determines 2014 whether any ePCR templates exist that are complementary to a selected ePCR template associated with the selected ePCR template control. For example, the ePCR application 160 may execute an ePCR template identifier (e.g., the ePCR template identifier 1908 described above with reference to FIG. 4A). In this example, the ePCR template identifier 1908 searches a cross-reference stored in memory (e.g., the memory 321, 421, and/or 521 of FIG. 20) for an association between an identifier of the selected ePCR template and one or more identifiers of one or more complementary ePCR templates. Where such an association is present, the ePCR template identifier 1908 notifies the ePCR application 160 that one or more complementary ePCR templates exist and are identified.

Where the ePCR application 160 determines 2014 that no complementary ePCR templates exist, the ePCR application 160 populates 2022 the fields of the ePCR being edited with values specified by the selected ePCR template. For example, the ePCR application 160 may execute the act 2022 for the selected template.

Where the ePCR application 160 determines 2010 that complementary ePCR templates exist, the ePCR application provides 2016 (e.g., via the user interface 180 of FIG. 4A) a prompt requesting permission to apply the one or more complementary ePCR templates to the ePCR being edited (e.g., the open ePCR).

The ePCR application 160 determines 2018 whether permission to apply the one or more complementary ePCR templates is granted. For example, the ePCR application may receive input specifying a response to the prompt provided at the act 2016. Where the ePCR application 160 determines 2018 that permission is granted, the ePCR application 160 adds 2020 the one or more complementary ePCR templates to a list of ePCR templates to be applied and populates 2022 the fields of the ePCR being edited with values specified by each ePCR template in the list of ePCR templates. For example, the ePCR application 160 may iteratively execute the act 1614 described with regard to FIG. 5 for each ePCR template in the list of ePCR templates. Where the ePCR application 160 determines 2016 that permission is denied, the ePCR application 160 proceeds to populate 2022 the fields of the ePCR being edited with values specified by the selected ePCR template. In either case, upon completion of the population 2022, the ePCR application 160 returns to receiving 1608 input.

Processes in accordance with the ePCR template suggestion process 2000 may enable ePCR systems to intelligently suggest ePCR templates to users to help the users decrease both errors in, and time require to complete, ePCRs.

Figure 10:
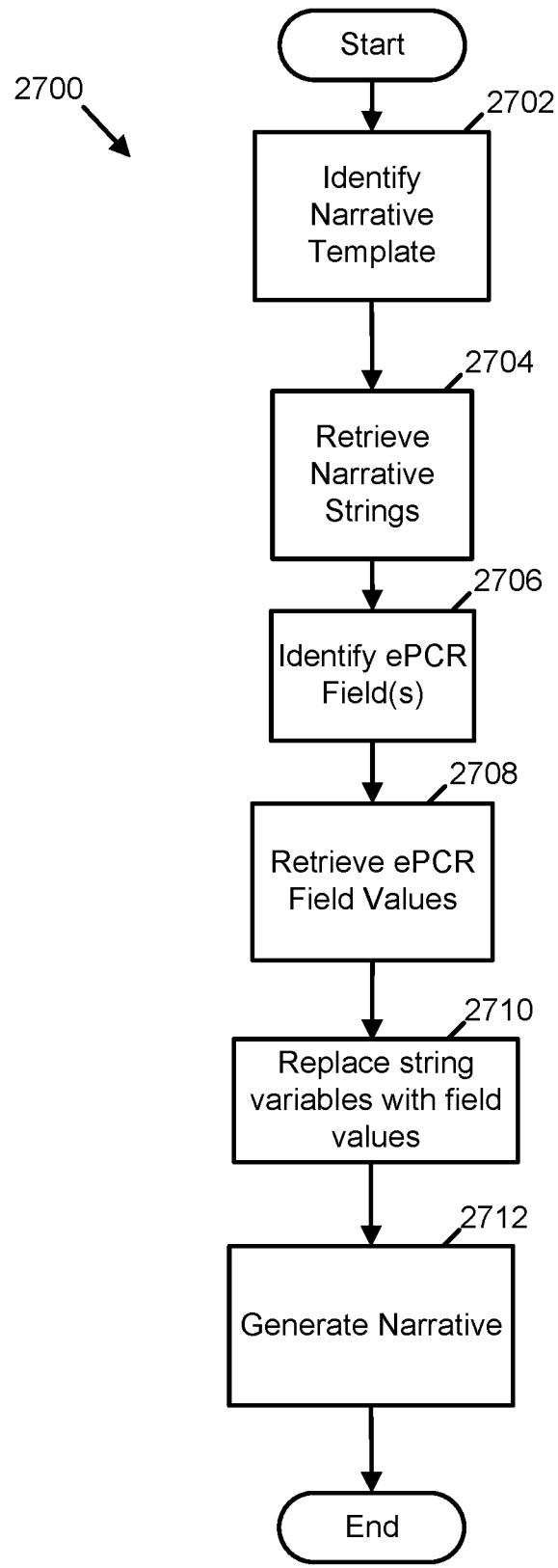
FIG. 10 is a view of a warning screen provided by an ePCR application in accordance with at least one example disclosed herein.

FIG. 10 illustrates one example of a template assisted narrative generation process 2700. The narrative field of an ePCR may be a required section that tells the story of the patient encounter. The narrative field functions as a specialized fillable field in which the EMS worker may provide a paragraph describing the patient encounter. Post-EMS care and/or billing services may utilize details in the narrative as the narrative provides a summary of the patient encounter. The narrative may include observations and comments from the caregiver as well as medical history, complaints, etc. from the patient. Such information may be crucial for effective post-event patient care.

As an example not limiting of the disclosure, a narrative may include a paragraph such as:

"Dispatched to 123 Main Street for an elevated temperature call. Arrived on scene to find a female patient lying on a couch, with a Glasgow Coma Score of 15. Patient stated that she was not feeling well for 3 days and has been running a temperature. Patient stated that she did take Tylenol and still the temperature did not go down. Assessed Patient and found skin to be very warm and dry, BP 150/80, pulse of 110 and regular. Lungs were clear in all fields. Mild dizziness but no vomiting. Patient has eaten this morning and has been able to take normal fluid intake. Pulse ox was 90% on room air. Temperature was 101.5. Placed two ice packs under the arm pits to control temperature. Placed Patient on 6 LPM via simple face mask. Pulse ox then rose to 97-98%, Patient has no prior medical history or allergies. Medications include levothyroxine 25 mg daily. Called report to hospital via medical radio, no orders given. Arrived at hospital and transferred care to ER staff."

Despite being a required and valuable portion of the ePCR, EMS workers may provide a hastily written and therefore possibly incomplete and/or inaccurate narrative. This may be due to the time-consuming nature of the narrative along with the redundancy of including details in the narrative that are found in other parts of the ePCR, namely in the other fillable fields. Without a template, the narrative field is a free-form section of the ePCR. At least in order to prevent incomplete narratives, provide standardized formats for an agency, and/or save time for the caregivers by reducing redundant data entry, an agency administrator may generate narrative templates. For example, the administrator may create narrative templates for specific scenarios such as cancelled calls, cardiac calls, hospital transports, etc. As another example, the administrator may create narrative templates that guide the end user through a particular outline such as SOAP or CHART. In some examples, EMS agencies may require or suggest that the narrative follow an EMS outline such as SOAP (Subjective, Objective, Assessment, Plan) or CHART (Complaint, History, Assessment, Rx, Treatment), as discussed further below with regard to FIG. 13.

Figure 11:
FIG. 11 is a flow diagram illustrating a narrative generation process in accordance with at least one example disclosed herein.

As illustrated in FIG. 10, a template assisted narrative generation process 2700 starts with the ePCR application 160 identifying 2702 a narrative template that the ePCR application is applying to an ePCR. In an implementation, the narrative template may be an auto-fill narrative template. For example, referring to FIG. 11, the end user may select a narrative template control 1310. Upon selection of the narrative template control, the ePCR application 160 may provide a warning screen. For example, FIG. 11 illustrates an example warning screen 1300 indicating that an ePCR template named "Narrative Template" is about to be applied to the ePCR being generated. Upon confirmation of the selection of the narrative template, the user may navigate to a narrative field in the ePCR being edited to review the narrative field.

Figure 12A:
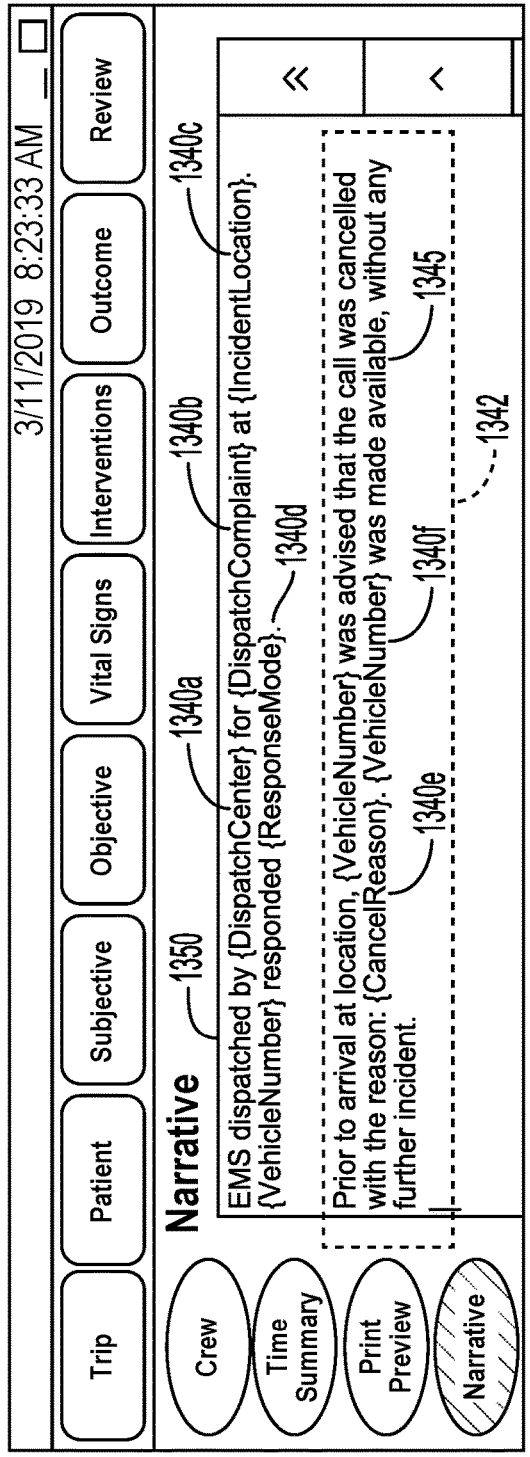
FIGS. 12A and 12B are schematic examples of an auto-fill narrative template.
Figure 12B:
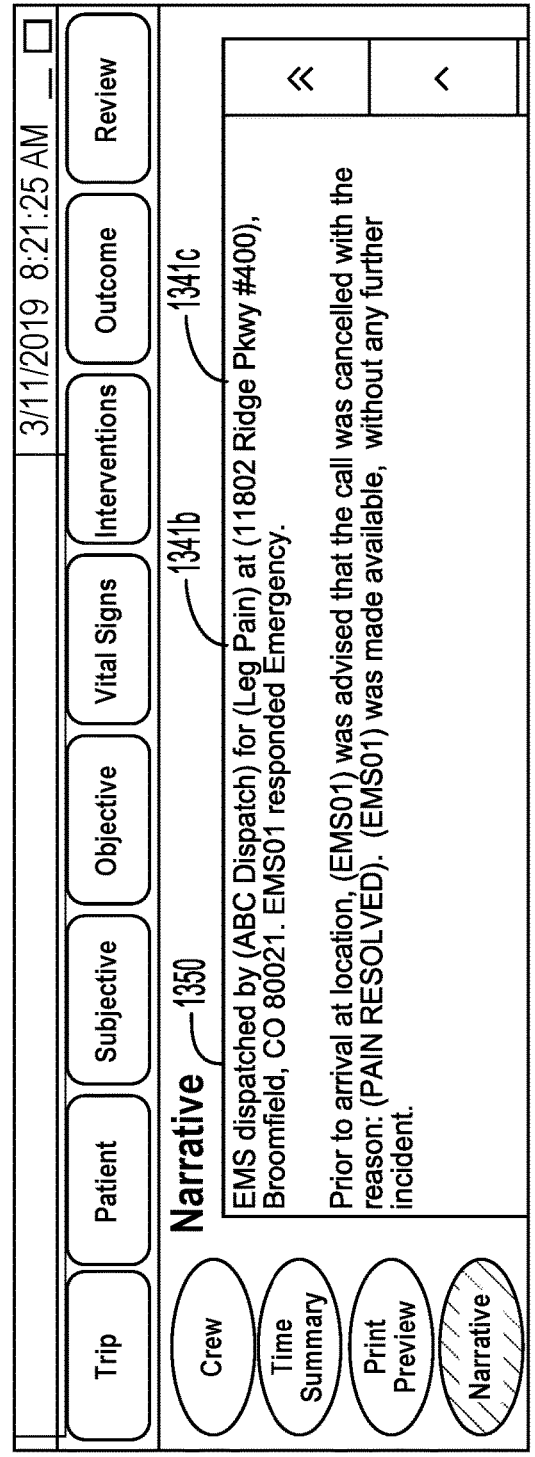
Figure 15:
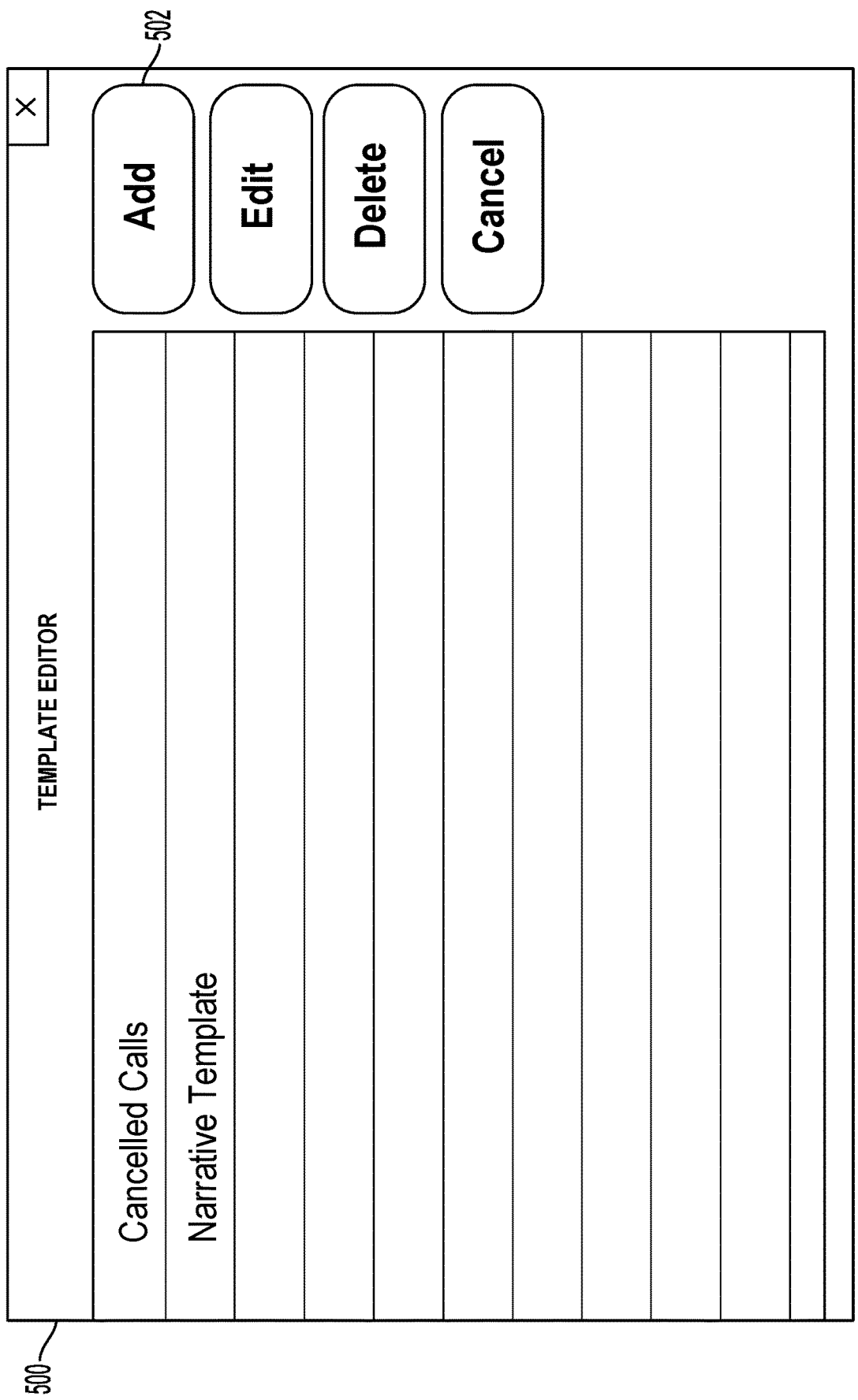
Figure 18:
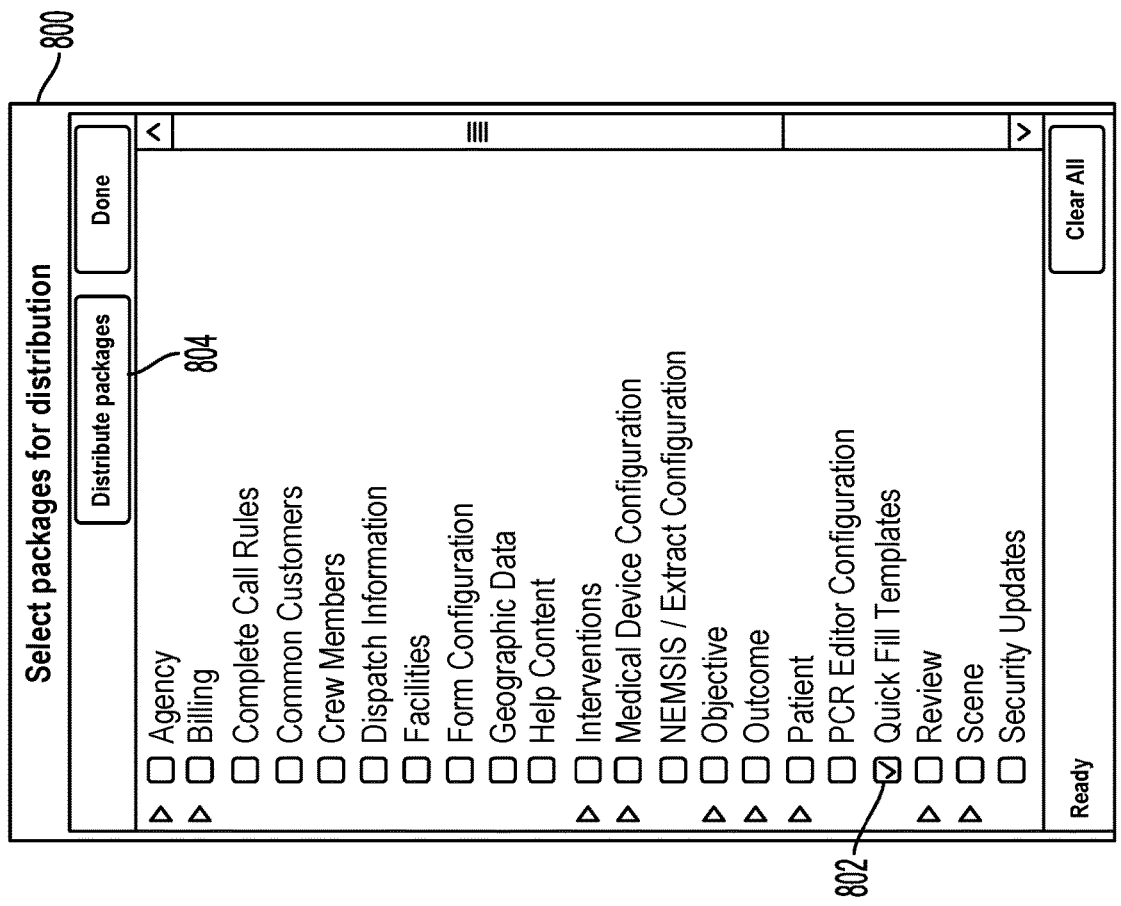

The narrative generator may retrieve 2704 one or more strings stored in the narrative field via the narrative template. For example, referring to FIGS. 12A and 12B, in an implementation, the auto-fill narrative template may include one or more narrative strings (e.g., the text within the box 1342). The string includes literals (e.g., the text outside of brackets, such as the literal 1345 and the literal 1350 of FIG. 12B) and variables (e.g., the text within brackets) 1340a, 1340b, 1340c, 1340d, 1340e, and 1340f Each variable may include an ePCR field identifier. One or more of the variables may repeat within the template. For example, as shown in FIG. 12A, the "Vehicle Number" variable 1340f, repeats three times. The ePCR application 160, in response to identifying the narrative template at the auto-fill narrative template, may execute a narrative generator (e.g., the narrative generator 2608 of FIG. 4A In an implementation, the narrative generator may generate narrative text using the one or more strings and variable values that are stored in ePCR fields of the ePCR other than the narrative field. For example, the narrative generator 2608 may parse the one or more strings to identify the literals and the variables. Based on the identifiers included in the variables, the narrative generator 2608 may identify 2706 ePCR fields that correspond to the variables. Next, the narrative generator 2608 may retrieve 2708 the values stored in the ePCR fields and replace 2710 the variables within the string with their corresponding field values to generate 2712 the narrative text. For example, as shown in FIG. 12B, the field value 1341b of "Leg Pain" replaces the variable 1340b with the identifier "DispatchComplaint." "DispatchComplaint" may be a fillable ePCR field outside of the narrative. As another example, the field value 1341c of "11802 Ridge Pkwy #400" replaces the variable 1340c with the identifier "IncidentLocation." "IncidentLocation" may be a fillable ePCR field outside of the narrative. The end user may already have populated these fields in the open ePCR, either manually or via a template application. With the auto-fill narrative template, the end user may save critical time during an emergency response by not having to re-enter information into the narrative that is already found in the open ePCR but outside the narrative. The narrative generator 2608 may store the narrative text and return execution control of ePCR generation to the ePCR application 160, which may continue to enable population of the open ePCR.

Processes in accordance with the narrative generation process 2700 may enable ePCR systems to quickly create meaningful narratives for some dispatched EMS event. This feature may help users decrease both errors in, and time require to complete, ePCRs.

Figure 13:
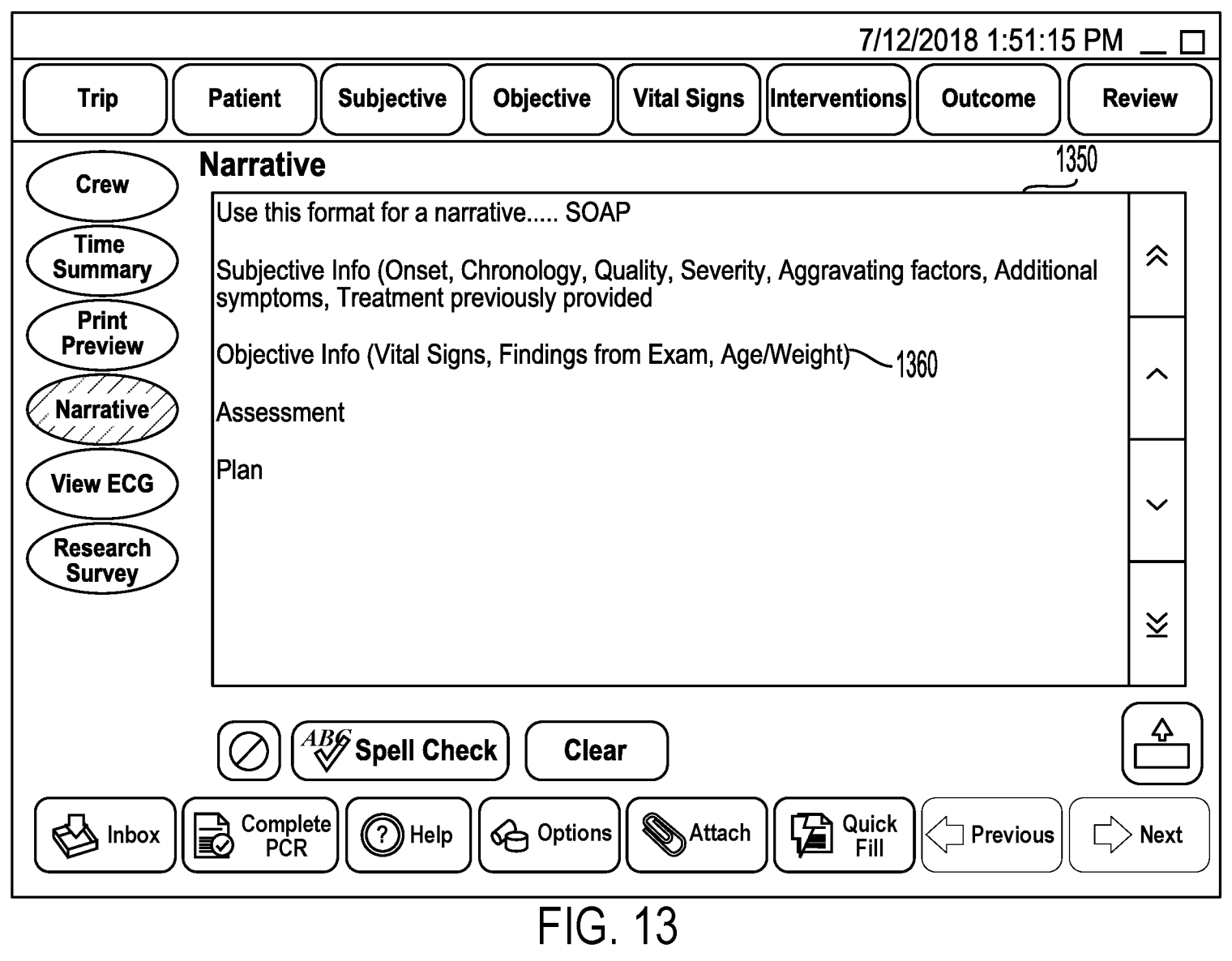

Referring to FIG. 13, an example of an example of a guided narrative template that guides the user through a particular outline is shown. As shown in FIG. 13, the narrative field 1350 has been populated with a narrative guide 1360. The narrative guide 1360 in this example includes a guide for a SOAP style narrative. In this example, the end user may populate the narrative field according to the SOAP style narrative. The guided narrative template may or may not include the fillable strings discussed with regard to FIGS. 12A and 12B.

To provide the ePCR templates described above, the ePCR application 160 may provide the ePCR user interface 180 shown in FIG. 4A. The user interface 180 may enable a process by which a user, such as the administrator 134 shown in FIG. 4A, may generate and store the ePCR templates.

Figure 14:
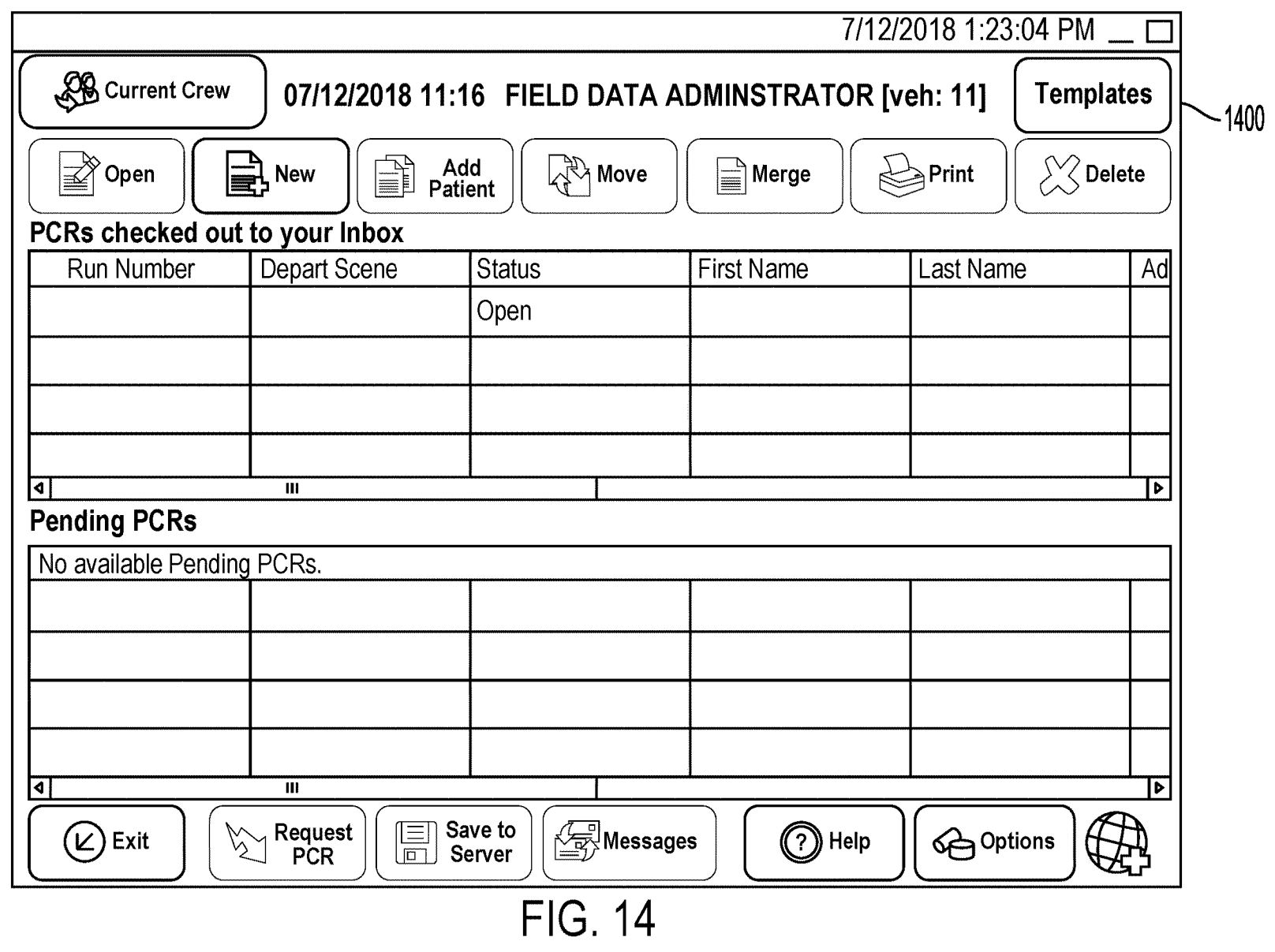
Figure 17:
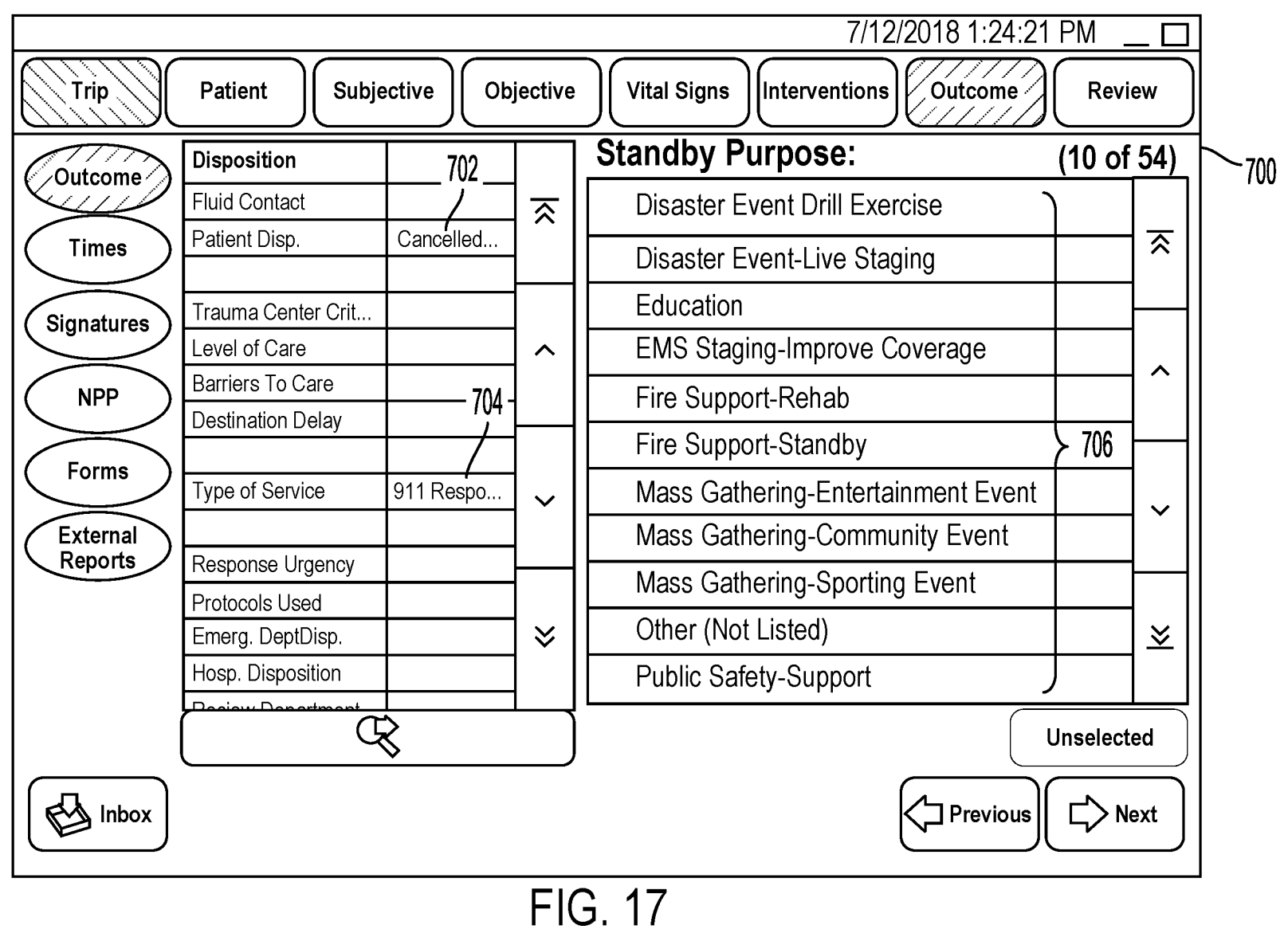

Referring to FIGS. 14-18, examples of user interface screens for template generation are shown. In an implementation, an administrator (e.g., a user with administrator privileges) may set up ePCR template(s) at a computing device (e.g., the computing device 132). In some examples, the ePCR application 160 is configured to first determine (e.g., by an access security setting, login credentials, etc.) whether the user has administrator privileges to set up the ePCR template(s). If so, the ePCR application may enable an ePCR template control 1400, as shown in FIG. 14, for selection by the administrator. Otherwise, the ePCR application may disable and/or hide the ePCR template control 1400. In an example, the template includes the same ePCR form provided to users of the ePCR application. Upon completion, the template includes values for a subset of the required fields in the ePCR. The template may be limited to values for fields that pertain to the type of template. These values are entered into the ePCR generated during an actual patient call by applying the template. In contrast to the template, the ePCR generated during the actual patient call may include values for every required field.

To create the ePCR template(s), the administrator may select the ePCR template control 1400. In response to receiving a selection of the ePCR template control 1400, the ePCR application 160 may open a template editor page or screen 500, as illustrated, for example, in FIG. 15. On this screen, the administrator may select to add a new template, edit an existing template, or delete a template. In this example, the administrator selects the add control 502 to add the new template.

In response to receiving a selection of the add control 502, the ePCR application 160 may provide a template title screen 600, as shown for example in FIG. 16, that may include one or more of a name control 602, a distribution control 604, and a create control 606. The administrator may enter an ePCR template name. In the example of FIG. 16, the ePCR template name is "Patient Refusal." The ePCR template name may identify the ePCR template and may be visible to an end user (e.g., the healthcare provider 114) to enable selection of the ePCR template for use in generation of a new ePCR. In response to receiving input at the name control 602, the ePCR application may store the input in the name control 602.

The administrator interface may present an option 601, selectable by the administrator, to apply the template to a particular company (e.g., the company the administrator logged into) or to a group of companies that may include the particular company. The ePCR application 160 may enable the administrator to create templates for multiple companies or agencies and/or for specific crews within an agency and designate the templates accordingly. In this way, the ePCR application 160 may provide all templates to all companies, agencies, and/or crews or may only provide designated templates to each agency, company, and/or crew. In response to receiving a selection of one of the options presented by the distribution control 604, the ePCR application 160 may record the selected distribution option as the current distribution option. The ePCR application 160 may stores the ePCR template under the name stored in the name control 602. As shown in FIG. 16, the name of the template is "Patient Refusal" and upon the completion of the new template, the ePCR application 160 may distribute the new ePCR template according to the distribution option selected in the distribution options control 604, here "All Companies."

The administrator may click a create control 606 and the ePCR application 160 may open a window that may be substantially identical at least in appearance to a window from which the end user (e.g., the healthcare provider 114) would start a new ePCR for a patient encounter (e.g., the ePCR generation described at least with regard to FIG. 1B). In response to receiving a selection of the create control 606, the ePCR application 160 opens the ePCR form and displays a screen, such as the ePCR screen 700 shown for example in FIG. 17, that includes controls that enable the administrator to populate fillable fields with values. The ePCR form used to generate the template(s) may be substantially identical to the ePCR form used to generate the ePCRs during a patient encounter. However, the ePCR application 160 may enable the ePCR form to be only partially filled during template creation according to the type of template. In other words, the ePCR form that constitutes the template may include empty fields. Only those fields relevant to the particular template may be filled. In contrast, complete call rules may require the ePCR form used to generate the ePCR during a patient encounter to be completely filled. In other words, the ePCR form that constitutes the ePCR documenting the patient encounter may not include empty fields.

The ePCR screen 700 may include recommended values 706 for one or more of the fillable fields. In some examples, the ePCR screen 700 includes controls that enable the administrator to easily identify, accept, select, and/or overwrite the recommended values.

In an implementation, the ePCR application 160 may exclude or hide one or more ePCR fields from the template generation screen. Alternatively or additionally, the ePCR application 160 may disable value entry for one or more of the ePCR fields during template generation. The administrator 134 may view the full ePCR form but may not access one or more fields and/or provide template entries for these fields. These fields may correspond to ePCR fields that are unique to each patient encounter. For example, a crew member identification field, a facility code, a vehicle identification field, a patient name, etc. may require a manual entry into a new ePCR for each patient encounter. Such fields may be ineligible as fields fillable via a template.

The administrator may fill out all or a portion of the fillable fields in the ePCR form that are applicable to the type of template being created. For example, for a "Cancelled Calls" template, the administrator may fill out fields such as "Patient Disposition" 702 and "Type of Service" 704. The "Patient Disposition" field 702 may be filled with "cancelled call" and the "Type of Service" field 704 may be filled with "911 response." The template text in these fields may be a default type of response for the organization.

In some examples, in response to receiving input specifying values of fields, such as the fields 702 and 704, the ePCR application 160 stores the values in the fields. As the administrator fills in fields, the ePCR application may autosave each of their selections. The administrator may fill out one, all, or a portion of the fields in the ePCR form at her discretion and/or based on the type of template.

Once the administrator has filled out all of the fields that he/she thinks may be valuable for the ePCR template, they may distribute the ePCR template to other computing devices (e.g., the computing device 104 of FIG. 1) so that the end users (e.g., the healthcare provider 114) may access them. To send newly created/edited ePCR templates (e.g., one ePCR template or a package of multiple ePCR templates) to the other computing devices, the administrator may initiate electronic distribution of the ePCR templates (e.g., a push of the created and/or updated templates). For example, the administrator may select a template designation control 802 (e.g., "Quick Fill Templates") and then select "Distribute Packages" control 804 within the distribution screen 800 illustrated in FIG. 18. The template designation control 802 may designate the ePCR form edited by the administrator as a template, as opposed to a newly generated ePCR for a patient encounter.

In some examples, in response to receiving a selection of the control 802, the ePCR application 160 toggles the selected state of the control from unselected to selected. In response to receiving a selection of the control 804, the ePCR application 160 may transmit a message to an application server (e.g., the one or more application servers 128 of FIG. 1). The message may include a template package that requests publication of the newly created and filled ePCR form as an ePCR template.

In response to receiving the message, the computing device 132 may interoperate with the server 128 and the ePCR application 160 to upload the newly created and filled ePCR template(s), create new ePCR template records in the ePCR data store 130, and store the names of the new ePCR templates (as specified in the name control 602 of FIG. 6) and additional metadata regarding the new ePCR templates in the new ePCR template records. The ePCR application 160 stores the plurality of values entered by the administrator into the fields of the ePCR template as a set of pre-determined values for a set of fields in the new ePCR generated for the patient encounter to be populated via selection of the ePCR template by the end user. Next, in an implementation, the server 128 interoperates with other instances of the ePCR application (e.g., functions of the ePCR application 160 on the computing device 104) to transmit a template package comprising one or more ePCR templates for use. For example, the computing device 104 and the ePCR application 160 may store the one or more ePCR templates in local storage (e.g., the memory 421 of the computing device 104 as shown in FIG. 20) for subsequent presentation to and use by the end user (e.g., the healthcare provider 114).

Once the template package has been received by the computing device 104, the end user (e.g., the healthcare provider 114) may access the ePCR templates in the ePCR application 160 by starting a new ePCR (e.g., via the new ePCR control 199 shown in FIG. 1A). In response to receiving input specifying creation of a new ePCR, the ePCR application 160 and the ePCR user interface 180 may provide the ePCR edit screen 900 discussed above and as illustrated, for example, in FIG. 1B.

Figure 19:
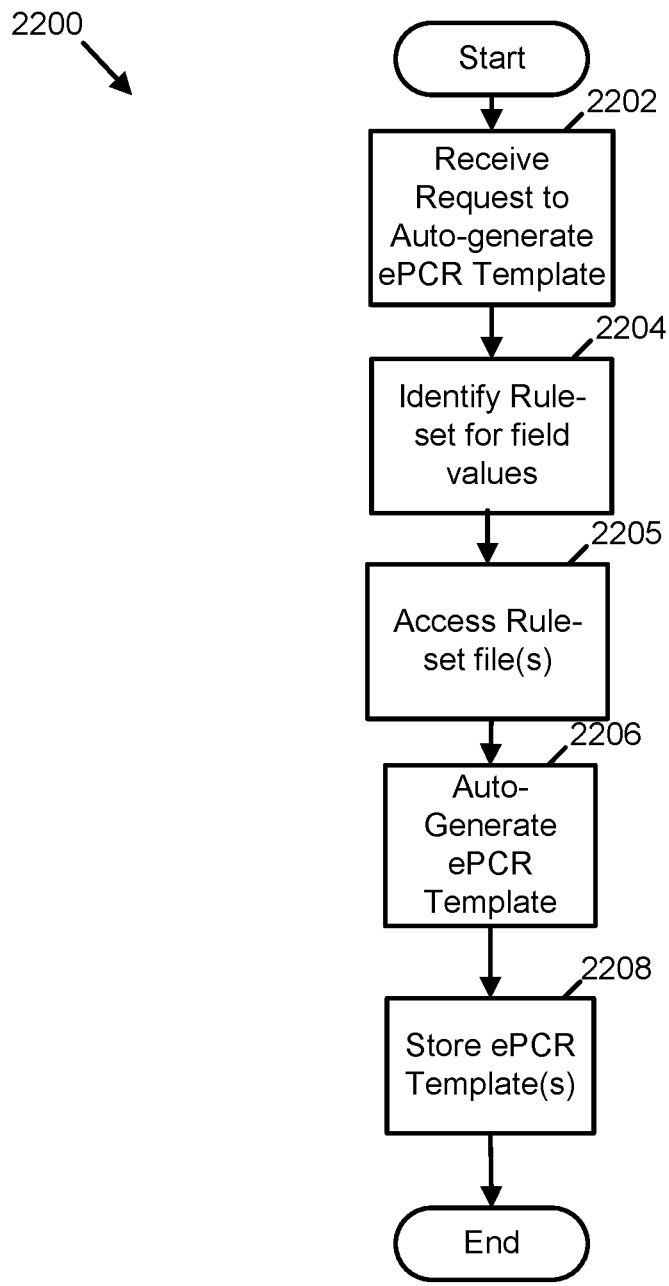
FIG. 19 is flow diagram illustrating a process of auto-generating an ePCR template according to a field value rule set in accordance with at least one example disclosed herein.

As illustrated in FIG. 19, an example of a process to auto-generate an ePCR template according to a field value rule set is shown. In an implementation, the ePCR template may be the auto-generated ePCR template that includes field values based on a context-sensitive rule set. The auto-generated ePCR template may not require user input from the administrator or may require only partial input from the administrator.

The process 2200 in FIG. 19 starts with the ePCR application 160 receiving 2202 a request to create an auto-generated ePCR template. For example, the ePCR application may receive input specifying the request from a user (e.g., the administrator 134 of FIG. 4A) via the ePCR user interface 180. The process 2200 may further include receiving 2204 an identification of a rule set. For example, the administrator may specify a complete call rule set or a Schematron rule set. The ePCR application 160 may import or otherwise access 2205 all or a portion of one or more files associated with the identified rule set. In an implementation, the request at the stage 2202 may include an identification of a template type corresponding to a particular ePCR field. In an implementation, the ePCR application 160 may import a portion of the rule set corresponding to the template type.

Following the access, the ePCR application 160 auto-generates 2206 the ePCR template based on the imported files for the identified rule set. For example, the ePCR application may execute an ePCR template generator (e.g., the ePCR template generator 2108 described above with reference to FIG. 4A). The ePCR template generator may access the rule set identified in the request and identifies 2204 each rule within the rule set that requires a pre-determined value be stored in a fillable field of the ePCR form. The ePCR template generator may automatically set the one or more second fields to the value(s) proscribed by the value in the first field according to the rule set. In an implementation, the administrator may select the fillable fields that store the pre-determined values. Alternatively, the ePCR application 160 may automatically select the fillable fields that store the pre-determined values based on, for example, the type of template.

As an example, the template type may be "no transport." The ePCR template generator may automatically enter "not applicable" into all transport related fields of the "no transport" template. As another example, the template type may be "male gender." The ePCR template generator may automatically enter "No" or "not applicable" into pregnancy related fields.

In an implementation, the ePCR application may insert a new ePCR template record and new ePCR template field records associated with the new ePCR template record in memory (e.g., the memory 421 of FIG. 21) and store, within the ePCR template fields, the values identified in the rule set. The ePCR template generator may store 2208 the new ePCR templates, for example, in the memory or within an ePCR data store (e.g., the ePCR data store 130 of FIG. 1) by interoperating with one or more storage servers (e.g., the server(s) 128 of FIG. 4A) and/or one or more application servers (e.g., the server(s) 128 of FIG. 4A) via a communication interface (e.g., the communication interface 545 of FIG. 20).

Processes in accordance with the rule-based ePCR template generation process 2200 enable ePCR systems to automatically generate ePCR templates to help administrators and end users decrease both errors in, and time require to complete, ePCRs that comply with the documentation practices required by their employers and/or government agencies.

Referring to FIG. 20, a block diagram of examples of computing and medical device components are shown schematically.

The medical device 106 may include a processor 220, a memory 221, one or more output devices 230, one or more user input devices 244, and a communications interface 245. The communications interface 245 may include any of a variety of transmitters and/or receivers. For instance, in some examples, the communications interface 245 includes one or more of an NFC tag, an RFID tag, a barcode, and a QR code.

In various implementations, the medical device 106 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 106 may be an integrated therapy delivery/monitoring device within a single housing 280. The single housing 280 may surround, at least in part, a patient interface device signal processor 256 and/or a therapy delivery control 255.

The patient interface device(s) 260 may include one or more therapy delivery component(s) 261*a* and/or one or more sensor device(s) 261*b*. The medical device 106 may be configured to couple to the one or more therapy delivery component(s) 261*a*. In combination, the medical device 106 and the one or more therapy delivery components may provide therapeutic treatment to a patient (e.g., the patient 116 of FIG. 1). In an implementation, the medical device 106 may include or incorporate the therapy delivery component(s) 261*a*. The therapy delivery component(s) 261*a* are configured to deliver therapy to the patient and may be configured to couple to the patient. For example, the therapy delivery component(s) 261*a* may include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 106 may include the one or more therapy delivery component(s) 261*a* and/or may be configured to couple to the one or more therapy delivery component(s) 261*a* in order to provide medical therapy to the patient. The therapy delivery component(s) 261*a* may be configured to couple to the patient. For example, a healthcare provider (e.g., the healthcare provider 114) may attach the electrodes to the patient, and the medical device 106 (e.g., a defibrillator or defibrillator/patient monitor) may provide electrotherapy to the patient via the defibrillation electrodes. These examples are not limiting of the disclosure as other types of medical devices, therapy delivery components, sensors, and therapy are within the scope of the disclosure.

The medical device 106 may be, for example, a therapeutic medical device capable of delivering a medical therapy. For example, the medical therapy may be electrical therapy (e.g. defibrillation, cardiac pacing, synchronized cardioversion, diaphragmatic or phrenic nerve stimulation) and the medical device 106 may be a defibrillator, a defibrillator/monitor and/or another medical device configured to provide electrotherapy. As another example, the medical therapy may be chest compression therapy for treatment of cardiac arrest and the first medical device 106 may be a mechanical chest compression device such as a belt-based chest compression device or a piston-based chest compression device. As other examples, the medical therapy may be ventilation therapy, therapeutic cooling or other temperature management, invasive hemodynamic support therapy (e.g. Extracorporeal Membrane Oxygenation (ECMO)), etc. and the medical device 106 may be a device configured to provide a respective therapy. In an implementation, the medical device 106 may be a combination of one or more of these examples. The therapeutic medical device may include patient monitoring capabilities via one or more sensors. These types of medical therapy and devices are examples only and not limiting of the disclosure.

The medical device 106 may include, incorporate, and/or be configured to couple to the one or more sensor(s) 261*b* which may be configured to couple to the patient. The sensor(s) 261*b* are configured to provide signals indicative of sensor data to the medical device 106. The sensor(s) 261*b* may be configured to couple to the patient. For example, the sensor(s) 261*b* may include cardiac sensing electrodes, a chest compression sensor, and/or ventilation sensors. The one or more sensors 261*b* may generate signals indicative of physiological parameters of the patient. For example, the physiological parameters may include one or more of at least one vital sign, an ECG, blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. Additionally or alternatively, the one or more sensors 261*b* may generate signals indicative of chest compression parameters, ventilation parameters, drug delivery parameters, fluid delivery parameters, etc.

In addition to delivering therapy to the patient, the therapy delivery component(s) 261*a* may include, be coupled to, and/or function as sensors and provide signals indicative of sensor data (e.g., second sensor data) to the medical device 106. For example, the defibrillation electrodes may be configured as cardiac sensing electrodes as well as electrotherapy delivery devices and may provide signals indicative of transthoracic impedance, electrocardiogram (ECG), heart rate and/or other physiological parameters. As another example, a therapeutic cooling device may be an intravenous cooling device. Such a cooling device may include an intravenous (IV) device as a therapy delivery component configured to deliver cooling therapy and sense the patient's temperature. For example, the IV device may be a catheter that includes saline balloons configured to adjust the patient's temperature via circulation of temperature controlled saline solution. In addition, the catheter may include a temperature probe configured to sense the patient's temperature. As a further example, an IV device may provide therapy via drug delivery and/or fluid management. The IV device may also monitor and/or enabling monitoring of a patient via blood sampling and/or venous pressure monitoring (e.g., central venous pressure (CVP) monitoring).

The medical device 106 may be configured to receive the sensor signals (e.g., from the therapy delivery component(s) 261*a* and/or the sensor(s) 261*b*) and to process the sensor signals to determine and collect the patient data. The patient data may include patient data which may characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infrared Spectroscopy (NIRS) measurements, etc.). Additionally or alternatively, the patient data may characterize the delivery of therapy (e.g., chest compression data such as compression depth, compression rate, etc.) and/or the patient data may characterize a status and/or condition of the medical equipment used to treat the patient (e.g., device data such as shock time, shock duration, attachment of electrodes, power-on, etc.).

The components of 220, 221, 230, 244, 245, and 255 of the medical device 106 are communicatively coupled (directly and/or indirectly) to each other for bi-directional communication.

Although shown as separate entities in FIG. 20, the one or more of the components of the medical device 106 may be combined into one or more discrete components and/or may be part of the processor 220. The processor 220 and the memory 221 may include and/or be coupled to associated circuitry to perform the functions described herein.

In an implementation, the medical device 106 may be a therapeutic medical device configured to deliver medical therapy to the patient. Thus, the device 106 may optionally include the therapy delivery control module 255. For example, the therapy delivery control module 255 may be an electrotherapy delivery circuit that includes one or more capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 255 may be a compression device electro-mechanical controller configured to control a mechanical compression device. As a further example, the therapy delivery control module 255 may be an electro-mechanical controller configured to control drug delivery, temperature management, ventilation, and/or other type of therapy delivery. Alternatively, some examples of the medical device 106 may not be configured to deliver medical therapy to the patient 116 but may be configured to provide patient monitoring and/or diagnostic care. As shown in FIG. 20, in some examples, the therapy delivery control 255 exchanges messages 1180 with the computing device 104 (e.g., the patient charting device). These messages may include patient data descriptive of therapy provided to the patient or other patient data stored on the medical device 106. This patient data may be used by the ePCR application 160 in generating an ePCR documenting a dispatched EMS event. For instance, in some examples, the patient data may be used as an input by the ePCR application to select (or suggest for user confirmation) a particular ePCR template. In at least one example, the patient data reflects a STEMI condition and the ePCR applies or suggests a STEMI template.

The medical device 106 may incorporate and/or be configured to couple to one or more patient interface device(s) 260. The patient interface device(s) 260 may include one or more therapy delivery component(s) 261*a* and one or more sensor(s) 261*b*. The one or more therapy delivery component(s) 261*a* and the one or more sensor(s) 261*b* sensor may provide one or more signals to the medical device 106 via wired and/or wireless connection (s).

The one or more therapy delivery components 261*a* may include electrotherapy electrodes (e.g., the electrotherapy electrodes 266*a*), ventilation device(s) (e.g., the ventilation devices 266*b*), intravenous device(s) (e.g., the intravenous devices 266*c*), compression device(s) (e.g., the compression devices 266*d*), etc. For example, the electrotherapy electrodes may include defibrillation electrodes, pacing electrodes, and/or combinations thereof. The ventilation devices may include a tube, a mask, an abdominal and/or chest compressor (e.g., a belt, a cuirass, etc.), etc. and combinations thereof. The intravenous devices may include drug delivery devices, fluid delivery devices, and combinations thereof. The compression devices may include mechanical compression devices such as abdominal compressors, chest compressors, belts, pistons, and combinations thereof. In various implementation, the therapy delivery component(s) 261*a* may be configured to provide sensor data and/or be coupled to and/or incorporate sensors. For example, the electrotherapy electrodes may provide sensor data such as transthoracic impedance, ECG, heart rate, etc. Further the electrotherapy electrodes may include and or be coupled to a chest compression sensor. As another example, the ventilation devices may be coupled to and/or incorporate flow sensors, gas species sensors (e.g., oxygen sensor, carbon dioxide sensor, etc.), etc. As a further example, the intravenous devices may be coupled to and/or incorporate temperature sensors, flow sensors, blood pressure sensors, etc. As yet another example, the compression devices may be coupled to and/or incorporate chest compression sensors, patient position sensors, etc. The therapy delivery control module 255 may be configured to couple to and control the therapy delivery component(s) 261*a*.

In various implementations, the sensor(s) 261*b* may include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos may be two-dimensional or three-dimensional.

The sensor(s) 261*b* may include sensing electrodes (e.g., the sensing electrodes 262), ventilation sensors (e.g., the ventilation sensors 264), temperature sensors (e.g., the temperature sensor 267), chest compression sensors (e.g., the chest compression sensor 268), etc. For example, the sensing electrodes may include cardiac sensing electrodes. The cardiac sensing electrodes may be conductive and/or capacitive electrodes configured to measure changes in a patient's electrophysiology, for example to measure the patient's ECG information. In an implementation, the sensing electrodes may be configured to measure the transthoracic impedance and/or a heart rate of the patient. The ventilation sensors may include spirometry sensors, flow sensors, pressure sensors, oxygen and/or carbon dioxide sensors such as, for example, one or more of pulse oximetry sensors, oxygenation sensors (e.g., muscle oxygenation/pH), 02 gas sensors and capnography sensors, and combinations thereof. The temperature sensors may include an infrared thermometer, a contact thermometer, a remote thermometer, a liquid crystal thermometer, a thermocouple, a thermistor, etc. and may measure patient temperature internally and/or externally. The chest compression sensor may include one or more motion sensors including, for example, one or more accelerometers, one or more force sensors, one or more magnetic sensors, one or more velocity sensors, one or more displacement sensors, etc. The chest compression sensor may be, for example, but not limited to, a compression puck, a smart-phone, a hand-held device, a wearable device, etc. The chest compression sensor may be configured to detect chest motion imparted by a rescuer and/or an automated chest compression device (e.g., a belt system, a piston system, etc.). The chest compression sensor may provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes may include or be configured to couple to the chest compression sensor.

Continuing with FIG. 20, examples of components of the computing device 104 are shown schematically. In an implementation, the computing device 104 may be configured as a charting device. The computing device 104 may include a processor 420, a memory 421, one or more output devices 430, one or more user input devices 444, and a communications interface 445. FIG. 20 also illustrates schematically examples of components of the computing device 132. In an implementation, the computing device 132 may be configured as a template generation device. As shown in FIG. 20, the computing device 132 may include a processor 323, a memory 321, one or more output devices 330, one or more user input devices 344, and a communications interface 345. FIG. 20 further illustrates schematically examples of components of the server(s) 128. As shown in FIG. 20, the server(s) 128 may include a processor 523, a memory 521, one or more output devices 530, one or more user input devices 544, and a communications interface 545.

Each of the computing device 104 (e.g., the charting device) and the computing device 132 (e.g., the template generation device) may be a computer system, such as a desktop, notebook, mobile, portable, or other type of computing system. Each of these devices 104 and 132 may include one or more servers and/or access one or more servers via a monitor and/or other connected user interface device. Although described as server(s), the server(s) 128 may be another type of computing system including for example a desktop, notebook, mobile, portable, or other type of computing system.

As shown in FIG. 20, each of the devices 104 and 132, along with the server(s) 128 and the medical device 106, includes a bus or other interconnection mechanism that communicably couples the processor, memory, output devices, input devices, and communication interface included therein. The bus may include a PCI/PCI-X or SCSI based system bus depending on the storage devices used, for example.

The processors 220, 320, 420, and 520 may each include a processor, such as, but not limited to, an Intel® Itanium® or Itanium 2® processor(s), or AMD® Opteron® or Athlon MP® processor(s), or Motorola® lines of processors. The communication interfaces 245, 345, 445, and 545 may each be any of an RS-232 port for use with a modem based dialup connection, a 10/100 Ethernet port, or a Gigabit port using copper or fiber, for example. The communication interfaces 245, 345, 445, and 545 may be chosen depending on a network(s) such a Local Area Network (LAN), Wide Area Network (WAN), or any network to which the medical device 106, the computing device 104, the computing device 132, and/or the server(s) 128 may connect. The memories 221, 321, 421, and 521 may be Random Access Memory (RAM), Read Only Memory (ROM), Flash memory, and/or another dynamic volatile and/or non-volatile storage device(s). The memories 221, 321, 421, and 521 may be used to store information and instructions. For example, hard disks such as the Adaptec® family of SCSI drives, an optical disc, an array of disks such as RAID (e.g. the Adaptec family of RAID drives), or any other mass storage devices may be used, for example. The components described above are meant to exemplify some types of possibilities. In no way should the aforementioned examples limit the scope of the disclosure. The memories 221, 321, 421, and 521 may further include removable storage media such as external hard-drives, floppy drives, flash drives, IOMEGA® Zip Drives, Compact Disc-Read Only Memory (CD-ROM), Compact Disc-Re-Writable (CD-RW), or Digital Video Disk-Read Only Memory (DVD-ROM), for example.

Continuing with FIG. 20, the server(s) 128 may include, for example, the one or more storage servers, one or more application servers, and the ePCR data store 130 of FIG. 4. In some examples, the server(s) 128 are configured to exchange messages 1170 with the computing device 132. These messages may include data descriptive of templates generated by the computing device 132 and/or commands for the server(s) 128 to execute a template generation process, such as the rule-based template generation process described herein. In some examples, the server(s) 128 are configured to exchange messages 1160 with the computing device 104. These messages may include data descriptive of ePCRs generated by the computing device 104 and/or commands for the server(s) 128 to execute an ePCR generation process, such as the ePCR generation processes described herein. In some examples, the server(s) 128 are configured to exchange messages 1190 with the medical device 106. These messages may include data descriptive of a patient (e.g., the patient 116 of FIG. 4A) being treated via by the medical device and/or treatment being delivered by the medical device 106.

Although not illustrated in FIG. 20, the computing device 142 as shown in FIG. 4A may include the same structures and/or components described above with regard to the computing devices 104 and 132. Specifically, the computing device 142 may include a processor, a memory, output device(s), input device(s), and a communication interface. Further, the computing device 142 may implement one or more of the functions and capabilities of the computing device 104 and/or 132.

Some examples of the present disclosure include various steps, some of which may be performed by hardware components or may be embodied in machine-executable instructions. These machine-executable instructions may be stored on a non-transitory data storage medium and may be used to cause a general-purpose or a special-purpose processor programmed with the instructions to perform the steps. The non-transitory data storage medium can further to store an operating system and the machine-executable instructions can be included within one or more software applications or programs, such as the ePCR application 160. These programs can implement the features disclosed herein and the methods that they execute. Alternatively, the steps may be performed by a combination of hardware, software, and/or firmware, on one device and/or distributed across multiple devices and/or processors. In addition, some examples of the present disclosure may be performed or implemented, at least in part (e.g., one or more modules), on one or more computer systems, mainframes (e.g., IBM mainframes such as the IBM zSeries, Unisys ClearPath Mainframes, HP Integrity NonStop servers, NEC Express series, and others), or client-server type systems. In addition, specific hardware aspects of examples of the present disclosure may incorporate one or more of these systems, or portions thereof.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure and are intended to be within the scope of the examples discussed herein. Accordingly, the foregoing description and drawings are by way of example only.

The invention claimed is:

1. A system for automatically expediting charting for an emergency medical services (EMS) event, the system comprising:
   a medical device configured to receive patient data from a patient via one or more physiological sensors;
   one or more databases comprising:
      at least one electronic patient care record (ePCR) comprising a plurality of fillable fields configured to store data regarding the EMS event;
      at least a first and a second ePCR template, the first ePCR template specifying a first plurality of values for a first subset of the plurality of fillable fields, the second ePCR template specifying a second plurality of values for a second subset of the plurality of fillable fields; and a computing device configured to communicatively couple to the one or more databases and to the medical device, the computing device comprising at least one user interface, a memory, and at least one processor coupled to the at least one user interface and the memory, the at least one processor being configured to receive, via the at least one user interface, a request to generate a populated ePCR, access, in response to reception of the request, the at least one ePCR, receive a first input indicative of a selection of the first ePCR template, receive a second input indicative of a selection of the second ePCR template, receive the patient data from the medical device, automatically populate at least one portion of the plurality of fillable fields based on the first and the second ePCR templates and on the patient data received from the medical device, to automatically populate comprising to identify, by the at least one processor, non-overlapping fields and overlapping fields in the first and the second subset of the plurality of fillable fields, and automatically populate, by the at least one processor, the non-overlapping fields with values from one of the first and the second plurality of values, and the overlapping fields according to selection rules with one or more values from the first and the second plurality of values, and generate the populated ePCR to comprise a plurality of populated fields based at least in part on the automatic population of the at least one portion of the plurality of fillable fields in the at least one ePCR.

2. The system of claim 1, wherein to automatically populate the non-overlapping fields comprises to:

fill first fields of the non-overlapping fields with values from the first plurality of values, and fill, subsequent to filling the first fields, second fields of the non-overlapping fields with values from the second plurality of values, and wherein to automatically populate the overlapping fields comprises to fill, subsequent to filling the second fields, the overlapping fields with values from the first plurality of values, and apply the selection rules to the overlapping fields using values from the second plurality of values.

3. The system of claim 2, wherein the overlapping fields comprise at least one single-use field and the selection rules are configured to cause the at least one processor to skip the at least one single-use field during application of the selection rules.

4. The system of claim 2, wherein the overlapping fields comprise at least one multi-select field and the selection rules are configured to cause the at least one processor to add a value from the second plurality of values to the at least one multi-select field during application of the selection rules.

5. The system of claim 2, wherein the overlapping fields comprise at least one text field and the selection rules are configured to cause the at least one processor to add a value from the second plurality of values to the at least one text field during application of the selection rules.

6. The system of claim 1, wherein to automatically populate comprises to iterate through each of the non-overlapping and overlapping fields and to:

fill each non-overlapping field with a value from the first or the second plurality of values, and apply the selection rules to each overlapping field using the one or more values from the first and the second plurality of values.

7. The system of claim 6, wherein the overlapping fields comprise at least one single-use field and the selection rules are configured to cause the at least one processor to fill the at least one single-use field with a value from the first plurality of values during application of the selection rules.

8. The system of claim 6, wherein the overlapping fields comprise at least one multi-select field and the selection rules are configured to cause the at least one processor to fill the at least one multi-select field with the one or more values from the first and the second plurality of values during application of the selection rules.

9. The system of claim 6, wherein the overlapping fields comprise at least one text field and the selection rules are configured to cause the at least one processor to fill the at least one text field with the one or more values from the first and the second plurality of values during application of the selection rules.

10. The system of claim 1, wherein the at least one processor is further configured to provide, in response to identification of the overlapping fields, a notification at the at least one user interface indicative of an overlap.

11. The system of claim 1, wherein the at least one processor is further configured to:

identify a single-use field within the overlapping fields; and prompt, in response to identification of the single-use field within the overlapping fields, a user to select a preferred value for the single-use field via the at least one user interface.

12. The system of claim 1, wherein the at least one processor is further configured to automatically store the generated and populated ePCR in the memory.

13. The system of claim 1, wherein the plurality of fillable fields has a total quantity, each fillable field of the plurality of fillable fields has a data type, and the at least one processor is further configured to prevent adjustment of the total quantity and the data type of each fillable field via selection of the first or the second ePCR template.

14. The system of claim 13, wherein the memory stores a configurable parameter that indicates requirements for the total quantity and the data type for each fillable field as mandated by one or more of a data reporting format and a governing body of a region in which the EMS event occurs and the at least one processor is further configured to determine the total quantity and the data type of each fillable field by accessing the configurable parameter.

15. The system of claim 1, wherein the one or more databases comprise a basic emergency call template, a cardiac arrest template, a trauma template, a cancelled call template, a narrative template, a no cardiac arrest template, a no trauma template, a STEMI template, a demographics template, and/or combinations thereof.

16. The system of claim 1, wherein the first and the second plurality of values comprise preprogrammed administrator selected values specific to one or more EMS agencies and one or more EMS events and independent of a patient identity.

17. The system of claim 1, wherein the at least one processor is further configured to:

hide, within the at least one user interface, one or more controls associated with the plurality of populated fields of the ePCR, or highlight, via the at least one user interface, the one or more controls associated with the plurality of populated fields of the ePCR with a transparency, a color, and/or a shading that is different from controls associated with other fields of the ePCR.

18. The system of claim 1, wherein the one or more values of the first and the second plurality of values indicate one or more fields of the first and/or the second subset of the plurality of fillable fields are inapplicable to the EMS event.

19. The system of claim 18, wherein the at least one processor is further configured to:

hide, within the at least one user interface, each control associated with a field of the one or more fields, or provide, via the at least one user interface, one or more controls associated with the one or more fields, each control of the one or more controls having a transparency, a color, and/or a shading that is different from other fields of the ePCR.

20. The system of claim 1, wherein the at least the first and the second ePCR templates correspond to response protocols.

21. The system of claim 1, wherein the at least one processor is configured to execute a mobile device application to generate the populated ePCR.

22. The system of claim 20, wherein the at least one processor is configured to provide at least one user prompt based on the at least the first and the second ePCR templates.

23. The system of claim 1, further comprising an audio input device and/or a haptic input device, wherein the first and/or the second input comprises haptic input and/or audio input.

24. The system of claim 1, further comprising an audio input device configured to detect words within a conversation, wherein the at least one processor is further configured to identify, based on the first input and the second input, key words within the conversation.

25. The system of claim 1, wherein the at least one processor is further configured to receive the first and/or the second input as a transmission of the patient data from the medical device.

26. The system of claim 25, wherein the patient data identifies one or more physiological conditions of a patient and the first and/or the second ePCR template corresponds to the one or more physiological conditions of the patient.

27. The system of claim 25, wherein the medical device is further configured to identify a STEMI condition of the patient based on an electrocardiogram of the patient, the patient data identifies the STEMI condition, and the first and/or the second ePCR template comprises a STEMI template.

28. The system of claim 25, wherein the patient data identifies one or more patient treatments and the first and/or the second ePCR template corresponds to the one or more patient treatments.

* * * * *